United States Patent
Toprac et al.

(10) Patent No.: US 6,238,937 B1
(45) Date of Patent: May 29, 2001

(54) DETERMINING ENDPOINT IN ETCHING PROCESSES USING PRINCIPAL COMPONENTS ANALYSIS OF OPTICAL EMISSION SPECTRA WITH THRESHOLDING

(75) Inventors: Anthony John Toprac; Joseph William Wiseman; Hongyu Yue, all of Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 0 days.

(21) Appl. No.: 09/491,248

(22) Filed: Jan. 26, 2000

Related U.S. Application Data

(60) Provisional application No. 60/163,868, filed on Nov. 5, 1999, and provisional application No. 60/152,897, filed on Sep. 8, 1999.

(51) Int. Cl.[7] .................................................. H01L 21/00
(52) U.S. Cl. ................... 438/9; 156/345; 216/59; 438/14; 438/710
(58) Field of Search ................... 438/9, 14, 16, 438/710, 719, 723, 724, 743, 744; 216/59, 60, 79, 67; 156/345 MT, 345 P

(56) References Cited

U.S. PATENT DOCUMENTS

| | | | |
|---|---|---|---|
| 5,121,337 | 6/1992 | Brown et al. | 364/498 |
| 5,288,367 | 2/1994 | Angell et al. | 156/626 |
| 5,479,340 | 12/1995 | Fox et al. | 364/153 |
| 5,552,016 | * 9/1996 | Ghanayem | 438/9 X |
| 5,658,423 | 8/1997 | Angell et al. | 438/9 |
| 5,862,060 | 1/1999 | Murray, Jr. | 364/528.01 |
| 5,885,472 | * 3/1999 | Miyazaki et al. | 438/9 X |
| 6,060,328 | * 5/2000 | En et al. | 438/9 |
| 6,153,115 | * 11/2000 | Le et al. | 438/9 X |

FOREIGN PATENT DOCUMENTS

WO 99/21210  10/1998  (WO).

OTHER PUBLICATIONS

Jackson, "A User's Guide to Principal Components" 2.8 & 2.9, pp. 41–58, *John Wiley & Sons, Inc.*, 1991.

\* cited by examiner

*Primary Examiner*—William Powell
(74) *Attorney, Agent, or Firm*—Williams, Morgan & Amerson

(57) ABSTRACT

A method is provided for determining an etch endpoint. The method includes collecting intensity data representative of optical emission spectral wavelengths during a plasma etch process. The method further includes analyzing at least a portion of the collected intensity data into at most first and second Principal Components with respective Loadings and corresponding Scores. The method also includes determining the etch endpoint using the respective Loadings and corresponding Scores of the second Principal Component as an indicator for the etch endpoint using thresholding applied to the respective Loadings of the second Principal Component.

42 Claims, 30 Drawing Sheets

DETERMINING ENDPOINT IN ETCHING PROCESSES USING PRINCIPAL COMPONENTS ANALYSIS OF OPTICAL EMISSION SPECTRA WITH THRESHOLDING

SPECIFIC REFERENCE TO PROVISIONAL APPLICATION

The present application claims priority to provisional application Serial No. 60/152,897, filed Sep. 8, 1999, and to provisional application Serial No. 60/163,868, filed Nov. 5, 1999, the entire texts and figures of which are incorporated herein by reference without disclaimer.

BACKGROUND OF THE INVENTION

1. Field of the Invention

This invention relates generally to semiconductor fabrication technology, and, more particularly, to determining the endpoint of etching processes used during semiconductor fabrication.

2. Description of the Related Art

Typically, during semiconductor proceasing, an etching process, such as a reactive ion etch (RIE) process, is employed for etching fine line patterns in a silicon wafer. RIE involves positioning a masked wafer in a chamber that contains plasma. The plasma contains etchant gases that are dissociated in a radio frequency (RF) field so that reactive ions contained in the etchant gases are vertically accelerated toward the wafer surface. The accelerated reactive ions combine chemically with unmasked material on the wafer surface. As a result, volatile etch products are produced. During such etching, single or multiple layers of material or films may be removed. Such material includes, for example, silicon dioxide ($SiO_2$), polysilicon (poly), and silicon nitride ($Si_3N_4$). Endpoint determination or detection refers to control of an etch step and is useful in etching processes in general, and in RIE processes in particular.

As a layer of unmasked material is etched, the volatile etch products are incorporated into the plasma. As the RIE process approaches the interface or end of the layer being etched, the amount of volatile etch product found in the plasma decreases since the amount of unmasked material being etched is reduced due to the etching. The amount of volatile etch product in the plasma may be tracked to determine the endpoint of the RIE process. In other words, the depletion or reduction in the amount of volatile etch product in the plasma during the RIE process typically can be used as an indicator for the end of the etching process.

It is also possible to track a reactive species such as one of the etchant or input gases used to etch a layer of material. As the layer is etched, the reactive species will be depleted and relatively low concentrations of the reactive species will be found in the plasma. However, as more and more of the layer is consumed, the reactive species will be found in the plasma in increasingly higher concentrations. A time trace of the optical emissions from such a reactive species will show an increase in intensity as the layer is etched away. Tracking the intensity of a wavelength for a particular species using optical emission spectroscopy (OES) may also be used for endpoint determination or control of an etch process such as an RIE process.

Conventionally, OES has been used to track the amount of either volatile etch products or reactive species as a function of film thickness. These techniques examine emissions from either the volatile etch products or reactive species in the plasma. As the film interface is reached during etching, the emission species related to the etch of the film will either decrease, in the case of volatile etch products, or increase, in the case of reactive species.

More specifically, during an RIE process, plasma discharge materials, such as etchant, neutral, and reactive ions in the plasma, are continuously excited by electrons and collisions, giving off emissions ranging from ultraviolet to infrared radiation. An optical emission spectrometer diffracts this light into its component wavelengths. Since each species emits light at a wavelength characteristic only of that species, it is possible to associate a certain wavelength with a particular species, and to use this information to detect an etch endpoint.

As an example, in etching $SiO_2$ with $CHF_3$, carbon combines with oxygen from the wafer to form carbon monoxide (CO) as an etch product. It is known that CO emits light at a wavelength of 451 nm, and that this wavelength can be monitored for detecting the endpoint for such an etch. When the oxide is completely etched there is no longer a source of oxygen and the CO peak at 451 nm decreases, thus signaling an etch endpoint.

In the above example, it is known that light emitted from CO at a wavelength of 451 nm would be used for etch endpoint determination or detection. However, such specific wavelength information is generally unavailable, and it has been a formidable task to determine or select an appropriate wavelength to use for accurate etch endpoint determination or control. This difficulty exists because of the numerous possibilities for emissions. In other words, any molecule may emit light at a multitude of different wavelengths due to the many transition states available for de-excitation. Therefore, given the process, the gases utilized, and the material being etched, it is typically not readily known which wavelength in the spectrum to monitor for etch endpoint determination or control. In this regard, the OES spectrum for a typical RIE etch, for example, may be composed of hundreds, or even thousands, of wavelengths in the visible and ultraviolet bands.

Additionally, there is a trend towards using high-density plasma sources to replace RIE. One example is in the use of a high-density, inductively-coupled plasma (ICP). Another example is in the use of electron cyclotron resonance (ECR), which differs from RIE in plasma formation. Generally, ECR operates at a lower pressure than a conventional RIE system, and is, therefore, able to etch finer line trenches anisotropically. Comparison studies of the emissions from high-density ICP, ECR and RIE plasmas show emphasis on different species and different wavelengths for similar input gas compositions. The excitation mechanisms and interactions of the particles at higher densities and/or lower pressures are believed to account for many of these differences. Consequently, the experience and knowledge accumulated from RIE emissions may not carry over to high-density ICP emissions and ECR emissions. In other words, it may not be possible to monitor the same species or wavelengths for etch endpoint determination or detection in high-density ICP or ECR as were monitored for RIE, even if similar materials are being etched using similar input gas compositions.

Conventional techniques for determining an endpoint in an etching process using OES spectra are described, for example, in U.S. Pat. No. 5,288,367, to Angell et al., entitled "End-point Detection," and in U.S. Pat. No. 5,658,423, to Angell et al., entitled "Monitoring and Controlling Plasma Processes via Optical Emission Using Principal Component Analysis." These conventional techniques typically still entail singling out one wavelength to be used for signaling an etch endpoint, however. A conventional technique for effecting process control by statistical analysis of the optical spectrum of a product produced in a chemical process is described, for example, in U.S. Pat. No. 5,862,060, to Murray, Jr., entitled "Maintenance of process control by statistical analysis of product optical spectrum" (the '060 patent). The '060 patent describes measuring the optical spectrum of each member of a calibration sample set of selected products, determining by Principal Component Analysis (PCA) (or Partial Least Squares, PLS) not more than four Principal Components to be used in the calibration sample set, determining the differences in Scores of the Principal Components between a standard "target" product and a test product, and using the differences to control at least one process variable so as to minimize the differences.

However, one drawback associated with conventional techniques for determining an endpoint in an etching process using PCA applied to OES spectra is the uncertainty of how many Principal Components to use in the PCA analysis. This general question in conventional PCA applications is described, for example, in *A User's Guide to Principal Components*, by J. Edward Jackson (Wiley Series in Probability and Mathematical Statistics, New York, 1991), particularly at pages 41–58. Typically, the more Principal Components that are used, the better the PCA approximates the system being analyzed, but the longer it takes to perform the PCA. For example, if all the Principal Components are used, the PCA exactly reproduces the system being analyzed, but the full-Principal Component PCA takes the longest time to perform. However, determining the optimal number of PCA Principal Components to retain is also costly in terms of time and resources involved.

The '060 patent describes, for example, that a very small number of Principal Components, usually no more than 4, suffice to define accurately that sample spectrum space for the purpose of process control and that in some cases only 2 or 3 Principal Components need to be used. However, that still leaves an undesirable amount of uncertainty in whether to use 2, 3 or 4 Principal Components. Furthermore, this uncertainty can lead these conventional techniques to be cumbersome and slow and difficult to implement "on the fly" during real-time etching processes, for example.

Moreover, modem state-of-the art OES systems are capable of collecting thousands of frequencies or wavelengths of optical emission spectra emanating from the glow discharge of gases in a plasma etch chamber. These wavelengths may be associated with the specific chemical species generated from entering reactant gases and their products. These products may result from gas phase reactions as well as reactions on the wafer and chamber wall surfaces. As the surface composition of the wafer shifts from a steady-state etch of exposed surfaces to the complete removal of the etched material, the wavelengths and frequencies of the optical emission spectra also shift. Detection of this shift may allow for etch endpoint determination, indicating the completion of the required etch. Detection of this shift also may allow for termination of the etch process before deleterious effects associated with an over-etch can occur. However, the sheer number of OES frequencies or wavelengths available to monitor to determine an etch endpoint makes the problem of selecting the appropriate OES frequencies or wavelengths to monitor even more severe.

An appropriate etch endpoint signal should have a high signal-to-noise ratio and be reproducible over the variations of the incoming wafers and the state of the processing chamber, for example, whether or not the internal hardware in the processing chamber is worn or new, or whether or not the processing chamber is in a relatively "clean" or relatively "dirty" condition. Further, in particular applications, for example, the etching of contact and/or via holes, the signal-to-noise ratio may inherently be very low simply by virtue of the small percentage of surface area being etched, typically about 1% or so.

The present invention is directed to overcoming, or at least reducing the effects of, one or more of the problems set forth above.

SUMMARY OF THE INVENTION

In one aspect of the present invention, a method is provided for determining an etch endpoint. The method includes collecting intensity data representative of optical emission spectral wavelengths during a plasma etch process. The method further includes analyzing at least a portion of the collected intensity data into at most first and second Principal Components with respective Loadings and corresponding Scores. The method also includes determining the etch endpoint using the respective Loadings and corresponding Scores of the second Principal Component as an indicator for the etch endpoint using thresholding applied to the respective Loadings of the second Principal Component.

In another aspect of the present invention, a computer-readable, program storage device is provided, encoded with instructions that, when executed by a computer, perform a method, the method including collecting intensity data representative of optical emission spectral wavelengths during a plasma etch process. The method further includes analyzing at least a portion of the collected intensity data into at most first and second Principal Components with respective Loadings and corresponding Scores. The method also includes determining the etch endpoint using the respective Loadings and corresponding Scores of the second Principal Component as an indicator for the etch endpoint using thresholding applied to the respective Loadings of the second Principal Component.

In yet another aspect of the present invention, a computer programmed to perform a method is provided, the method including collecting intensity data representative of optical emission spectral wavelengths during a plasma etch process. The method further includes analyzing at least a portion of the collected intensity data into at most first and second Principal Components with respective Loadings and corresponding Scores. The method also includes determining the etch endpoint using the respective Loadings and corresponding Scores of the second Principal Component as an indicator for the etch endpoint using thresholding applied to the respective Loadings of the second Principal Component.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which.

Figure 1:
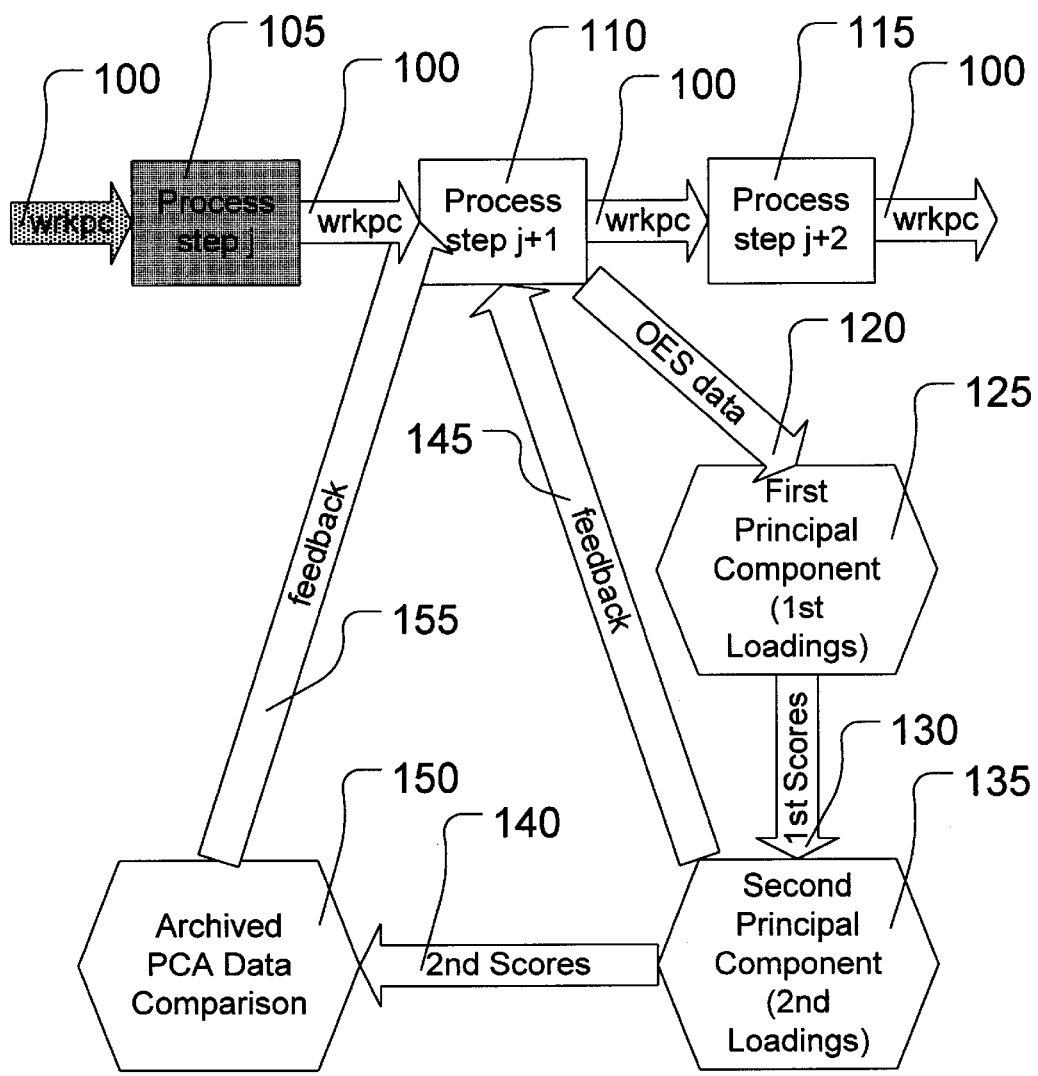
FIGS. 1–7 schematically illustrate a flow diagram for various embodiments of a method according to the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Using optical emission spectroscopy (OES) as an analytical tool in process control (such as in etch endpoint determination) affords the opportunity for on-line measurements in real time. A calibration set of OES spectra bounding the acceptable process space within which a particular property (such as the etch endpoint) is to be controlled may be obtained by conventional means. Applying a multivariant statistical method such as Principal Components Analysis (PCA) to the calibration set of OES spectra affords a method of identifying the most important characteristics (Principal Components and respective "Loadings") of the set of OES spectra that govern the controlled property, and are inherently related to the process. Control then is effected by using only two of such characteristics (Principal Components and respective Loadings and corresponding Scores), which can be determined quickly and simply from the measured spectra, as the control criteria to be applied to the process as a whole. The result is a very effective way of controlling a complex process using only 2 criteria (the first and second Principal Components and respective Loadings and corresponding Scores) objectively determined from a calibration set, which can be applied in real time and virtually continuously, resulting in a well-controlled process that is (ideally) invariant.

In particular, we have found that the second Principal Component contains a very robust, high signal-to-noise indicator for etch endpoint determination. In various illustrative embodiments, PCA may be applied to the OES data, either the whole spectrum or at least a portion of the whole spectrum. If the engineer and/or controller knows that only a portion of the OES data contains useful information, PCA may be applied only to that portion, for example. The PCA derives two or more of the Principal Components and respective Loadings and corresponding Scores. The respective Loadings may be used to determine which wavelengths could be used to determine an etch endpoint and also what the appropriate weightings for such wavelengths could be. The corresponding Scores may be used to detect the etch endpoint, for example, by following time traces of the corresponding Scores.

In one illustrative embodiment of a method according to the present invention, as shown in FIGS. 1–7, described in more detail below, archived data sets of OES wavelengths (or frequencies), from wafers that had previously been plasma etched, may be processed and the weighted linear combination of the intensity data, representative of OES wavelengths (or frequencies) collected over time during the plasma etch, defined by the second Principal Component may be used to determine an etch endpoint. For example, PCA may be applied to the archived OES data and the respective Loadings for the first two Principal Components may be retained as model information. When new OES data are taken during an etch process, approximations to the first two Scores for the new OES data are calculated by using the respective Loadings for the first two Principal Components retained from the model information derived from the archived OES data. The approximations to the second Score (corresponding to the second Principal Component) may be used to determine the etch endpoint, by plotting the approximation to the second Score as a time trace and looking for an abrupt change in the value of the approximation to the second Score on the time trace, for example.

In another illustrative embodiment of a method according to the present invention, as shown in FIGS. 8–14, described in more detail below, only the OES wavelengths (or frequencies) above a certain threshold value in weighting, as defined by the second Principal Component, may be used to determine an etch endpoint. For example, instead of using Loadings for all wavelengths sampled, the Loadings may be compared with a certain threshold value (such as approximately 0.03) and only those wavelengths with loadings greater than or equal to the threshold value may be used to determine the etch endpoint. In this way, relatively unimportant wavelengths may be ignored and the robustness of this embodiment may be further enhanced.

In yet another illustrative embodiment of a method according to the present invention, as shown in FIGS. 15–21, described in more detail below, the determination of the second Principal Component may be performed real-time in an early part of a plasma etching process, and this determination of the second Principal Component may be used to determine an etch endpoint. When used in real-time, the respective model Loadings can be further adjusted based on real-time calculations. These adjustments can be wafer-to-wafer (during serial etching of a batch of wafers) and/or within the etching of each single wafer. For wafer-to-wafer adjustments, the Loadings from previous wafers may be used as the model Loadings. Within the etching of individual wafers, the model Loadings may be calculated from an early portion of the plasma etching process where the etching endpoint almost certainly will not be occurring.

Any of these three embodiments may be applied in real-time etch processing. Alternatively, either of the first two illustrative embodiments may be used as an identification technique when using batch etch processing, with archived data being applied statistically, to determine an etch endpoint for the batch.

Various embodiments of the present invention are applicable to any plasma etching process affording a characteristic data set whose quality may be said to define the "success" of the plasma etching process and whose identity may be monitored by suitable spectroscopic techniques such as OES. The nature of the plasma etching process itself is not critical, nor is the specific identity of the workpieces (such as semiconducting silicon wafers) whose spectra are being obtained. However, an "ideal" or "target" characteristic data set should be able to be defined, having a known and/or determinable OES spectrum, and variations in the plasma etching process away from the target characteristic data set should be able to be controlled (ie., reduced) using identifiable independent process variables, e.g., etch endpoints, plasma energy and/or temperature, plasma chamber pressure, etchant concentrations, flow rates, and the like. The ultimate goal of process control is to maintain a properly operating plasma etching process at status quo. When a plasma etching process has been deemed to have reached a proper operating condition, process control should be able to maintain it by proper adjustment of plasma etching process parameters such as etch endpoints, temperature, pressure, flow rate, residence time in the plasma chamber, and the like. At proper operating conditions, the plasma etching process affords the "ideal" or "target" characteristics.

One feature of illustrative embodiments of our control process is that the spectrum of the stream, hereafter referred to as the test stream, may be obtained continuously (or in a near-continuous manner) on-line, and compared to the spectrum of the "target" stream, hereafter referred to as the standard stream. The difference in the two spectra may then be used to adjust one or more of the process variables so as to produce a test stream more nearly identical with the standard stream. However, as envisioned in practice, the complex spectral data will be reduced and/or compressed to no more than 2 numerical values that define the coordinates of the spectrum in the Principal Component space of the process subject to control. Typically small, incremental adjustments will be made so that the test stream approaches the standard stream while minimizing oscillation, particularly oscillations that will tend to lose process control rather than exercise control. Adjustments will be made according to one or more suitable algorithms based on process modeling, process experience, and/or artificial intelligence feedback, as described more fully within.

In principle, more than one process variable may be subject to control, although it is apparent that as the number of process variables under control increases so does the complexity of the control process. Similarly, more than one test stream and more than one standard stream may be sampled, either simultaneously or concurrently, again with an increase in complexity. In its simplest form, where there is one test stream and one process variable under control, one may analogize the foregoing to the use of a thermocouple in a reaction chamber to generate a heating voltage based on the sensed temperature, and to use the difference between the generated heating voltage and a set point heating voltage to send power to the reaction chamber in proportion to the difference between the actual temperature and the desired temperature which, presumably, has been predetermined to be the optimum temperature. Since the result of a given change in a process variable can be determined quickly, this new approach opens up the possibility of controlling the process by an automated "trial and error" feedback system, since unfavorable changes can be detected quickly. Illustrative embodiments of the present invention may operate as null-detectors with feedback from the set point of operation, where the feedback signal represents the deviation of the total composition of the stream from a target composition.

In one illustrative embodiment, OES spectra are taken of characteristic data sets of plasma etching processes of various grades and quality, spanning the maximum range of values typical of the particular plasma etching processes. Such spectra then are representative of the entire range of plasma etching processes and are often referred to as calibration samples. Note that because the characteristic data sets are representative of those formed in the plasma etching processes, the characteristic data sets constitute a subset of those that define the boundaries of representative processes. It will be recognized that there is no subset that is unique, that many different subsets may be used to define the boundaries, and that the specific samples selected are not critical.

Subsequently, the spectra of the calibration samples are subjected to the well-known statistical technique of Principal Component Analysis (PCA) to afford a small number of Principal Components that largely determine the spectrum of any sample. The Principal Components, which represent the major contributions to the spectral changes, are obtained from the calibration samples by PCA or Partial Least Squares (PLS). Thereafter, any new sample may be assigned various contributions of these Principal Components that would reproduce the spectrum of the new sample. The amount of each Principal Component required is called a Score, and time traces of these Scores, tracking how various of the Scores are changing with time, are used to detect deviations from the "target" spectrum.

In mathematical terms, a set of m time samples of an OES for a workpiece (such as a semiconductor wafer having various process layers formed thereon) taken at n channels or wavelengths or frequencies may be arranged as a rectangular n×m matrix X. In other words, the rectangular n×m matrix X may be comprised of 1 to n rows (each row corresponding to a separate OES channel or wavelength or frequency taken or sampled) and 1 to m columns (each column corresponding to a separate OES spectrum time sample). The values of the rectangular n×m matrix X may be counts representing the intensity of the OES spectrum, or ratios of spectral intensities (normalized to a reference intensity), or logarithms of such ratios, for example. The rectangular n×m matrix X may have rank r, where $r \leq \min\{m,n\}$ is the maximum number of independent variables in the matrix X. The use of PCA, for example, generates a set of Principal Components P (whose "Loadings," or components, represent the contributions of the various spectral components) as an eigenmatrix (a matrix whose columns are eigenvectors) of the equation $((X-M)(X-M)^T)P=\Lambda^2 P$, where M is a rectangular n×m matrix of the mean values of the columns of X, $\Lambda^2$ is an n×n diagonal matrix of the squares of the eigenvalues $\lambda_i$, i=1,2, . . . ,r, of the mean-scaled matrix X−M, and a Scores matrix, T, with $X-M=PT^T$ and $(X-M)^T=(PT^T)_T=(T^T)^T P^T=TP^T$, so that ((X−

M)$(X-M)^T)P=((PT^T)(TP^T))P$ and $((PT^T)(TP^T))P=(P(T^TT)P^T)P=P(T^TT)=\Lambda^2 P$. The rectangular n×m matrix X, also denoted $X_{n \times m}$, may have elements $x_{ij}$, where $i=1,2,\ldots,n$, and $j=1,2,\ldots,m$, and the rectangular m×n matrix $X^T$, the transpose of the rectangular n×m matrix X, also denoted $(X^T)_{m \times n}$, may have elements $x_{ji}$, where $i=1,2,\ldots,n$, and $j=1,2,\ldots,m$. The n×n matrix $(X-M)(X-M)^T$ is the covariance matrix $S_{n \times n}$, having elements $s_{ij}$, where $i=1,2,\ldots,n$, and $j=1,2,\ldots,n$, defined so that:

$$s_{ij} = \frac{m\sum_{k=1}^{m} x_{ik}x_{jk} - \sum_{k=1}^{m} x_{ik} \sum_{k=1}^{m} x_{jk}}{m(m-1)},$$

corresponding to the rectangular n×m matrix $X_{n \times m}$.

For the purposes of the process control envisioned in this application, we have found that only 2 Principal Components are needed to accommodate the data for a large range of plasma etching processes from a variety of plasma etching chambers. The spectrum of the standard sample is then expressed in terms of time traces of the Scores of the 2 Principal Components used, the spectrum of the test sample is similarly expressed, and the differences in the time traces of the Scores are used to control the process variables. Thus, no direct correlations between the sample spectrum and plasma etch endpoints need be known. In fact, the nature of the sample itself need not be known, as long as there is a standard, the OES spectrum of the standard is known, a set of at most 2 Principal Components is identified for the class of test stream samples, and one can establish how to use the 2 Principal Components to control the process variables (as discussed more fully below).

The spectrum of any sample may be expressed as a 2-dimensional representation of the intensity of emission at a particular wavelength vs. the wavelength. That is, one axis represents intensity, the other wavelength. The foregoing characterization of a spectrum is intended to incorporate various transformations that are mathematically covariant; e.g., instead of emission one might use absorption and/or transmission, and either may be expressed as a percentage or logarithmically. Whatever the details, each spectrum may be viewed as a vector. The group of spectra arising from a group of samples similarly corresponds to a group of vectors. If the number of samples is N, there are at most N distinct spectra. If, in fact, none of the spectra can be expressed as a linear combination of the other spectra, then the set of spectra define an N-dimensional spectrum space. However, in the cases of interest here, where a particular stream in an invariant plasma etching process is being sampled, we have observed that, in fact, any particular spectrum may be accurately represented as a linear combination of a small number, M=2, of other spectra—their "Principal Components" that we refer to as "working" spectra. These "working" spectra may be viewed as the new basis set, i.e., linearly independent vectors that define the 2-dimensional spectrum space in which the samples reside. The spectrum of any other sample is then a linear combination of the "working" spectra (or is at least projectable onto the 2-dimensional spectrum space spanned by the "working" spectra). Our experience demonstrates that the samples typically reside in, at most, a 2-dimensional spectrum space, and that this 2-dimensional model suffices as a practical matter.

Statistical methods are available to determine the set of "working" spectra appropriate for any sample set, and the method of PCA is the one most favored in the practice of the present invention, although other methods, e.g., partial least squares, non-linear partial least squares, (or, with less confidence, multiple linear regression), also may be utilized. The "working" spectra, or the linearly independent vectors defining the sample spectrum space, are called Principal Components. Thus the spectrum of any sample is a linear combination of the Principal Components. The fractional contribution of any Principal Component is called the Score for the respective Principal Component. Hence, the spectrum of any sample completely defines a set of Scores that greatly reduces the apparent complexity of comparing different spectra. In fact, it has been found that for many processes of interest in semiconductor processing, a very small number of Principal Components, no more than 2, suffice to define accurately the sample spectrum space for the purpose of process control. This means that the process of characterizing the difference between a test sample and the standard sample comes down to the difference between only 2 numbers—the Scores of the respective 2 Principal Components for the sample and "target." It is significant to note that the small number of Scores embodies a great deal of information about the samples and the process, and that only 2 numbers are adequate to control the process within quite close tolerances. By using the null approach of illustrative embodiments of the present invention, the use of Scores is simplified to teaching small shifts (and restoring them to zero) rather than drawing conclusions and/or correlations from the absolute values of the Scores.

Although other methods may exist, three methods for computing Principal Components are as follows:

1. eigenanalysis (EIG);
2. singular value decomposition (SVD); and
3. nonlinear iterative partial least squares (NIPALS).

Each of the first two methods, EIG and SVD, simultaneously calculates all possible Principal Components, whereas the NIPALS method allows for calculation of one Principal Component at a time. However, an iterative approach to finding eigenvalues and eigenvectors, known as the power method, described more fully below, also allows for calculation of one Principal Component at a time. There are as many Principal Components as there are channels (or wavelengths or frequencies). The power method may efficiently use computing time.

For example, consider the 3×2 matrix A, its transpose, the 2×3 matrix $A^T$, their 2×2 matrix product $A^TA$, and their 3×3 matrix product $AA^T$:

$$A = \begin{pmatrix} 1 & 1 \\ 1 & 0 \\ 1 & -1 \end{pmatrix}$$

$$A^T = \begin{pmatrix} 1 & 1 & 1 \\ 1 & 0 & -1 \end{pmatrix}$$

$$A^TA = \begin{pmatrix} 1 & 1 & 1 \\ 1 & 0 & -1 \end{pmatrix} \begin{pmatrix} 1 & 1 \\ 1 & 0 \\ 1 & -1 \end{pmatrix} = \begin{pmatrix} 3 & 0 \\ 0 & 2 \end{pmatrix}$$

$$AA^T = \begin{pmatrix} 1 & 1 \\ 1 & 0 \\ 1 & -1 \end{pmatrix} \begin{pmatrix} 1 & 1 & 1 \\ 1 & 0 & -1 \end{pmatrix} = \begin{pmatrix} 2 & 1 & 0 \\ 1 & 1 & 1 \\ 0 & 1 & 2 \end{pmatrix}.$$

EIG reveals that the eigenvalues $\lambda$ of the matrix product $A^TA$ are 3 and 2. The eigenvectors of the matrix product $A^TA$ are solutions t of the equation $(A^TA)t = \lambda t$, and may be seen by inspection to be $t_1^T = (1,0)$ and $t_2^T = (0,1)$, belonging to the eigenvalues $\lambda_1 = 3$ and $\lambda_2 = 2$, respectively.

The power method, for example, may be used to determine the eigenvalues $\lambda$ and eigenvectors p of the matrix product $AA^T$, where the eigenvalues $\lambda$ and the eigenvectors p are solutions p of the equation $(AA^T)p=\lambda p$. A trial eigenvector $p^T=(1,1,1)$ may be used:

$$(AA^T)\underline{p} = \begin{pmatrix} 2 & 1 & 0 \\ 1 & 1 & 1 \\ 0 & 1 & 2 \end{pmatrix} \begin{pmatrix} 1 \\ 1 \\ 1 \end{pmatrix} = \begin{pmatrix} 3 \\ 3 \\ 3 \end{pmatrix} = 3 \begin{pmatrix} 1 \\ 1 \\ 1 \end{pmatrix} = \lambda_1 \underline{p}_1.$$

This indicates that the trial eigenvector $p^T=(1,1,1)$ happened to correspond to the eigenvector $p_1^T=(1,1,1)$ belonging to the eigenvalue $\lambda_1=3$. The power method then proceeds by subtracting the outer product matrix $p_1 p_1^T$ from the matrix product $AA^T$ to form a residual matrix $R_1$:

$$R_1 = \begin{pmatrix} 2 & 1 & 0 \\ 1 & 1 & 1 \\ 0 & 1 & 2 \end{pmatrix} - \begin{pmatrix} 1 \\ 1 \\ 1 \end{pmatrix}(1 \; 1 \; 1) = \begin{pmatrix} 2 & 1 & 0 \\ 1 & 1 & 1 \\ 0 & 1 & 2 \end{pmatrix} - \begin{pmatrix} 1 & 1 & 1 \\ 1 & 1 & 1 \\ 1 & 1 & 1 \end{pmatrix} = \begin{pmatrix} 1 & 0 & -1 \\ 0 & 0 & 0 \\ -1 & 0 & 1 \end{pmatrix}.$$

Another trial eigenvector $p^T=(1,0,-1)$ may be used:

$$(AA^T - \underline{p}_1 \underline{p}_1^T)\underline{p} = R_1 \underline{p} = \begin{pmatrix} 1 & 0 & -1 \\ 0 & 0 & 0 \\ -1 & 0 & 1 \end{pmatrix} \begin{pmatrix} 1 \\ 0 \\ -1 \end{pmatrix} = \begin{pmatrix} 2 \\ 0 \\ -2 \end{pmatrix} = 2 \begin{pmatrix} 1 \\ 0 \\ -1 \end{pmatrix} = \lambda_2 \underline{p}_2.$$

This indicates that the trial eigenvector $p^T=(1,0,-1)$ happened to correspond to the eigenvector $p_2^T=(1,0,-1)$ belonging to the eigenvalue $\lambda_2=2$. The power method then proceeds by subtracting the outer product matrix $p_2 p_2^T$ from the residual matrix $R_1$ to form a second residual matrix $R_2$:

$$R_2 = \begin{pmatrix} 1 & 0 & -1 \\ 0 & 0 & 0 \\ -1 & 0 & 1 \end{pmatrix} - \begin{pmatrix} 1 \\ 0 \\ -1 \end{pmatrix}(1 \; 0 \; -1) =$$

$$\begin{pmatrix} 1 & 0 & -1 \\ 0 & 0 & 0 \\ -1 & 0 & 1 \end{pmatrix} - \begin{pmatrix} 1 & 0 & -1 \\ 0 & 0 & 0 \\ -1 & 0 & 1 \end{pmatrix} = \begin{pmatrix} 0 & 0 & 0 \\ 0 & 0 & 0 \\ 0 & 0 & 0 \end{pmatrix}.$$

The fact that the second residual matrix $R_2$ vanishes indicates that the eigenvalue $\lambda_3=0$ and that the eigenvector $p_3$ is completely arbitrary. The eigenvector $p_3$ may be conveniently chosen to be orthogonal to the eigenvectors $p_1^T=(1,1,1)$ and $p_2^T=(1,0,-1)$, so that the eigenvector $p_3^T=(1,-2,1)$. Indeed, one may readily verify that:

$$(AA^T)\underline{p}_3 = \begin{pmatrix} 2 & 1 & 0 \\ 1 & 1 & 1 \\ 0 & 1 & 2 \end{pmatrix} \begin{pmatrix} 1 \\ -2 \\ 1 \end{pmatrix} = \begin{pmatrix} 0 \\ 0 \\ 0 \end{pmatrix} = 0 \begin{pmatrix} 1 \\ -2 \\ 1 \end{pmatrix} = \lambda_3 \underline{p}_3.$$

Similarly, SVD of A shows that $A=PT^T$, where P is the Principal Component matrix and T is the Scores matrix:

$$A = \begin{pmatrix} 1/\sqrt{3} & 1/\sqrt{2} & 1/\sqrt{6} \\ 1/\sqrt{3} & 0 & -2/\sqrt{6} \\ 1/\sqrt{3} & -1/\sqrt{2} & 1/\sqrt{6} \end{pmatrix} \begin{pmatrix} \sqrt{3} & 0 \\ 0 & \sqrt{2} \\ 0 & 0 \end{pmatrix} \begin{pmatrix} 1 & 0 \\ 0 & 1 \end{pmatrix} =$$

$$\begin{pmatrix} 1/\sqrt{3} & 1/\sqrt{2} & 1/\sqrt{6} \\ 1/\sqrt{3} & 0 & -2/\sqrt{6} \\ 1/\sqrt{3} & -1/\sqrt{2} & 1/\sqrt{6} \end{pmatrix} \begin{pmatrix} \sqrt{3} & 0 \\ 0 & \sqrt{2} \\ 0 & 0 \end{pmatrix}.$$

SVD confirms that the singular values of A are $\sqrt{3}$ and $\sqrt{2}$, the positive square roots of the eigenvalues $\lambda_1=3$ and $\lambda_2=2$ of the matrix product $A^TA$. Note that the columns of the Principal Component matrix P are the orthonormalized eigenvectors of the matrix product $AA^T$.

Likewise, SVD of $A^T$ shows that $A^T=TP^T$:

$$A^T = \begin{pmatrix} 1 & 0 \\ 0 & 1 \end{pmatrix} \begin{pmatrix} \sqrt{3} & 0 & 0 \\ 0 & \sqrt{2} & 0 \end{pmatrix} \begin{pmatrix} 1/\sqrt{3} & 1/\sqrt{3} & 1/\sqrt{3} \\ 1/\sqrt{2} & 0 & -1/\sqrt{2} \\ 1/\sqrt{6} & -2/\sqrt{6} & 1/\sqrt{6} \end{pmatrix} =$$

$$A^T = \begin{pmatrix} \sqrt{3} & 0 & 0 \\ 0 & \sqrt{2} & 0 \end{pmatrix} \begin{pmatrix} 1/\sqrt{3} & 1/\sqrt{3} & 1/\sqrt{3} \\ 1/\sqrt{2} & 0 & -1/\sqrt{2} \\ 1/\sqrt{6} & -2/\sqrt{6} & 1/\sqrt{6} \end{pmatrix} = TP^T.$$

SVD confirms that the (non-zero) singular values of $A^T$ are $\sqrt{3}$ and $\sqrt{2}$, the positive square roots of the eigenvalues $\lambda_1=3$ and $\lambda_2=2$ of the matrix product $AA^T$. Note that the columns of the Principal Component matrix P (the rows of the Principal Component matrix $P^T$) are the orthonormalized eigenvectors of the matrix product $AA^T$. Also note that the non-zero elements of the Scores matrix T are the positive square roots $\sqrt{3}$ and $\sqrt{2}$ of the (non-zero) eigenvalues $\lambda_1=3$ and $\lambda_2=2$ of both of the matrix products $A^TA$ and $AA^T$.

Taking another example, consider the 4×3 matrix B, its transpose, the 3×4 matrix $B^T$, their 3×3 matrix product $B^TB$, and their 4×4 matrix product $BB^T$:

$$B = \begin{pmatrix} 1 & 1 & 0 \\ 1 & 0 & 1 \\ 1 & 0 & -1 \\ 1 & -1 & 0 \end{pmatrix}$$

$$B^T = \begin{pmatrix} 1 & 1 & 1 & 1 \\ 1 & 0 & 0 & -1 \\ 0 & 1 & -1 & 0 \end{pmatrix}$$

$$B^T B = \begin{pmatrix} 1 & 1 & 1 & 1 \\ 1 & 0 & 0 & -1 \\ 0 & 1 & -1 & 0 \end{pmatrix} \begin{pmatrix} 1 & 1 & 0 \\ 1 & 0 & 1 \\ 1 & 0 & -1 \\ 1 & -1 & 0 \end{pmatrix} = \begin{pmatrix} 4 & 0 & 0 \\ 0 & 2 & 0 \\ 0 & 0 & 2 \end{pmatrix}$$

$$BB^T = \begin{pmatrix} 1 & 1 & 0 \\ 1 & 0 & 1 \\ 1 & 0 & -1 \\ 1 & -1 & 0 \end{pmatrix} \begin{pmatrix} 1 & 1 & 1 & 1 \\ 1 & 0 & 0 & -1 \\ 0 & 1 & -1 & 0 \end{pmatrix} = \begin{pmatrix} 2 & 1 & 1 & 0 \\ 1 & 2 & 0 & 1 \\ 1 & 0 & 2 & 1 \\ 0 & 1 & 1 & 2 \end{pmatrix}.$$

EIO reveals that the eigenvalues of the matrix product $B^TB$ are 4, 2 and 2. The eigenvectors of the matrix product $B^TB$ are solutions t of the equation $(B^TB)t=\lambda t$, and may be seen by inspection to be $t_1^T=(0,1,0)$, and $t_3^T=(0,0,1)$, belonging to the eigenvalues $\lambda_1=4$, $\lambda_2=2$, and $\lambda_3=2$, respectively.

The power method, for example, may be used to determine the eigenvalues $\lambda$ and eigenvectors p of the matrix product $BB^T$, where the eigenvalues $\lambda$ and the eigenvectors p are solutions p of the equation $(BB^T)p=\lambda p$. A trial eigenvector $p^T=(1,1,1,1)$ may be used:

$$(BB^T)\underline{p} = \begin{pmatrix} 2 & 1 & 1 & 0 \\ 1 & 2 & 0 & 1 \\ 1 & 0 & 2 & 1 \\ 0 & 1 & 1 & 2 \end{pmatrix} \begin{pmatrix} 1 \\ 1 \\ 1 \\ 1 \end{pmatrix} = \begin{pmatrix} 4 \\ 4 \\ 4 \\ 4 \end{pmatrix} = 4 \begin{pmatrix} 1 \\ 1 \\ 1 \\ 1 \end{pmatrix} = \lambda_1 \underline{p}_1.$$

This indicates that the trial eigenvector $p^T=(1,1,1,1)$ happened to correspond to the eigenvector $p_1^T=(1,1,1,1)$ belonging to the eigenvalue $\lambda_1=4$. The power method then proceeds by subtracting the outer product matrix $p_1 p_1^T$ from the matrix product $BB^T$ to form a residual matrix $R_1$:

$$R_1 = \begin{pmatrix} 2 & 1 & 1 & 0 \\ 1 & 2 & 0 & 1 \\ 1 & 0 & 2 & 1 \\ 0 & 1 & 1 & 2 \end{pmatrix} - \begin{pmatrix} 1 & 1 & 1 & 1 \\ 1 & 1 & 1 & 1 \\ 1 & 1 & 1 & 1 \\ 1 & 1 & 1 & 1 \end{pmatrix} = \begin{pmatrix} 1 & 0 & 0 & -1 \\ 0 & 1 & -1 & 0 \\ 0 & -1 & 1 & 0 \\ -1 & 0 & 0 & 1 \end{pmatrix}.$$

Another trial eigenvector $p^T=(1,0,0,-1)$ may be used:

$$(BB^T - \underline{p}_1 \underline{p}_1^T)\underline{p} =$$

$$R_1 \underline{p} = \begin{pmatrix} 1 & 0 & 0 & -1 \\ 0 & 1 & -1 & 0 \\ 0 & -1 & 1 & 0 \\ -1 & 0 & 0 & 1 \end{pmatrix} \begin{pmatrix} 1 \\ 0 \\ 0 \\ -1 \end{pmatrix} = \begin{pmatrix} 2 \\ 0 \\ 0 \\ -2 \end{pmatrix} = 2 \begin{pmatrix} 1 \\ 0 \\ 0 \\ -1 \end{pmatrix} = \lambda_2 \underline{p}_2.$$

This indicates that the trial eigenvector $p^T=(1,0,0,-1)$ happened to correspond to the eigenvector $p_2^T=(1,0,0,-1)$ belonging to the eigenvalue $\lambda_2=2$. The power method then proceeds by subtracting the outer product matrix $p_2 p_2^T$ from the residual matrix $R_1$ to form a second residual matrix $R_2$:

$$R_2 = \begin{pmatrix} 1 & 0 & 0 & -1 \\ 0 & 1 & -1 & 0 \\ 0 & -1 & 1 & 0 \\ -1 & 0 & 0 & 1 \end{pmatrix} - \begin{pmatrix} 1 & 0 & 0 & -1 \\ 0 & 0 & 0 & 0 \\ 0 & 0 & 0 & 0 \\ -1 & 0 & 0 & 1 \end{pmatrix} = \begin{pmatrix} 0 & 0 & 0 & 0 \\ 0 & 1 & -1 & 0 \\ 0 & -1 & 1 & 0 \\ 0 & 0 & 0 & 0 \end{pmatrix}.$$

Another trial eigenvector $p^T=(0,1,-1,0)$ may be used:

$$(BB^T - \underline{p}_2 \underline{p}_2^T)\underline{p} =$$

$$R_2 \underline{p} = \begin{pmatrix} 0 & 0 & 0 & 0 \\ 0 & 1 & -1 & 0 \\ 0 & -1 & 1 & 0 \\ 0 & 0 & 0 & 0 \end{pmatrix} \begin{pmatrix} 0 \\ 1 \\ -1 \\ 0 \end{pmatrix} = \begin{pmatrix} 0 \\ 2 \\ -2 \\ 0 \end{pmatrix} = 2 \begin{pmatrix} 0 \\ 1 \\ -1 \\ 0 \end{pmatrix} = \lambda_3 \underline{p}_3.$$

This indicates that the trial eigenvector $p^T=(0,1,-1,0)$ happened to correspond to the eigenvector $p_3^T=(0,-1,0)$ belonging to the eigenvalue $\lambda_3=2$. The power method then proceeds by subtracting the outer product matrix $p_3 p_3^T$ from the second residual matrix $R_2$ to form a third residual matrix $R_3$:

$$R_3 = \begin{pmatrix} 0 & 0 & 0 & 0 \\ 0 & 1 & -1 & 0 \\ 0 & -1 & 1 & 0 \\ 0 & 0 & 0 & 0 \end{pmatrix} - \begin{pmatrix} 0 & 0 & 0 & 0 \\ 0 & 1 & -1 & 0 \\ 0 & -1 & 1 & 0 \\ 0 & 0 & 0 & 0 \end{pmatrix} = \begin{pmatrix} 0 & 0 & 0 & 0 \\ 0 & 0 & 0 & 0 \\ 0 & 0 & 0 & 0 \\ 0 & 0 & 0 & 0 \end{pmatrix}.$$

The fact that the third residual matrix $R_3$ vanishes indicates that the eigenvalue $\lambda_{4=0}$ and that the eigenvector $p_4$ is completely arbitrary. The eigenvector $p_4$ may be conveniently chosen to be orthogonal to the eigenvectors $p_1^T=(1,1,1,1)$, $p_2^T=(1,0,0,-1)$, and $p_3^T=(0,1,-1)$, so that the eigenvector $p_4^T=(1,-1,-1,1)$. Indeed, one may readily verify that:

$$(BB^T)\underline{p}_4 = \begin{pmatrix} 2 & 1 & 1 & 0 \\ 1 & 2 & 0 & 1 \\ 1 & 0 & 2 & 1 \\ 0 & 1 & 1 & 2 \end{pmatrix} \begin{pmatrix} 1 \\ -1 \\ -1 \\ 1 \end{pmatrix} = \begin{pmatrix} 0 \\ 0 \\ 0 \\ 0 \end{pmatrix} = 0 \begin{pmatrix} 1 \\ -1 \\ -1 \\ 1 \end{pmatrix} = \lambda_4 \underline{p}_4.$$

In this case, since the eigenvalues $\lambda_2=2$ and $\lambda_3=2$ are equal, and, hence, degenerate, the eigenvectors $p_2^T=(1,0,0,-1)$ and $p_3^T=(0,1,-1,0)$ belonging to the degenerate eigenvalues $\lambda_2=2=\lambda_3$ may be conveniently chosen to be orthonormal. A Gram-Schmidt orthonormalization procedure may be used, for example.

Similarly, SVD of B shows that $B=PT^T$, where P is the Principal Component matrix and T is the Scores matrix:

$$B = \begin{pmatrix} 1/2 & 1/\sqrt{2} & 0 & 1/2 \\ 1/2 & 0 & 1/\sqrt{2} & -1/2 \\ 1/2 & 0 & -1/\sqrt{2} & -1/2 \\ 1/2 & -1/\sqrt{2} & 0 & 1/2 \end{pmatrix} \begin{pmatrix} 2 & 0 & 0 \\ 0 & \sqrt{2} & 0 \\ 0 & 0 & \sqrt{2} \\ 0 & 0 & 0 \end{pmatrix} \begin{pmatrix} 1 & 0 & 0 \\ 0 & 1 & 0 \\ 0 & 0 & 1 \end{pmatrix} =$$

$$B = \begin{pmatrix} 1/2 & 1/\sqrt{2} & 0 & 1/2 \\ 1/2 & 0 & 1/\sqrt{2} & -1/2 \\ 1/2 & 0 & -1/\sqrt{2} & -1/2 \\ 1/2 & -1/\sqrt{2} & 0 & 1/2 \end{pmatrix} \begin{pmatrix} 2 & 0 & 0 \\ 0 & \sqrt{2} & 0 \\ 0 & 0 & \sqrt{2} \\ 0 & 0 & 0 \end{pmatrix} = PT^T.$$

SVD confirms that the singular values of B are 2, $\sqrt{2}$ and $\sqrt{2}$, the positive square roots of the eigenvalues $\lambda_1=4$, $\lambda_2=2$ and $\lambda_3=2$ of the matrix product $B^T B$.

Likewise, SVD of $B^T$ shows that:

$$B^T = \begin{pmatrix} 1 & 0 & 0 \\ 0 & 1 & 0 \\ 0 & 0 & 1 \end{pmatrix} \begin{pmatrix} 2 & 0 & 0 & 0 \\ 0 & \sqrt{2} & 0 & 0 \\ 0 & 0 & \sqrt{2} & 0 \end{pmatrix}$$

$$\begin{pmatrix} 1/2 & 1/2 & 1/2 & 1/2 \\ 1/\sqrt{2} & 0 & 0 & -1/\sqrt{2} \\ 0 & 1/\sqrt{2} & -1/\sqrt{2} & 0 \\ 1/2 & -1/2 & -1/2 & 1/2 \end{pmatrix} = B^T =$$

$$\begin{pmatrix} 2 & 0 & 0 & 0 \\ 0 & \sqrt{2} & 0 & 0 \\ 0 & 0 & \sqrt{2} & 0 \end{pmatrix} \begin{pmatrix} 1/2 & 1/2 & 1/2 & 1/2 \\ 1/\sqrt{2} & 0 & 0 & -1/\sqrt{2} \\ 0 & 1/\sqrt{2} & -1/\sqrt{2} & 0 \\ 1/2 & -1/2 & -1/2 & 1/2 \end{pmatrix} = TP^T.$$

SVD confirms that the (non-zero) singular values of $B^T$ are 2, $\sqrt{2}$, and $\sqrt{2}$, the positive square roots of the eigenvalues $\lambda_1=4$, $\lambda_2=2$ and $\lambda_3=2$ of the matrix product $AA^T$. Note that the columns of the Principal Component matrix P (the rows of the Principal Component matrix $P^T$) are the orthonormalized eigenvectors of the matrix product $BB^T$. Also note that the non-zero elements of the Scores matrix T are the positive square roots 2, $\sqrt{2}$, and $\sqrt{2}$ of the (non-zero) eigenvalues $\lambda_1=4$, $\lambda_2=2$ and $\lambda_3=2$ of both of the matrix products $B^T B$ and $BB^T$.

The matrices A and B discussed above have been used for the sake of simplifying the presentation of PCA and the power method, and are much smaller than the data matrices encountered in illustrative embodiments of the present invention. For example, in one illustrative embodiment, for each wafer, 8 scans of OES data over 495 wavelengths may be taken during an etching step, with about a 13 second interval between scans. In this illustrative embodiment, 18 wafers may be run and corresponding OES data collected. The data may be organized as a set of 18×495 matrices $X_s = (X_{ij})_s$, where s=1,2, . . . ,8, for each of the different scans, and $X_{ij}$ is the intensity of the ith wafer run at the jth wavelength. Putting all 8 of the 18×495 matrices $X_s = X_{ij})_s$, for s=1,2, . . . ,8, next to each other produces the overall OES data matrix X, an 18×3960 matrix X=[$X_1, X_2, \ldots, X_8$]= [$(X_{ij})_1, (X_{ij})_2, \ldots, (X_{ij})_8$]. Each row in X represents the OES data from 8 scans over 495 wavelengths for a run. Brute force modeling using all 8 scans and all 495 wavelengths would entail using 3960 input variables to predict the etching behavior of 18 sample wafers, an ill-conditioned regression problem. Techniques such as PCA and/or partial least squares (PLS, also known as projection to latent structures) reduce the complexity in such cases by revealing the hierarchical ordering of the data based on levels of decreasing variability. In PCA, this involves finding successive Principal Components. In PLS techniques such as NIPALS, this involves finding successive latent vectors.

Figure 22:
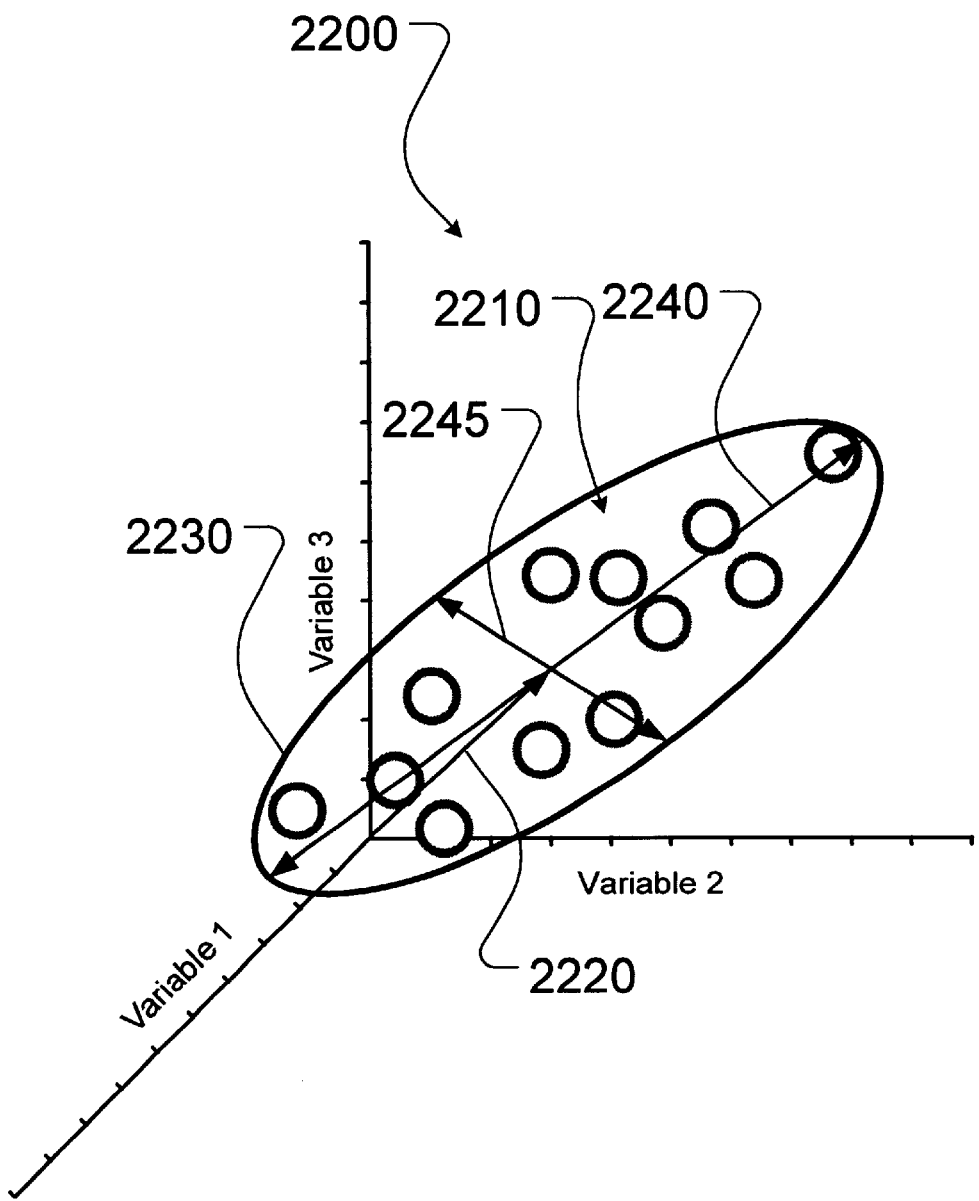
FIGS. 22 and 23 schematically illustrate first and second Principal Components for respective data sets.

As shown in FIG. 22, a scatterplot 2200 of data points 2210 may be plotted in an n-dimensional variable space (n=3 in FIG. 22). The mean vector 2220 may lie at the center of a p-dimensional Principal Component ellipsoid 2230 (p=2 in FIG. 22). The mean vector 2220 may be determined by taking the average of the columns of the overall OES data matrix X. The Principal Component ellipsoid 2230 may have a first Principal Component 2240 (major axis in FIG. 22), with a length equal to the largest eigenvalue of the mean-scaled OES data matrix X–M, and a second Principal Component 2250 (minor axis in FIG. 22), with a length equal to the next largest eigenvalue of the mean-scaled OES data matrix X–M.

Figure 23:
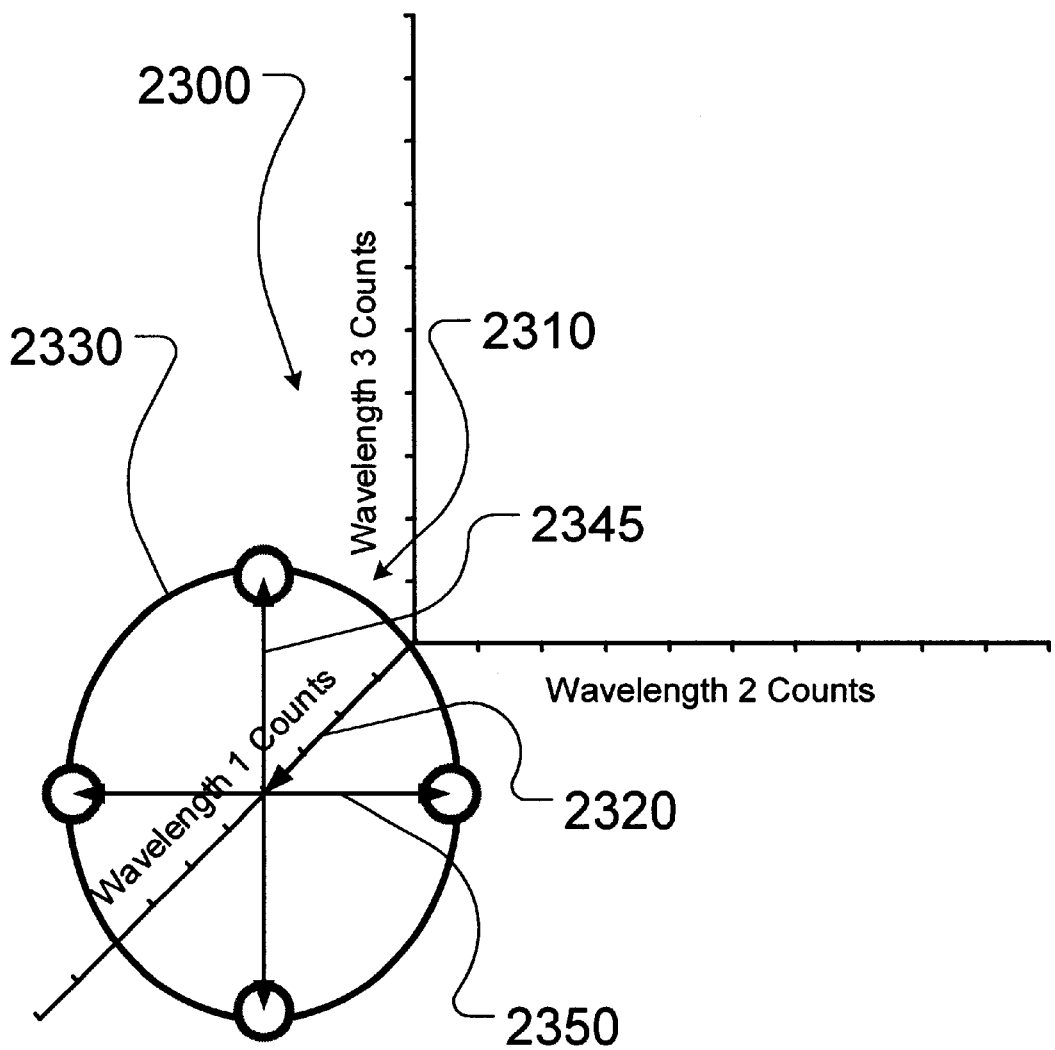

For example, the 3×4 matrix $B^T$ given above may be taken as the overall OES data matrix X (again for the sake of simplicity), corresponding to 4 scans taken at 3 wavelengths. As shown in FIG. 23, a scatterplot 2300 of data points 2310 may be plotted in a 3-dimensional variable space. The mean vector 2320 $\mu$ may lie at the center of a 2-dimensional Principal Component ellipsoid 2330 (really a circle, a degenerate ellipse). The mean vector 2320 $\mu$ may be determined by taking the average of the columns of the overall OES 3×4 data matrix $B^T$. The Principal Component ellipsoid 2330 may have a first Principal Component 2340 ("major" axis in FIG. 23) and a second Principal Component 2350 ("minor" axis in FIG. 23). Here, the eigenvalues of the mean-scaled OES data matrix $B^T$–M are equal and degenerate, so the lengths of the "major" and "minor" axes in FIG. 23 are equal. As shown in FIG. 23, the mean vector 2320 $\mu$ is given by:

$$\mu = \frac{1}{4}\left[\begin{pmatrix}1\\1\\0\end{pmatrix} + \begin{pmatrix}1\\0\\1\end{pmatrix} + \begin{pmatrix}1\\0\\-1\end{pmatrix} + \begin{pmatrix}1\\-1\\0\end{pmatrix}\right] = \begin{pmatrix}1\\0\\0\end{pmatrix},$$

and the matrix M has the mean vector 2320 $\mu$ for all 4 columns.

In another illustrative embodiment, 5500 samples of each wafer may be taken on wavelengths between about 240–1100 nm at a high sample rate of about one per second. For example, 5551 sampling points/spectrum/second (corresponding to 1 scan per wafer per second taken at 5551 wavelengths, or 7 scans per wafer per second taken at 793 wavelengths, or 13 scans per wafer per second taken at 427 wavelengths, or 61 scans per wafer per second taken at 91 wavelengths) may be collected in real time, during etching of a contact hole using an Applied Materials AMAT 5300 Centura etching chamber, to produce high resolution and broad band OES spectra.

Figure 24:
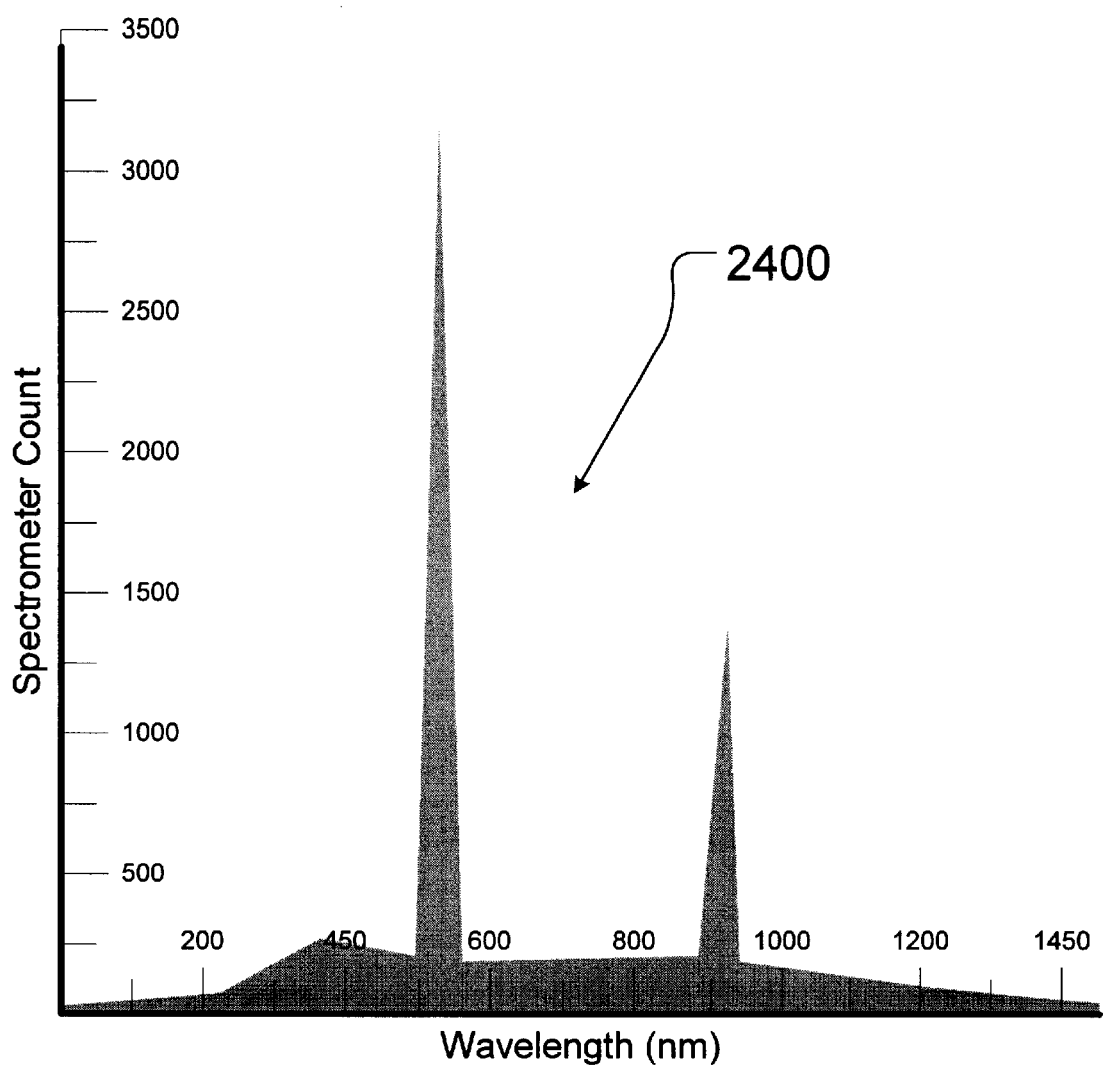
FIG. 24 schematically illustrates OES spectrometer counts plotted against wavelengths.

As shown in FIG. 24, a representative OES spectrum 2400 of a contact hole etch is illustrated. Wavelengths, measured in nanometers (nm) are plotted along the horizontal axis against spectrometer counts plotted along the vertical axis.

Figure 25:
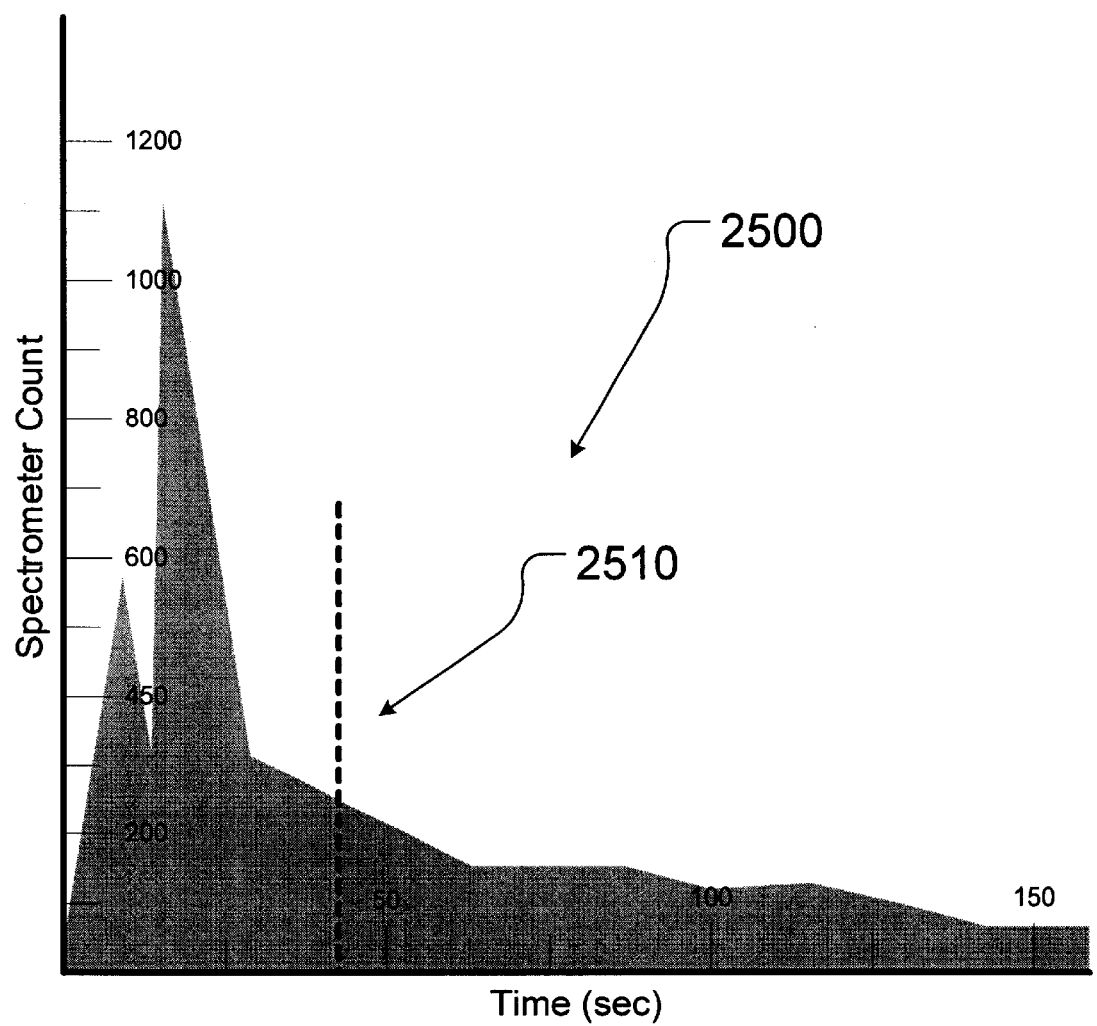
FIG. 25 schematically illustrates a time trace of OES spectrometer counts at a particular wavelength.

As shown in FIG. 25, a representative OES trace 2500 of a contact hole etch is illustrated. Time, measured in seconds (sec) is plotted along the horizontal axis against spectrometer counts plotted along the vertical axis. As shown in FIG. 25, by about 40 seconds into the etching process, as indicated by dashed line 2510, the OES trace 2500 of spectrometer counts "settles down" to a range of values less than or about 300, for example.

Figure 26:
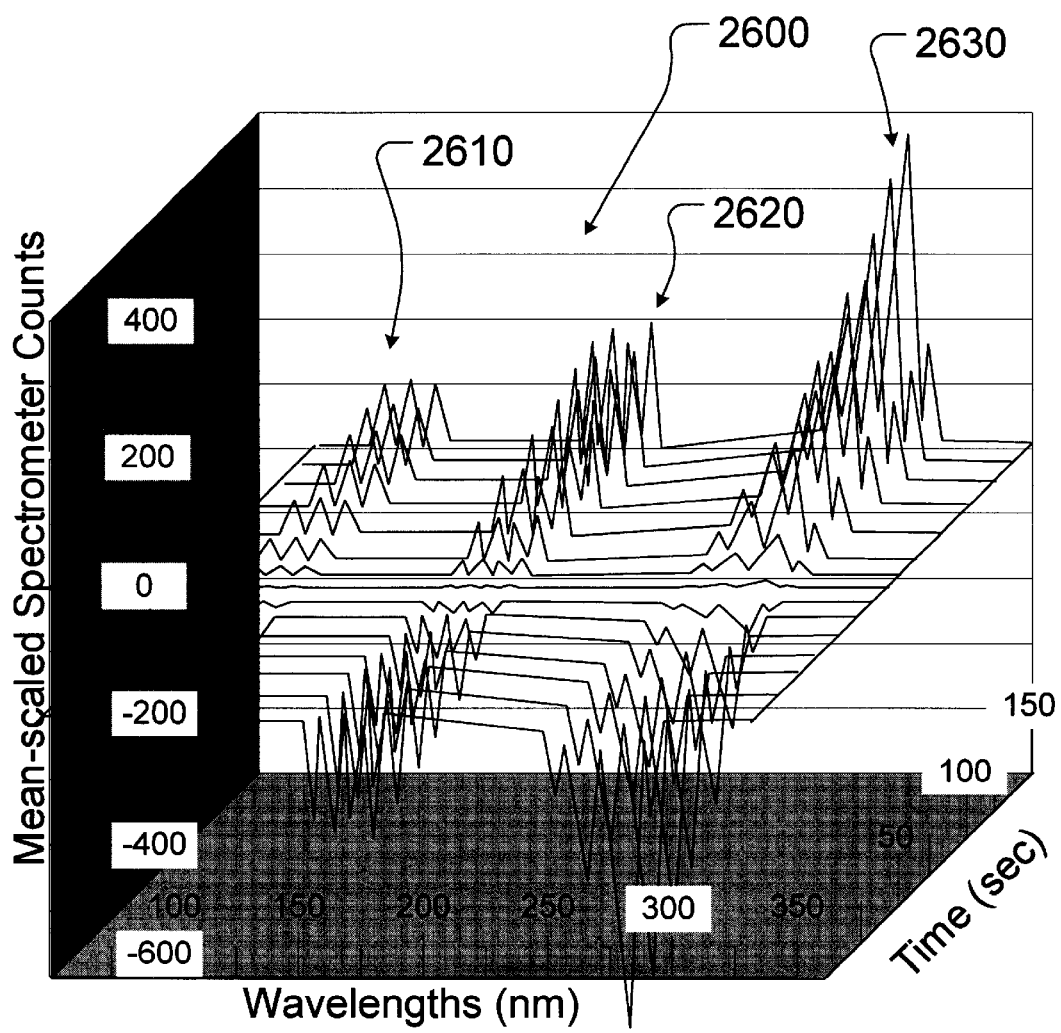
FIG. 26 schematically illustrates representative mean-scaled spectrometer counts for OES traces of a contact hole etch plotted against wavelengths and time.

As shown in FIG. 26, representative OES traces 2600 of a contact hole etch are illustrated. Wavelengths, measured in nanometers (nm) are plotted along a first axis, time, measured in seconds (sec) is plotted along a second axis, and mean-scaled OES spectrometer counts, for example, are plotted along a third (vertical) axis. As shown in FIG. 26, over the course of about 150 seconds of etching, three clusters of wavelengths 2610, 2620 and 2630, respectively, show variations in the respective mean-scaled OES spectrometer counts. In one illustrative embodiment, any one of the three clusters of wavelengths 2610, 2620 and 2630 may be used, either taken alone or taken in any combination with any one (or both) of the others, as an indicator variable signaling an etch endpoint. In an alternative illustrative embodiment, only the two clusters of wavelengths 2620 and 2630 having absolute values of mean-scaled OES spectrometer counts that exceed a preselected threshold absolute mean-scaled OES spectrometer count value (for example, about 200, as shown in FIG. 26) may be used, either taken alone or taken together, as an indicator variable signaling an etch endpoint. In yet another alternative illustrative embodiment, only one cluster of wavelengths 2630 having an absolute value of mean-scaled OES spectrometer counts that exceeds a preselected threshold absolute mean-scaled OES spectrometer count value (for example, about 300, as shown in FIG. 26) may be used as an indicator variable signaling an etch endpoint.

Figure 27:
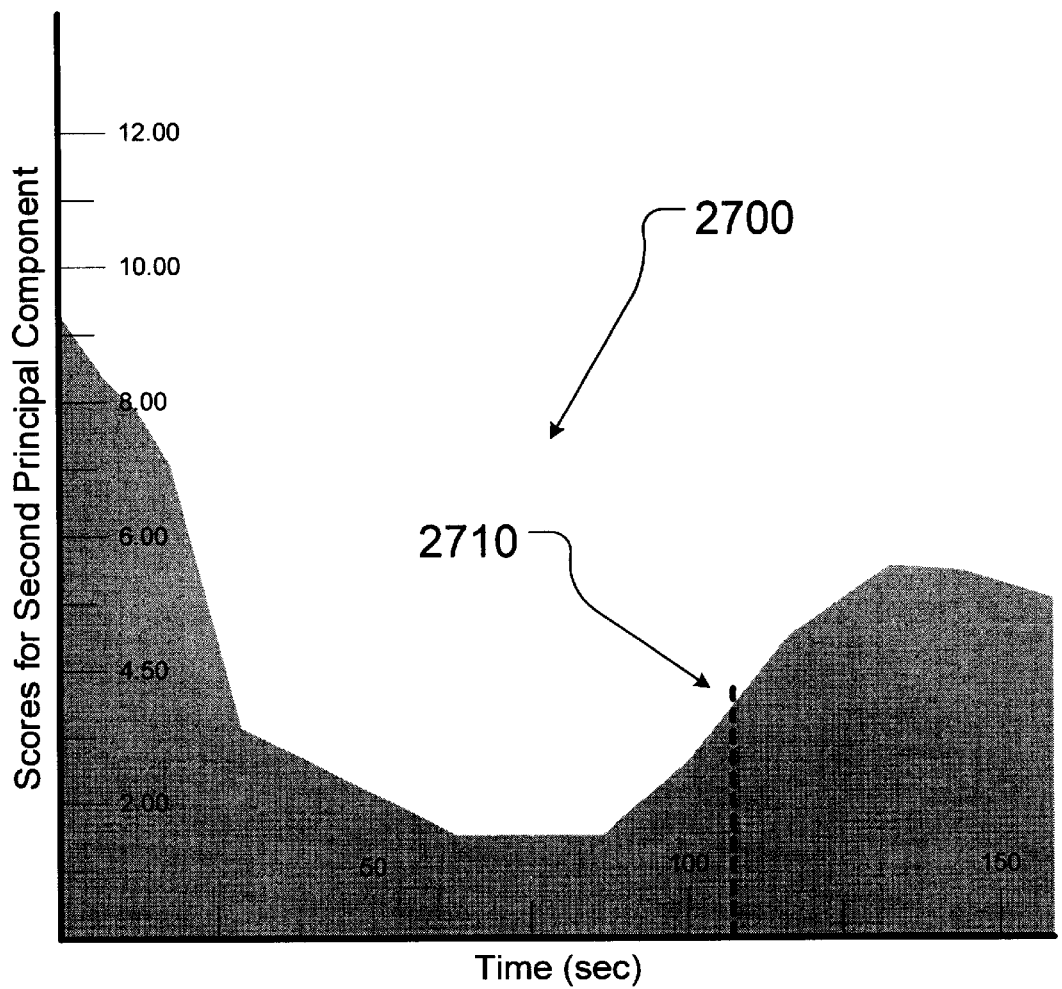
FIG. 27 schematically illustrates a time trace of Scores for the second Principal Component used to determine an etch endpoint.

As shown in FIG. 27, a representative Scores time trace 2700 corresponding to the second Principal Component during a contact hole etch is illustrated. Time, measured in seconds (sec) is plotted along the horizontal axis against Scores (in arbitrary units) plotted along the vertical axis. As shown in FIG. 27, the Scores time trace 2700 corresponding to the second Principal Component during a contact hole etch may start at a relatively high value initially, decrease with time, pass through a minimum value, and then begin increasing before leveling off. We have found that the inflection point (indicated by dashed line 2710, and approximately where the second derivative of the Scores time trace 2700 with respect to time vanishes) is a robust indicator for the etch endpoint.

Figure 28:
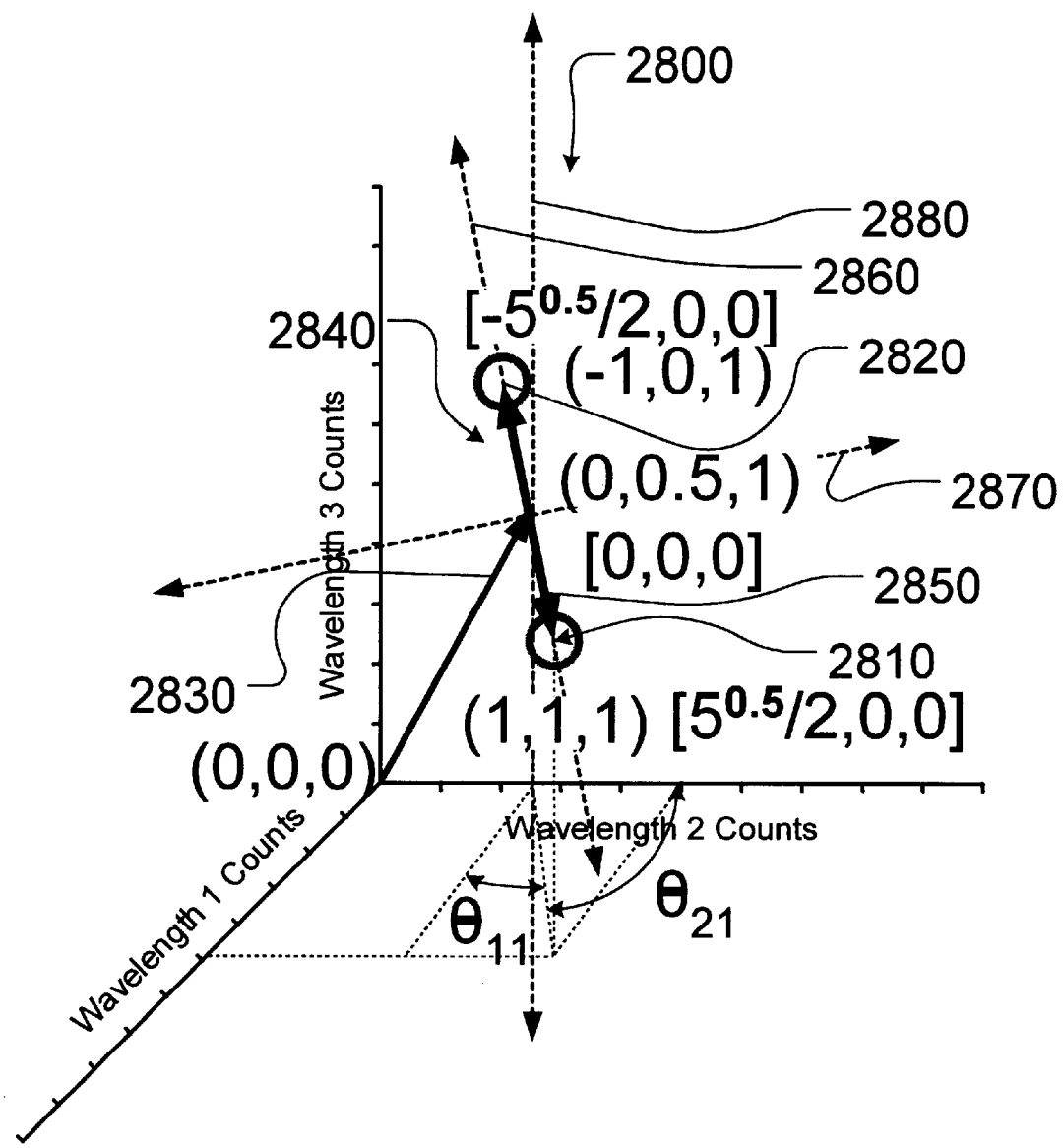
FIGS. 28 and 29 schematically illustrate geometrically Principal Components Analysis for respective data sets.

Principal Components Analysis (PCA) may be illustrated geometrically. For example, the 3×2 matrix C (similar to the 3×2 matrix A given above):

$$C = \begin{pmatrix} 1 & -1 \\ 1 & 0 \\ 1 & 1 \end{pmatrix}$$

may be taken as the overall OES data matrix X (again for the sake of simplicity), corresponding to 2 scans taken at 3 wavelengths. As shown in FIG. 28, a scatterplot 2800 of OES data points 2810 and 2820, with coordinates (1,1,1) and (−1,0,1), respectively, may be plotted in a 3-dimensional variable space where the variables are respective spectrometer counts for each of the 3 wavelengths. The mean vector 2830 $\mu$ may lie at the center of a 1-dimensional Principal Component ellipsoid 2840 (really a line, a very degenerate ellipsoid). The mean vector 2830 $\mu$ may be determined by taking the average of the columns of the overall OES 3×2 matrix C. The Principal Component ellipsoid 2840 may have a first Principal Component 2850 (the "major" axis in FIG. 28, with length √5, lying along a first Principal Component axis 2860) and no second or third Principal Component lying along second or third Principal Component axes 2870 and 2880, respectively. Here, two of the eigenvalues of the mean-scaled OES data matrix C−M are equal to zero, so the lengths of the "minor" axes in FIG. 28 are both equal to zero. As shown in FIG. 28, the mean vector 2830 $\mu$ is given by:

$$\mu = \frac{1}{2}\left[\begin{pmatrix}1\\1\\1\end{pmatrix} + \begin{pmatrix}-1\\0\\1\end{pmatrix}\right] = \begin{pmatrix}0\\1/2\\1\end{pmatrix},$$

and the matrix M has the mean vector 2830 $\mu$ for both columns. As shown in FIG. 28, PCA is nothing more than a principal axis rotation of the original variable axes (here, the OES spectrometer counts for 3 wavelengths) about the endpoint of the mean vector 2830 $\mu$, with coordinates (0,1/2,1) with respect to the original coordinate axes and coordinates [0,0,0] with respect to the new Principal Component axes 2860, 2870 and 2880. The Loadings are merely the direction cosines of the new Principal Component axes 2860, 2870 and 2880 with respect to the original variable axes. The Scores are simply the coordinates of the OES data points 2810 and 2820, [$5^{0.5}/2$,0,0] and [−$5^{0.5}/2$,0,0], respectively, referred to the new Principal Component axes 2860, 2870 and 2880.

The mean-scaled 3×2 OES data matrix C−M, its transpose, the 2×3 matrix $(C-M)^T$, their 2×2 matrix product $(C-M)^T(C-M)$, and their 3×3 matrix product $(C-M)(C-M)^T$ are given by:

$$C-M = \begin{pmatrix}1 & -1\\1 & 0\\1 & 1\end{pmatrix} - \begin{pmatrix}0 & 0\\1/2 & 1/2\\1 & 1\end{pmatrix} = \begin{pmatrix}1 & -1\\1/2 & -1/2\\0 & 0\end{pmatrix}$$

$$(C-M)^T = \begin{pmatrix}1 & 1/2 & 0\\-1 & -1/2 & 0\end{pmatrix}$$

$$(C-M)^T(C-M) = \begin{pmatrix}1 & 1/2 & 0\\-1 & -1/2 & 0\end{pmatrix}\begin{pmatrix}1 & -1\\1/2 & -1/2\\0 & 0\end{pmatrix} = \begin{pmatrix}5/4 & -5/4\\-5/4 & 5/4\end{pmatrix}$$

$$(C-M)(C-M)^T = \begin{pmatrix}1 & -1\\1/2 & -1/2\\0 & 0\end{pmatrix}\begin{pmatrix}1 & 1/2 & 0\\-1 & -1/2 & 0\end{pmatrix} = \begin{pmatrix}2 & 1 & 0\\1 & 1/2 & 0\\0 & 0 & 0\end{pmatrix}$$

The 3×3 matrix $(C-M)(C-M)^T$ is the covariance matrix $S_{3\times 3}$, having elements $S_{ij}$, where i=1,2,3, and j=1,2,3, defined so that:

$$s_{ij} = \frac{2\sum_{k=1}^{2} c_{ik}c_{jk} - \sum_{k=1}^{2} c_{ik}\sum_{k=1}^{2} c_{jk}}{2(2-1)},$$

corresponding to the rectangular 3×2 matrix $C_{3\times 2}$.

BIG reveals that the eigenvalues $\mu$ of the matrix product $(C-M)^T(C-M)$ are 5/2 and 0, for example, by finding solutions to the secular equation:

$$\begin{vmatrix}5/4-\lambda & -5/4\\-5/4 & 5/4-\lambda\end{vmatrix} = 0.$$

The eigenvectors of the matrix product $(C-M)^T(C-M)$ are solutions t of the equation $(C-M)^T(C-M)t=\lambda t$, which may be rewritten as $((C-M)^T(C-M)-\lambda)t=0$. For the eigenvalue $\lambda_1=5/2$, the eigenvector $t_1$ may be seen by $$\begin{pmatrix}5/4-\lambda & -5/4\\-5/4 & 5/4-\lambda\end{pmatrix}t = \begin{pmatrix}-5/4 & -5/4\\-5/4 & -5/4\end{pmatrix}t = 0$$

to be $t_1^T=(1,-1)$. For the eigenvalue $\lambda_1=0$, the eigenvector $t_2$ may be seen by $$\begin{pmatrix}5/4-\lambda & -5/4\\-5/4 & 5/4-\lambda\end{pmatrix}t = \begin{pmatrix}5/4 & -5/4\\-5/4 & 5/4\end{pmatrix}t = 0 \text{ to be } t_2^T=(1,1).$$

The power method, for example, may be used to determine the eigenvalues $\lambda$ and eigenvectors p of the matrix product $(C-M)(C-M)^T$, where the eigenvalues $\lambda$ and the eigenvectors p are solutions p of the equation $((C-M)(C-M)^T)p=\lambda p$. A trial eigenvector $p^T=(1,1,1)$ may be used:

$$((C-M)(C-M)^T)p = \begin{pmatrix}2 & 1 & 0\\1 & 1/2 & 0\\0 & 0 & 0\end{pmatrix}\begin{pmatrix}1\\1\\1\end{pmatrix} = \begin{pmatrix}3\\3/2\\0\end{pmatrix} = 3\begin{pmatrix}1\\1/2\\0\end{pmatrix} = 3q$$

$$((C-M)(C-M)^T)q =$$

$$\begin{pmatrix}2 & 1 & 0\\1 & 1/2 & 0\\0 & 0 & 0\end{pmatrix}\begin{pmatrix}1\\1/2\\0\end{pmatrix} = \begin{pmatrix}5/2\\5/4\\0\end{pmatrix} = 5/2\begin{pmatrix}1\\1/2\\0\end{pmatrix} = \lambda_1 p_1.$$

This illustrates that the trial eigenvector $p^T=(1,1,1)$ gets replaced by the improved trial eigenvector $q^T=(1,1/2,0)$ that happened to correspond to the eigenvector $p_1^T=(1,1/2,0)$ belonging to the eigenvalue $\lambda_1=5/2$. The power method then proceeds by subtracting the outer product matrix $p_1 p_1^T$ from the matrix product $(C-M)(C-M)^T$ to form a residual matrix $R_1 =$ $$\begin{pmatrix}2 & 1 & 0\\1 & 1/2 & 0\\0 & 0 & 0\end{pmatrix} - \begin{pmatrix}1\\1/2\\0\end{pmatrix}(1\ 1/2\ 0) = \begin{pmatrix}2 & 1 & 0\\1 & 1/2 & 0\\0 & 0 & 0\end{pmatrix} - \begin{pmatrix}1 & 1/2 & 0\\1/2 & 1/4 & 0\\0 & 0 & 0\end{pmatrix}$$

$$R_1 = \begin{pmatrix}1 & 1/2 & 0\\1/2 & 1/4 & 0\\0 & 0 & 0\end{pmatrix}.$$

Another trial eigenvector $p^T=(-1,2,0)$, orthogonal to the eigenvector $p_1^T=(1,1/2,0)$ may be used:

$$((C-M)(C-M)^T - \underline{p}_1\underline{p}_1^T)\underline{p} =$$

$$R_1\underline{p} = \begin{pmatrix} 1 & 1/2 & 0 \\ 1/2 & 1/4 & 0 \\ 0 & 0 & 0 \end{pmatrix}\begin{pmatrix} -1 \\ 2 \\ 0 \end{pmatrix} = \begin{pmatrix} 0 \\ 0 \\ 0 \end{pmatrix} = 0\begin{pmatrix} -1 \\ 2 \\ 0 \end{pmatrix} = \lambda_2\underline{p}_2.$$

This indicates that the trial eigenvector $p^T=(-1,2,0)$ happened to correspond to the eigenvector $p_2^T=(-1,2,0)$ belonging to the eigenvalue $\lambda_2=0$. The power method then proceeds by subtracting the outer product matrix $p_2p_2^T$ from the residual matrix $R_1$ to form a second residual matrix $R_2$:

$$R_2 = \begin{pmatrix} 1 & 1/2 & 0 \\ 1/2 & 1/4 & 0 \\ 0 & 0 & 0 \end{pmatrix} - \begin{pmatrix} -1 \\ 2 \\ 0 \end{pmatrix}(-1 \ 2 \ 0) =$$

$$\begin{pmatrix} 1 & 1/2 & 0 \\ 1/2 & 1/4 & 0 \\ 0 & 0 & 0 \end{pmatrix} - \begin{pmatrix} 1 & -2 & 0 \\ -2 & 4 & 0 \\ 0 & 0 & 0 \end{pmatrix}$$

$$R_2 = \begin{pmatrix} 0 & 5/2 & 0 \\ 5/2 & -15/4 & 0 \\ 0 & 0 & 0 \end{pmatrix}.$$

Another trial eigenvector $p^T=(0,0,1)$, orthogonal to the eigenvectors $p_1^T=(1,1/2,0)$ and $p_2^T=(-1,2,0)$ may be used:

$$((C-M)(C-M)^T - \underline{p}_1\underline{p}_1^T - \underline{p}_2\underline{p}_2^T)\underline{p} =$$

$$R_2\underline{p} = \begin{pmatrix} 1 & 5/2 & 0 \\ 5/2 & -15/4 & 0 \\ 0 & 0 & 0 \end{pmatrix}\begin{pmatrix} 0 \\ 0 \\ 1 \end{pmatrix} = \begin{pmatrix} 0 \\ 0 \\ 0 \end{pmatrix}$$

$$((C-M)(C-M)^T - \underline{p}_1\underline{p}_1^T - \underline{p}_2\underline{p}_2^T)\underline{p} = R_2\underline{p} = 0\begin{pmatrix} 0 \\ 0 \\ 1 \end{pmatrix} = \lambda_3\underline{p}_3.$$

This indicates that the trial eigenvector $p^T=(0,0,1)$ happened to correspond to the eigenvector $p_3^T=(0,0,1)$ belonging to the eigenvalue $\lambda_3=0$. Indeed, one may readily verify that:

$$((C-M)(C-M)^T)\underline{p}_3 = \begin{pmatrix} 2 & 1 & 0 \\ 1 & 1/2 & 0 \\ 0 & 0 & 0 \end{pmatrix}\begin{pmatrix} 0 \\ 0 \\ 1 \end{pmatrix} = \begin{pmatrix} 0 \\ 0 \\ 0 \end{pmatrix} = 0\begin{pmatrix} 0 \\ 0 \\ 1 \end{pmatrix} = \lambda_3\underline{p}_3.$$

Similarly, SVD of C−M shows that C−M=$PT^T$, where P is the Principal Component matrix (whose columns are orthonormalized eigenvectors proportional to $p_1$, $p_2$ and $p_3$, and whose elements are the Loadings, the direction cosines of the new Principal Component axes 2860, 2870 and 2880 related to the original variable axes) and T is the Scores matrix (whose rows are the coordinates of the OES data points 2810 and 2820, referred to the new Principal Component axes 2860, 2870 and 2880):

$$C-M = \begin{pmatrix} 2/\sqrt{5} & -1/\sqrt{5} & 0 \\ 1/\sqrt{5} & 2/\sqrt{5} & 0 \\ 0 & 0 & 1 \end{pmatrix}\begin{pmatrix} \sqrt{5}/2 & 0 \\ 0 & 0 \\ 0 & 0 \end{pmatrix}\begin{pmatrix} 1/\sqrt{2} & -1/\sqrt{2} \\ 1/\sqrt{2} & 1/\sqrt{2} \end{pmatrix}$$

-continued $$C-M = \begin{pmatrix} 2/\sqrt{5} & -1/\sqrt{5} & 0 \\ 1/\sqrt{5} & 2/\sqrt{5} & 0 \\ 0 & 0 & 1 \end{pmatrix}\begin{pmatrix} \sqrt{5}/2 & -\sqrt{5}/2 \\ 0 & 0 \\ 0 & 0 \end{pmatrix} = PT^T.$$

The transpose of the Scores matrix ($T^T$) is given by the product of the matrix of eigenvalues of C−M with a matrix whose rows are orthonormalized eigenvectors proportional to $t_1$ and $t_2$. As shown in FIG. 28, the direction cosine (Loading) of the first Principal Component axis 2860 with respect to the wavelength 1 counts axis is given by cos $\Theta_{11}=2/\sqrt{5}$, and the direction cosine (Loading) of the first Principal Component axis 2860 with respect to the wavelength 2 counts axis is given by cos $\Theta_{21}=1/\sqrt{5}$. Similarly, the direction cosine (Loading) of the first Principal Component axis 2860 with respect to the wavelength 3 counts axis is given by cos $\Theta_{31}=\cos(\pi/2)=0$. Similarly, the direction cosine (Loading) of the second Principal Component axis 2870 with respect to the wavelength 1 counts axis is given by cos $\Theta_{12}=-1/\sqrt{5}$, the direction cosine (Loading) of the second Principal Component axis 2870 with respect to the wavelength 2 counts axis is given by cos $\Theta_{22}=2/\sqrt{5}$, and the direction cosine (Loading) of the second Principal Component axis 2870 with respect to the wavelength 3 counts axis is given by cos $\Theta_{32}=\cos(\pi/2)=0$. Lastly, the direction cosine (Loading) of the third Principal Component axis 2880 with respect to the wavelength 1 counts axis is given by cos $\Theta_{13}=\cos(\pi/2)=0$, the direction cosine (Loading) of the third Principal Component axis 2880 with respect to the wavelength 2 counts axis is given by cos $\Theta_{23}=\cos(\pi/2)=0$, and the direction cosine (Loading) of the third Principal Component axis 2880 with respect to the wavelength 3 counts axis is given by cos $\Theta_{33}=\cos(0)=1$.

SVD confirms that the singular values of C−M are $\sqrt{5}/\sqrt{2}$ and 0, the non-negative square roots of the eigenvalues $\lambda_1=5/2$ and $\lambda_2=0$ of the matrix product $(C-M)^T(C-M)$. Note that the columns of the Principal Component matrix P are the orthonormalized eigenvectors of the matrix product $(C-M)(C-M)^T$.

Figure 29:
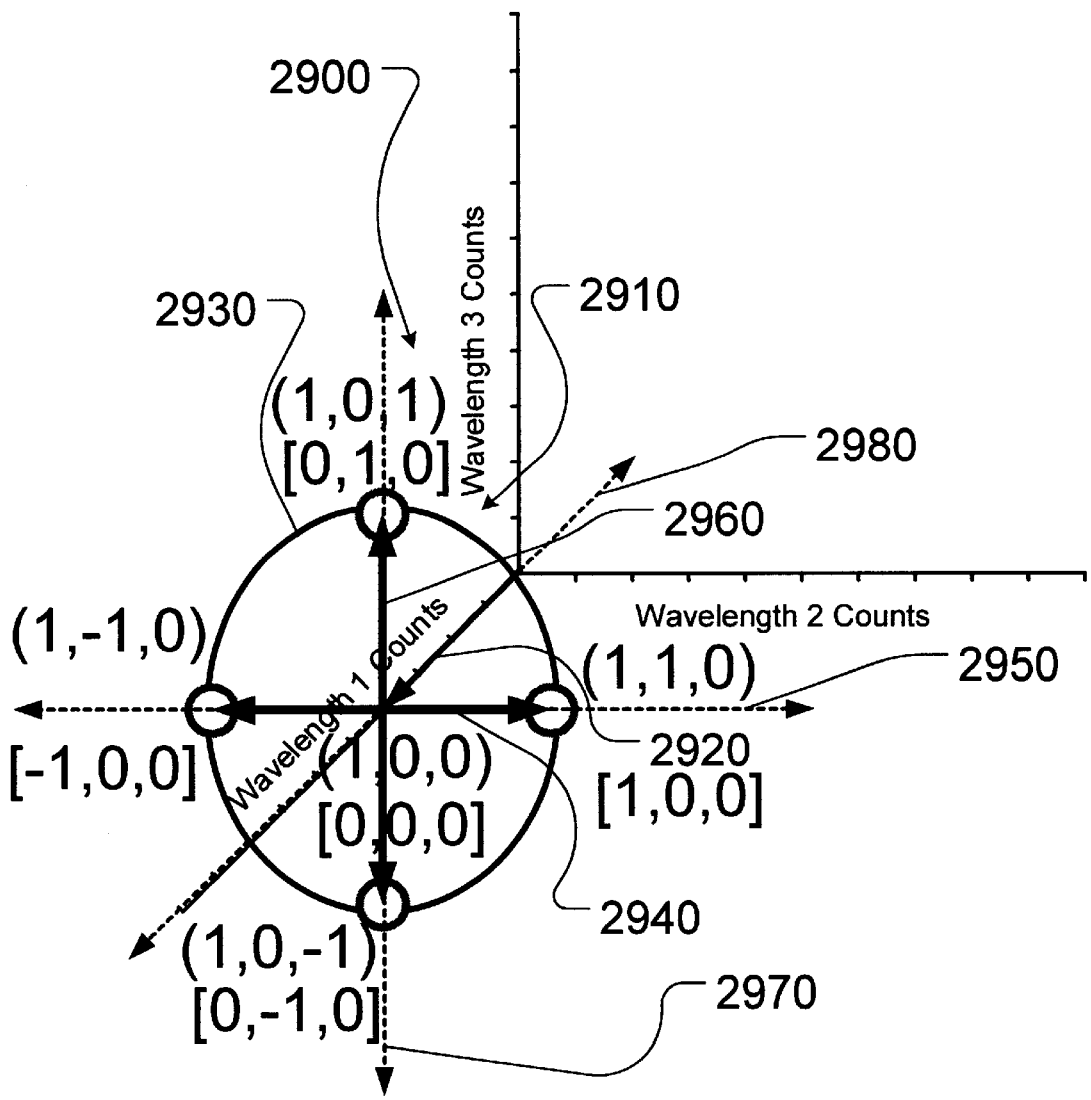

Taking another example, a 3×4 matrix D (identical to the 3×4 matrix $B^T$ given above):

$$D = \begin{pmatrix} 1 & 1 & 1 & 1 \\ 1 & 0 & 0 & -1 \\ 0 & 1 & -1 & 0 \end{pmatrix}$$

may be taken as the overall OES data matrix X (again for the sake of simplicity), corresponding to 4 scans taken at 3 wavelengths. As shown in FIG. 29, a scatterplot 2900 of OES data points with coordinates (1,1,0), (1,0,1), (1,0,−1) and (1,−1,0), respectively, may be plotted in a 3-dimensional variable space where the variables are respective spectrometer counts for each of the 3 wavelengths. The mean vector 2920μ may lie at the center of a 2-dimensional Principal Component ellipsoid 2930 (really a circle, a somewhat degenerate ellipsoid). The mean vector 2920μ may be determined by taking the average of the columns of the overall OES 3×4 matrix D. The Principal Component ellipsoid 2930 may have a first Principal Component 2940 (the "major" axis in FIG. 29, with length 2, lying along a first Principal Component axis 2950), a second Principal Component 2960 (the "minor" axis in FIG. 29, also with length 2, lying along a second Principal Component axis 2970), and no third Principal Component lying along a third Principal Component axis 2980. Here, two of the eigenvalues of the mean-scaled OES data matrix D−M are equal, so the lengths of the "major" and "minor" axes of the Principal Component ellipsoid 2930 in FIG. 29 are both equal, and the remaining eigenvalue is equal to zero, so the length of the other "minor" axis of the Principal Component ellipsoid 2930 in FIG. 29 is equal to zero. As shown in FIG. 29, the mean vector 2920$\mu$ is given by:

$$\mu = \frac{1}{4}\left[\begin{pmatrix}1\\1\\0\end{pmatrix}+\begin{pmatrix}1\\0\\1\end{pmatrix}+\begin{pmatrix}1\\0\\-1\end{pmatrix}+\begin{pmatrix}1\\-1\\0\end{pmatrix}\right]=\begin{pmatrix}1\\0\\0\end{pmatrix}$$

and the matrix M has the mean vector 2920$\mu$ for all 4 columns. As shown in FIG. 29, PCA is nothing more than a principal axis rotation of the original variable axes (here, the OES spectrometer counts for 3 wavelengths) about the endpoint of the mean vector 2920$\mu$, with coordinates (1,0,0) with respect to the original coordinate axes and coordinates [0,0,0] with respect to the new Principal Component axes 2950, 2970 and 2980. The Loadings are merely the direction cosines of the new Principal Component axes 2950, 2970 and 2980 with respect to the original variable axes. The Scores are simply the coordinates of the OES data points, [1,0,0], [0,1,0], [0,−1,0] and [−1,0,0], respectively, referred to the new Principal Component axes 2950, 2970 and 2980.

The 3×3 matrix product $(D-M)(D-M)^T$ is given by:

$$(D-M)(D-M)^T = \begin{pmatrix}0 & 0 & 0 & 0\\1 & 0 & 0 & -1\\0 & 1 & -1 & 0\end{pmatrix}\begin{pmatrix}0 & 1 & 0\\0 & 0 & 1\\0 & 0 & -1\\0 & -1 & 0\end{pmatrix} = \begin{pmatrix}0 & 0 & 0\\0 & 2 & 0\\0 & 0 & 2\end{pmatrix}.$$

The 3×3 matrix (D−M)(D−M) is 3 times the covariance matrix $S_{3\times3}$, having elements $s_{ij}$, where i=1,2,3, and j=1,2,3, defined so that:

$$s_{ij} = \frac{4\sum_{k=1}^{4}d_{ik}d_{jk} - \sum_{k=1}^{4}d_{ik}\sum_{k=1}^{4}d_{jk}}{4(4-1)},$$

corresponding to the rectangular 3×4 matrix $D_{3\times4}$.

EIG reveals that the eigenvalues of the matrix product (D−M)(D−M)7 are 0, 2 and 2. The eigenvectors of the matrix product $(D-M)(D-M)^T$ are solutions p of the equation $((D-M)(D-M)^T)p=\lambda p$, and may be seen by inspection to be $p_1^T=(0,1,0)$, $p_2^T=(0,0,1)$, and $p_3^T=(1,0,0)$, belonging to the eigenvalues $\lambda_1=2$, $\lambda_2=2$, and $\lambda_3=0$, respectively (following the convention of placing the largest eigenvalue first).

As may be seen in FIG. 29, the direction cosine (Loading) of the first Principal Component axis 2950 with respect to the wavelength 1 counts axis is given by cos $\Theta_{11}$=cos($\pi$/2)=0, the direction cosine (Loading) of the first Principal Component axis 2970 with respect to the wavelength 2 counts axis is given by cos $\Theta_{21}$=cos(0)=1, and the direction cosine (Loading) of the first Principal Component axis 2860 with respect to the wavelength 3 counts axis is given by cos $\Theta_{31}$=cos($\pi$/2)=0. Similarly, the direction cosine (Loading) of the second Principal Component axis 2970 with respect to the wavelength 1 counts axis is given by cos $\Theta_{12}$=cos($\Theta$/2)=0, the direction cosine (Loading) of the second Principal Component axis 2970 with respect to the wavelength 2 counts axis is given by cos $\Theta_{22}$=cos($\pi$/2)=0, and the direction cosine (Loading) of the second Principal Component axis 2970 with respect to the wavelength 3 counts axis is given by cos $\Theta_{32}$=cos(0)=1. Lastly, the direction cosine (Loading) of the third Principal Component axis 2980 with respect to the wavelength 1 counts axis is given by cos $\Theta_{13}$=cos(0)=1, the direction cosine (Loading) of the third Principal Component axis 2980 with respect to the wavelength 2 counts axis is given by cos $\Theta_{23}$=cos($\pi$/2)=0, and the direction cosine (Loading) of the third Principal Component axis 2980 with respect to the wavelength 3 counts axis is given by cos $\Theta_{33}$=cos($\pi$/2)=0.

The transpose of the Scores matrix $T^T$ may be obtained simply by multiplying the mean-scaled OES data matrix D−M on the left by the transpose of the Principal Component matrix P, whose columns are $p_1$, $p_2$, $p_3$, the orthonormalized eigenvectors of the matrix product $(D-M)(D-M)^T$:

$$T^T = P^T(D-M) = \begin{pmatrix}0 & 1 & 0\\0 & 0 & 1\\1 & 0 & 0\end{pmatrix}\begin{pmatrix}0 & 0 & 0 & 0\\1 & 0 & 0 & -1\\0 & 1 & -1 & 0\end{pmatrix} = \begin{pmatrix}1 & 0 & 0 & -1\\0 & 1 & -1 & 0\\0 & 0 & 0 & 0\end{pmatrix}.$$

The columns of the transpose of the Scores matrix $T^T$ (or, equivalently, the rows of the Scores matrix T) are, indeed, the coordinates of the OES data points, [1,0,0], [0,1,0], [0,−1,0] and [−1,0,0], respectively, referred to the new Principal Component axes 2950, 2970 and 2980.

We have found that the second Principal Component contains a very robust, high signal-to-noise indicator for etch endpoint determination. The overall mean-scaled OES rectangular n×m data matrix $X_{nm}-M_{nm}$ may be decomposed into a portion corresponding to the first and second Principal Components and respective Loadings and Scores, and a residual portion:

$$X - M = P_{PC}T_{PC}^T + P_{res}T_{res}^T = (p_1 \quad p_2)\begin{pmatrix}t_1^T\\t_2^T\end{pmatrix} + P_{res}T_{res}^T$$

$$X - M = p_1 t_1^T + p_2 t_2^T + P_{res}T_{res}^T = X_{PC} + X_{res},$$

where $P_{PC}$ is an n×2 matrix whose columns are the first and second Principal Components, $T_{PC}$ is an m×2 Scores matrix for the first and second Principal Components, $T_{PC}^T$ is a 2×m Scores matrix transpose, $P_{PC}T_{PC}^T=X^{PC}$ is an n×m matrix, $P_{res}$ is an n×(m−2) matrix whose columns are the residual Principal Components, $T_{res}$ is an m×(m−2) Scores matrix for the residual Principal Components, $T_{res}^T$ is an (m−2)×m Scores matrix transpose, and $P_{res}T_{res}^T=X_{res}$ is an n×m matrix. The kth column of X−M, $x_k$, k=1,2, . . . ,m, an n×1 matrix, similarly decomposes into $x_k=(x_{PC})_k+(x_{res})k$, where $(x_{PC})_k=P_{PC}P_{PC}^T x_k$ is the projection of $x_k$ into the Principal Component subspace (PCS) spanned by the first and second Principal Components, $(x_{res})_k=(I_{n\times n}-P_{PC}P_{PC}^T)x_k$ is the projection of $x_k$ into the residual subspace orthogonal to the PCS spanned by the first and second Principal Components, $(x_{PC})_k^T=x_k^T P_{PC}P_{PC}^T$ is the projection of $x_k^T$ into the Principal Component subspace (PCS) spanned by the first and second Principal Components, $(x_{res})_k^T=x_k^T(I_{n\times n}-P_{PC}P_{PC}^T)$ is the projection of $x_k^T$ into the residual subspace orthogonal to the PCS spanned by the first and second Principal Components, and $I_{n\times n}$ is the n×n identity matrix.

Using the projection of $x_k$ into the PCS spanned by the first and second Principal Components and the projection of $x_k$ into the residual subspace orthogonal to the PCS spanned by the first and second Principal Components, there are two tests of the amount of variance in the data that are accounted for by the first and second Principal Components. One test is the Q-test, also known as the Squared Prediction Error (SPE) test, where $SPE=\|(I_{n\times n}-P_{PC}P_{PC}^T)x_k\|^2=\|(x_{res})_k\|^2 \leq \delta_\alpha^2$. Another test is the Hotelling $T^2$ test, a multivariate generalization of the well-known Student's t-test, where $T^2=x_k^T P_{PC} \Lambda^{-2} P_{PC}^T x_k = x_k^T P_{PC} P_{PC}^T \Lambda^{-2} P_{PC} P_{PC}^T x_k = (x_{PC})_k^T \Lambda^{-2}(x_{PC})_k \leq \chi_\alpha^2$, where $\Lambda^2$ is a 2×2 diagonal matrix of the squares of the eigenvalues $\lambda_i$, i=1,2, belonging to the first and second Principal Components of the overall mean-scaled OES rectangular n×m data matrix $X_{nm}-M_{nm}$. Both the SPE test and the Hotelling $T^2$ test can be used to monitor the etching process, for example.

We have also found that the first through fourth Principal Components are similarly useful for containing high signal-to-noise indicators for etch endpoint determination as well as being useful for OES data compression. The overall mean-scaled OES rectangular n×m data matrix $X_{nm}-M_{nm}$ may be decomposed into a portion corresponding to the first through fourth Principal Components and respective Loadings and Scores, and a residual portion:

$$X - M = P_{PC}T_{PC}^T + P_{res}T_{res}^T = (p_1 \quad p_2 \quad p_3 \quad p_4) \begin{pmatrix} t_1^T \\ t_2^T \\ t_3^T \\ t_4^T \end{pmatrix} + P_{res}T_{res}^T$$

which expands out to $X-M=p_1 t_1^T + p_2 t_2^T + p_3 t_3^T + p_4 t_4^T + P_{res}T_{res}^T = X_{PC} + X_{res}$, where $P_{PC}$ is an n×4 matrix whose columns are the first through fourth Principal Components, $T_{PC}$ is an m×4 Scores matrix for the first through fourth Principal Components, $T_{PC}^T$ is a 4×m Scores matrix transpose, $P_{PC}T_{PC}^T = X_{PC}$ is an n×m matrix, $P_{res}$ is an n×(m−4) matrix whose columns are the residual Principal Components, $T_{res}$ is an m×(m−4) Scores matrix for the residual Principal Components, $T_{res}^T$ is a (m−4)×m Scores matrix transpose, and $P_{res}T_{res}^T = X_{res}$ is an n×m matrix. The kth column of X−M, $x_k$, k=1,2, ... ,m, an n×1 matrix, similarly decomposes into $x_k=(x_{PC})_k+(x_{res})_k$, where $(x_{PC})_k = P_{PC}P_{PC}^T x_k$ is the projection of $x_k$ into the Principal Component subspace (PCS) spanned by the first through fourth Principal Components, $(x_{res})_k=(I_{n\times n}-P_{PC}P_{PC}^T)x_k$ is the projection of $x_k$ into the residual subspace orthogonal to the PCS spanned by the first through fourth Principal Components, $(x_{PC})_k^T = x_k^T P_{PC}P_{PC}^T$ is the projection of $x_k^T$ into the Principal Component subspace (PCS) spanned by the first through fourth Principal Components, $(x_{res})_k^T = x_k^T(I_{n\times n}-P_{PC}P_{PC}^T)$ is the projection of $x_k^T$ into the residual subspace orthogonal to the PCS spanned by the first through fourth Principal Components, and $I_{n\times n}$ is the n×n identity matrix.

Using the projection of $x_k$ into the PCS spanned by the first through fourth Principal Components and the projection of $x_k$ into the residual subspace orthogonal to the PCS spanned by the first through fourth Principal Components, there are again two tests of the amount of variance in the data that are accounted for by the first through fourth Principal Components. One test is the Q-test, also known as the Squared Prediction Error (SPE) test, where $SPE=\|(I_{n\times n}-P_{PC}P_{PC}^T)x_k\|^2=\|(x_{res})_k\|^2 \leq \delta_\alpha^2$. Another test is the Hotelling $T^2$ test, a multivariate generalization of the well-known Student's t-test, where $T^2=x_k^T P_{PC} \Lambda^{-2} P_{PC}^T x_k = x_k^T P_{PC} P_{PC}^T \Lambda^{-2} P_{PC} P_{PC}^T x_k = (x_{PC})_k^T \Lambda^{-2}(x_{PC})_k \leq \chi_\alpha^2$, where $\Lambda^2$ is a 4×4 diagonal matrix of the squares of the eigenvalues $\lambda_i$, i=1,2,3,4 belonging to the first through fourth Principal Components of the overall mean-scaled OES rectangular n×m data matrix $X_{nm}-M_{nm}$.

More generally, the overall mean-scaled OES rectangular n×m data matrix $X_{nm}-M_{nm}$ of rank r, where $r \leq \min\{m,n\}$, may be decomposed into a portion corresponding to the first through rth Principal Components and respective Scores, and a residual portion:

$$X - M = P_{PC}T_{PC}^T + P_{res}T_{res}^T = (p_1 \quad p_2 \quad \cdots \quad p_{r-1} \quad p_r) \begin{pmatrix} t_1^T \\ t_2^T \\ \vdots \\ t_{r-1}^T \\ t_r^T \end{pmatrix} + P_{res}T_{res}^T$$

which expands out to $X-M=p_1 t_1^T + p_2 t_2^T + \cdots + p_{r-1} t_{r-1}^T + p_r t_r^T + P_{res}T_{res}^T = X_{PC} + X_{res}$, where $P_{PC}$ is an n×r matrix whose columns are the first through rth Principal Components, $T_{PC}$ is an m×r Scores matrix for the first through rth Principal Components, $T_{PC}^T$ is an r×m Scores matrix transpose, $P_{PC}T_{PC}^T = X_{PC}$ is an n×m matrix, $P_{res}$ is an n×(m−r) matrix whose columns are the residual Principal Components (if m=r, $P_{res}$=0), $T_{res}$ is an m×(m−r) Scores matrix for the residual Principal Components (if m=r, $T_{res}$=0), $T_{res}^T$ is an (m−r)×m Scores matrix transpose (if m=r, $T_{res}^T$=0), and $T_{res}P_{res}^T = X_{res}$ is an n×m matrix (if m=r, $X_{res}$=0). The kth column of X−M, $x_k$, k=1,2, ... ,m, an n×1 matrix, similarly decomposes into $x_k=(x_{PC})_k+(x_{res})_k$, where $(x_{PC})_k = P_{PC}P_{PC}^T x_k$ is the projection of $x_k$ into the Principal Component subspace (PCS) spanned by the first through rth Principal Components, $(x_{res})_k=(I_{n\times n}-P_{PC}P_{PC}^T)x_k$ is the projection of $x_k$ into the residual subspace orthogonal to the PCS spanned by the first through rth Principal Components, $(x_{PC})_k^T = x_k^T P_{PC}P_{PC}^T$ is the projection of $x_k^T$ into the Principal Component subspace (PCS) spanned by the first through rth Principal Components, $(x_{res})_k^T = x_k^T(I_{n\times n}-P_{PC}P_{PC}^T)$ is the projection of $x_k^T$ into the residual subspace orthogonal to the PCS spanned by the first through rth Principal Components, and $I_{n\times n}$ is the n×n identity matrix.

Using the projection of $x_k$ into the PCS spanned by the first through rth Principal Components and the projection of $x_k$ into the residual subspace orthogonal to the PCS spanned by the first through rth Principal Components, there are likewise two tests of the amount of variance in the data that are accounted for by the first through rth Principal Components. One test is the Q-test, also known as the Squared Prediction Error (SPE) test, where $SPE=\|(I_{n\times n}-P_{PC}P_{PC}^T)x_k\|^2=\|(x_{res})_k\|^2 \leq \delta_\alpha^2$. Another test is the Hotelling $T^2$ test, a multivariate generalization of the well-known Student's t-test, where $T^2=x_k^T P_{PC} \Lambda^{-2} P_{PC}^T x_k = x_k^T P_{PC} P_{PC}^T \Lambda^{-2} P_{PC} P_{PC}^T x_k = (x_{PC})_k^T \Lambda^{-2}(x_{PC})_k \leq \chi_\alpha^2$, where $\Lambda^2$ is an r×r diagonal matrix of the squares of the eigenvalues $\lambda_i$, i=1,2, ... ,r belonging to the first through rth Principal Components of the overall mean-scaled OES rectangular n×m data matrix $X_{nm}-M_{nm}$ of rank r, where $r \leq \min\{m,n\}$.

In one illustrative embodiment of a method according to the present invention, as shown in FIGS. 1–7, archived data sets of OES wavelengths (or frequencies), from wafers that had previously been plasma etched, may be processed and the weighted linear combination of the intensity data, representative of OES wavelengths (or frequencies) collected over time during the plasma etch, defined by the second Principal Component may be used to determine an etch endpoint.

As shown in FIG. 1, a workpiece 100, such as a semiconducting substrate or wafer, having one or more process layers and/or semiconductor devices such as an MOS transistor disposed thereon, for example, is delivered to an etching preprocessing step j 105, where j may have any value from j=1 to j=N−1. The total number N of processing steps, such as masking, etching, depositing material and the like, used to form the finished workpiece 100, may range from N=1 to about any finite value.

Figure 2:
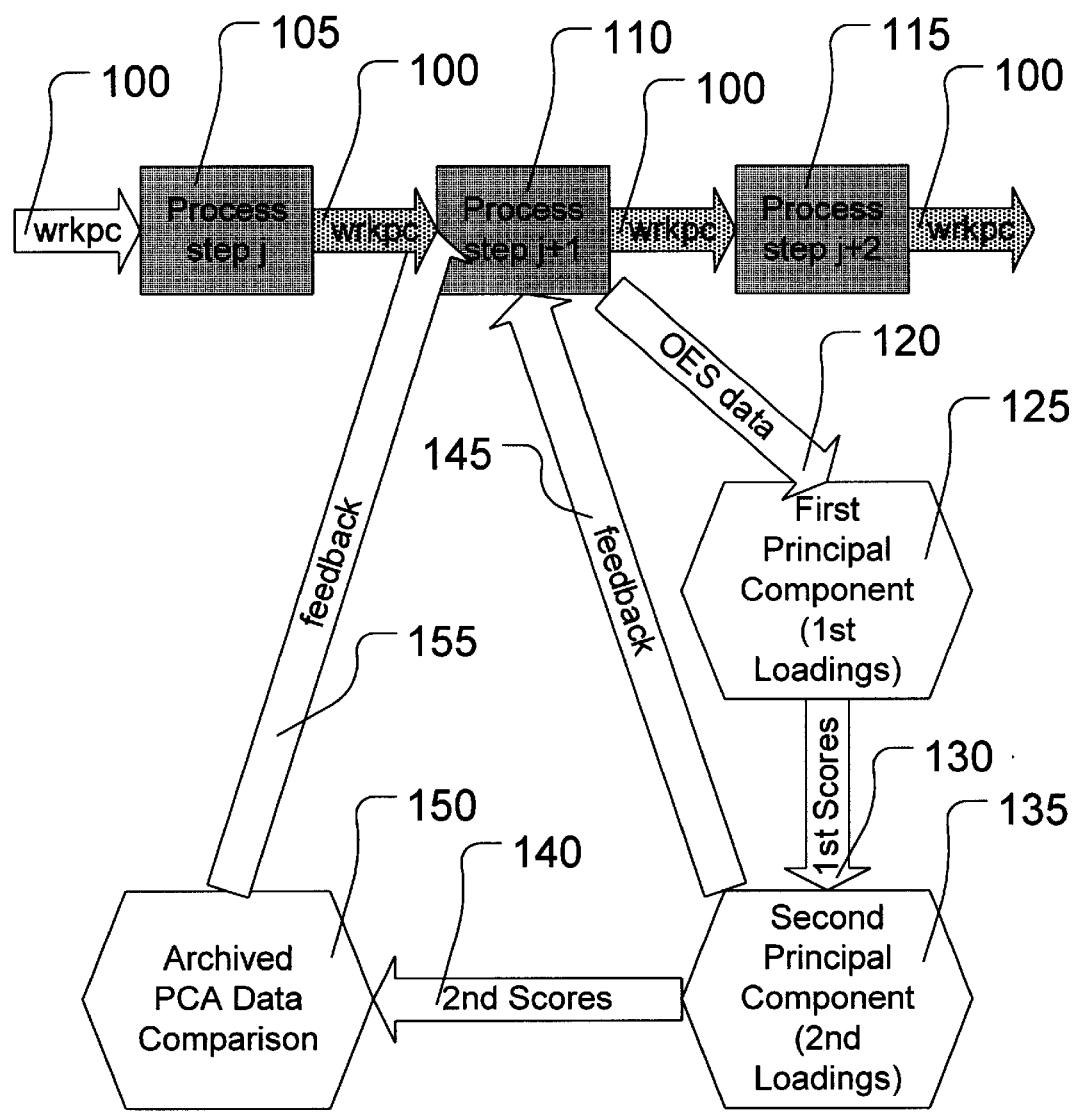

As shown in FIG. 2, the workpiece 100 is sent from the etching preprocessing step j 105 to an etching step j+1 110. In the etching step j+1 110, the workpiece 100 is etched to remove selected portions from one or more process layers formed in any of the previous processing steps (such as etching preprocessing step j 105, where j may have any value from j=1 to j=N−1). As shown in FIG. 2, if there is further processing to do on the workpiece 100 (if j<N−1), then the workpiece 100 may be sent from the etching step j+1 110 and delivered to a postetching processing step j+2 115 for further postetch processing, and then sent on from the postetching processing step j+2 115. Alternatively, the etching step j+1 110 may be the final step in the processing of the workpiece 100. In the etching step j+1 110, OES spectra are measured in situ by an OES spectrometer (not shown), producing OES data 120 indicative of the state of the workpiece 100 during the etching.

In one illustrative embodiment, 5500 samples of each wafer may be taken on wavelengths between about 240–1100 nm at a high sample rate of about one per second. For example, 5551 sampling points/spectrum/second (corresponding to 1 scan per wafer per second taken at 5551 wavelengths) may be collected in real time, during etching of a contact hole using an Applied Materials AMAT 5300 Centura etching chamber, to produce high resolution and broad band OES spectra.

Figure 3:
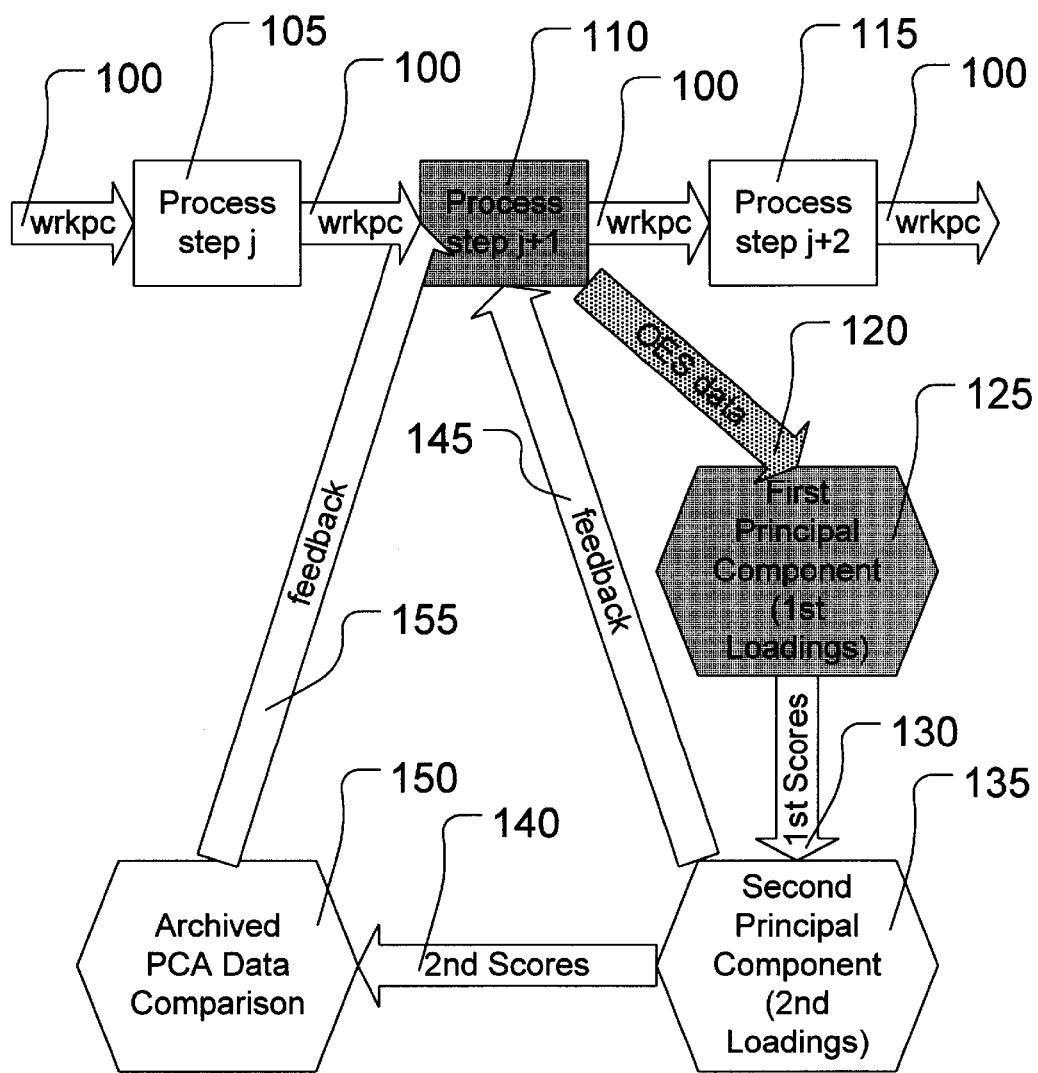

As shown in FIG. 3, the OES data 120 is sent from the etching step j+1 110 and delivered to a first Principal Component (1st Factor) determination step 125. In the first Principal Component (1st Factor) determination step 125, the first Principal Component (1st Factor) and 1st Scores, corresponding to the first Principal Component (1st Factor), may be determined from the OES data 120, for example, by any of the techniques discussed above, producing the 1st Scores signal 130.

Figure 4:
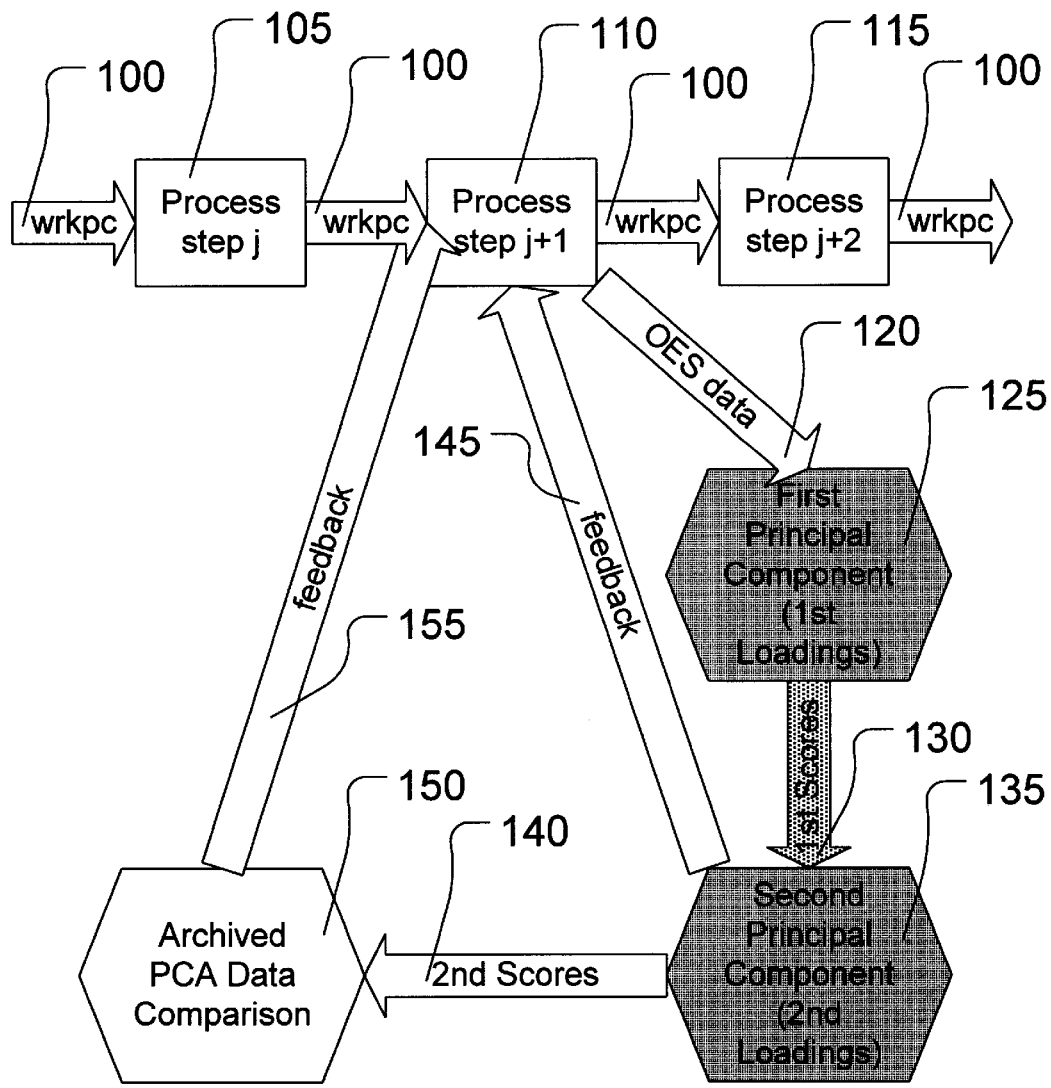

As shown in FIG. 4, the 1st Scores signal 130 is gent from the first Principal Component (1st Loadings) determination step 125 to a second Principal Component (2nd Loadings) determination step 135. In the second Principal Component (2nd Loadings) determination step 135, the second Principal Component (2nd Loadings) and 2nd Scores, corresponding to the second Principal Component (2nd Loadings), may be determined from the OES data 120 and the 1st Scores signal 130, for example, by any of the techniques discussed above, producing the 2nd Scores signal 140.

Figure 5:
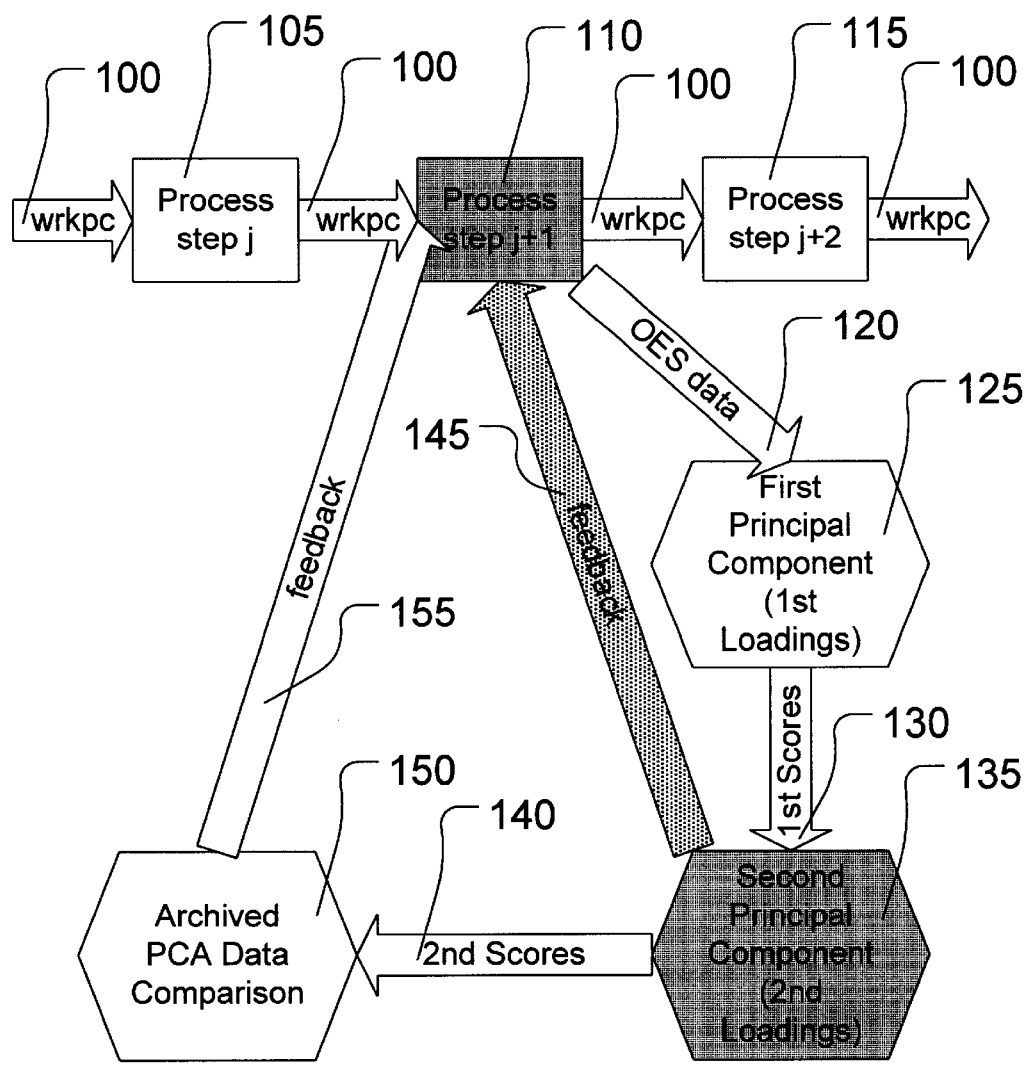

As shown in FIG. 5, a feedback control signal 145 may be sent from the second Principal Component (2nd Loadings) determination step 135 to the etching step j+1 110 to adjust the processing performed in the etching step j+1 110. For example, based on the determination of the first and second Principal Components (1st and 2nd Loadings), and the 1st and 2nd Scores corresponding to the first and second Principal Components (1st and 2nd Loadings), the feedback control signal 145 may be used to signal the etch endpoint.

Figure 6:
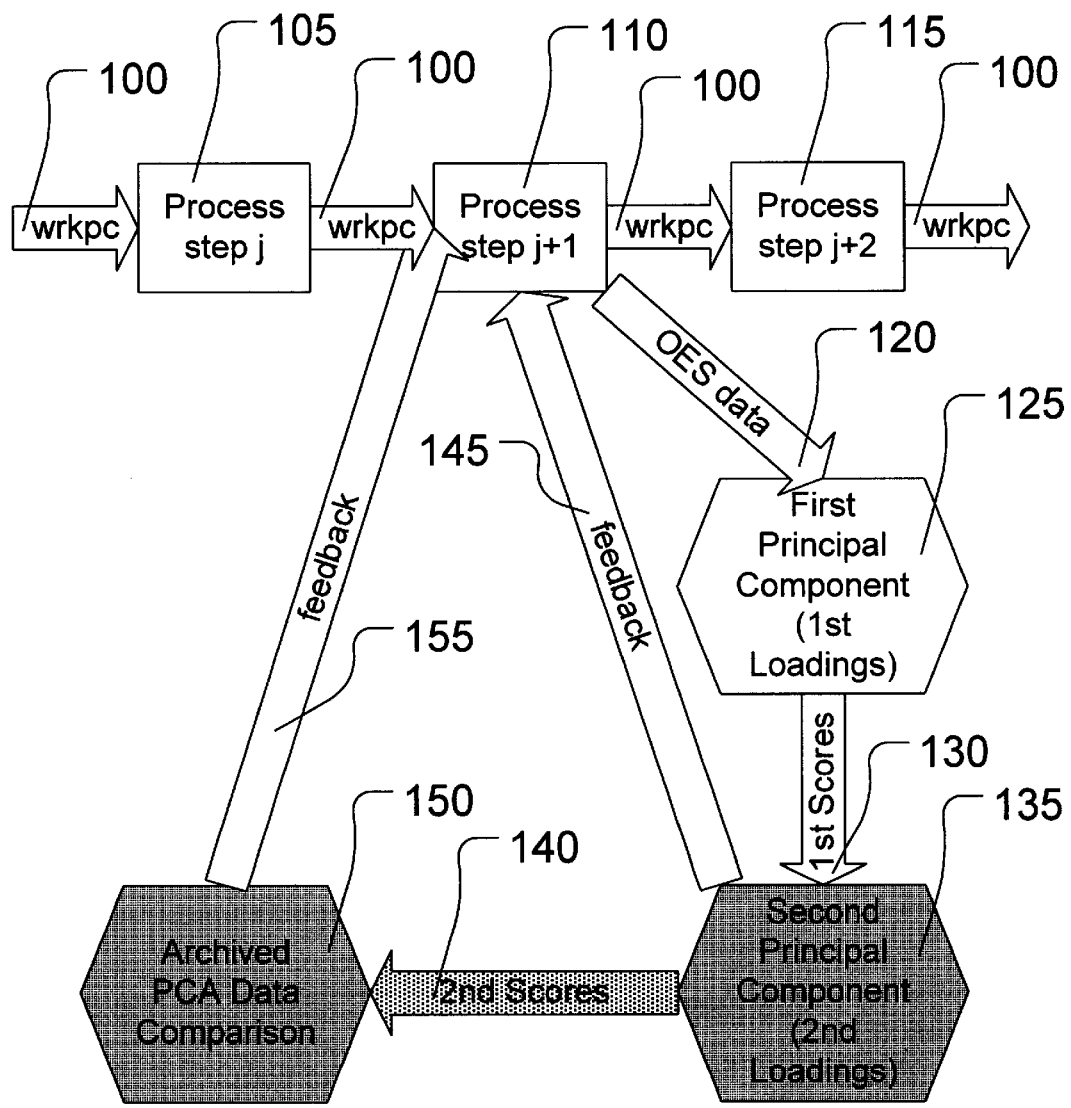

As shown in FIG. 6, in addition to, and/or instead of, the feedback control signal 135, the 2nd Scores signal 140 may be sent from the second Principal Component (2nd Loadings) determination step 135 and may then be delivered to an archived PCA data comparison step 150. In the archived PCA data comparison step 150, archived data sets of OES wavelengths (or frequencies), from wafers that had previously been plasma etched, may be compared with the OES data 120 measured in situ in the etching step 110, and the comparison may be used to determine an etch endpoint.

In particular, first and second Principal Components (1st and 2nd Loadings), and the 1st and 2nd Scores corresponding to the first and second Principal Components (1st and 2nd Loadings), previously determined from the archived data sets of OES wavelengths (or frequencies), may be compared with the first and second Principal Components (1st and 2nd Loadings), and the 1st and 2nd Scores corresponding to the first and second Principal Components (1st and 2nd Loadings), determined in the first Principal Component (1st Loadings) determination step 125 and the second Principal Component (2nd Loadings) determination step 135. This comparison of the respective PCA information may be used to determine an etch endpoint.

For example, PCA may be applied to the archived OES data and the respective Loadings for the first two Principal Components may be retained as model information. When new OES data are taken during an etch process, approximations to the first two Scores for the new OES data are calculated by using the respective Loadings for the first two Principal Components retained from the model information derived from the archived OES data. The approximations to the second Score (corresponding to the second Principal Component) may be used to determine the etch endpoint, by plotting the approximation to the second Score as a time trace and looking for an abrupt change in the value of the approximation to the second Score on the time trace, for example.

Figure 7:
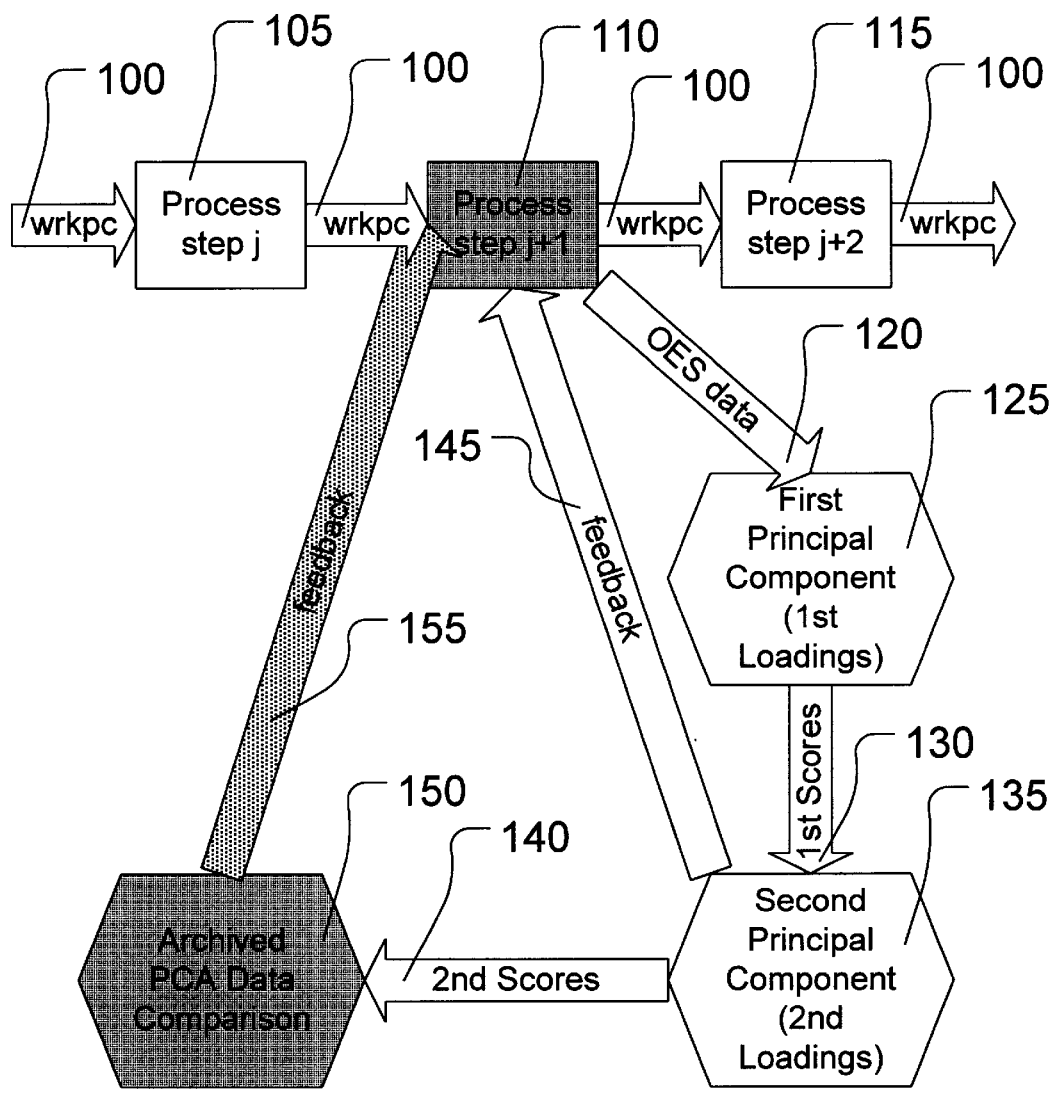

As shown in FIG. 7, a feedback control signal 155 may be sent from the archived PCA data comparison step 150 to the etching step j+1 110 to adjust the processing performed in the etching step j+1 110. For example, based on the determination and comparison of the respective first and second Principal Components (1st and 2nd Loadings), and the 1st and 2nd Scores corresponding to the respective first and second Principal Components (1st and 2nd Loadings), the feedback control signal 155 may be used to signal the etch endpoint.

In another illustrative embodiment of a method according to the present invention, as shown in FIGS. 8–14, only the OES wavelengths (or frequencies) above a certain threshold value in Loading or weighting, as defined by the second Principal Component, may be used to determine an etch endpoint.

Figure 8:
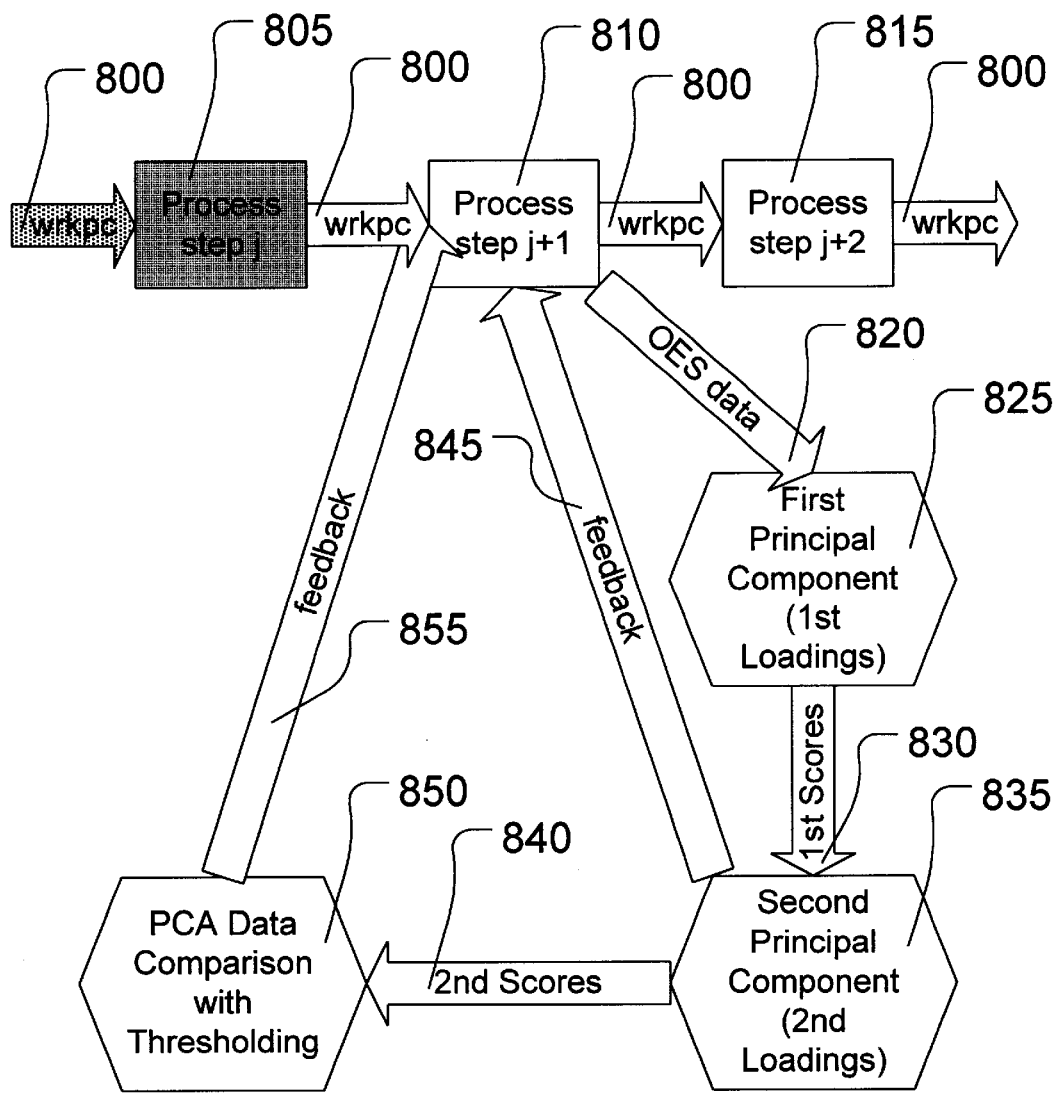
FIGS. 8–14 schematically illustrate a flow diagram for various alternative embodiments of a method according to the present invention.

As shown in FIG. 8, a workpiece 800, such as a semiconducting substrate or wafer, having one or more process layers and/or semiconductor devices such as an MOS transistor disposed thereon, for example, is delivered to an etching preprocessing step j 805, where j may have any value from j=1 to j=N−1. The total number N of processing steps, such as masking, etching, depositing material and the like, used to form the finished workpiece 800, may range from N=1 to about any finite value.

Figure 9:
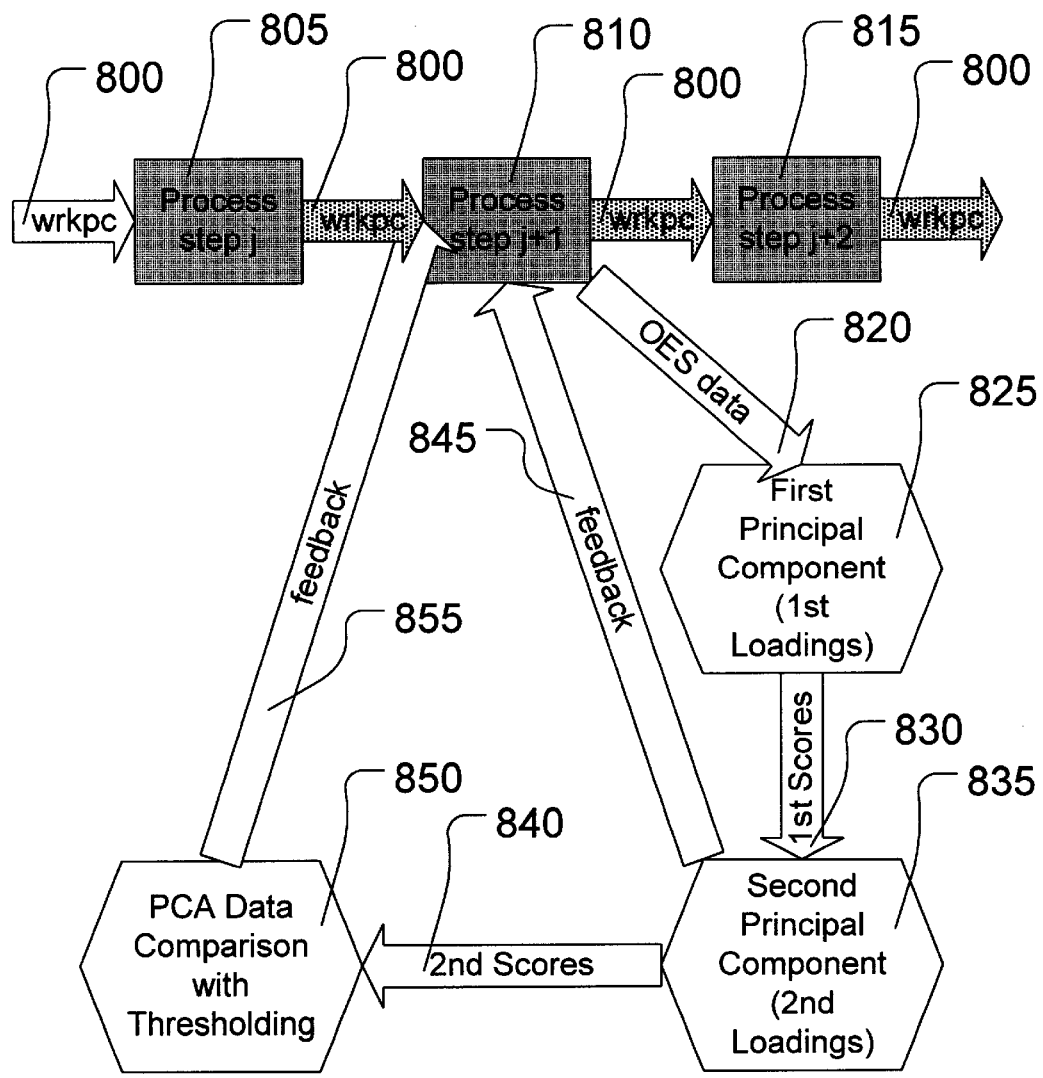

As shown in FIG. 9, the workpiece 800 is sent from the etching preprocessing step j 805 to an etching step j+1 810. In the etching step j+1 810, the workpiece 800 is etched to remove selected portions from one or more process layers formed in any of the previous processing steps (such as etching preprocessing step j 805, where j may have any value from j=1 to j=N−1). As shown in FIG. 9, if there is further processing to do on the workpiece 800 (if j<N−1), then the workpiece 800 may be sent from the etching step j+1 810 and delivered to a postetching processing step j+2 815 for further postetch processing, and then sent on from the postetching processing step j+2 815. Alternatively, the etching step j+1 810 may be the final step in the processing of the workpiece 800. In the etching step j+1 810, OES spectra are measured in situ by an OES spectrometer (not shown), producing OES data 820 indicative of the state of the workpiece 800 during the etching.

Figure 10:
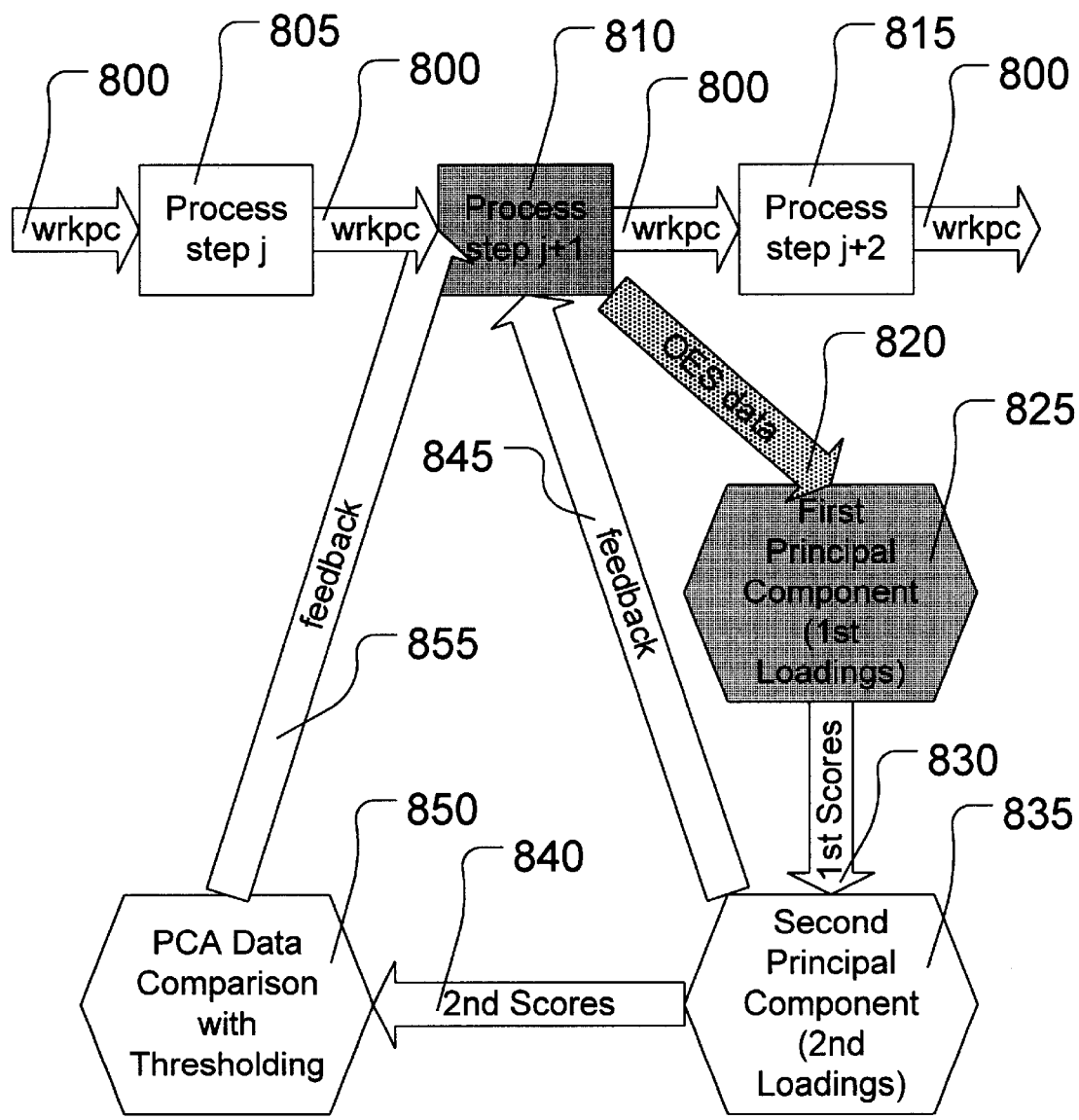

As shown in FIG. 10, the OES data 820 is sent from the etching step j+1 810 and delivered to a first Principal Component (1st Loadings) determination step 825. In the first Principal Component (1st Loadings) determination step 825, the first Principal Component (1st Loadings) and 1st Scores, corresponding to the first Principal Component (1st Loadings), may be determined from the OES data 820, for example, by any of the techniques discussed above, producing the 1st Scores signal 830.

Figure 11:
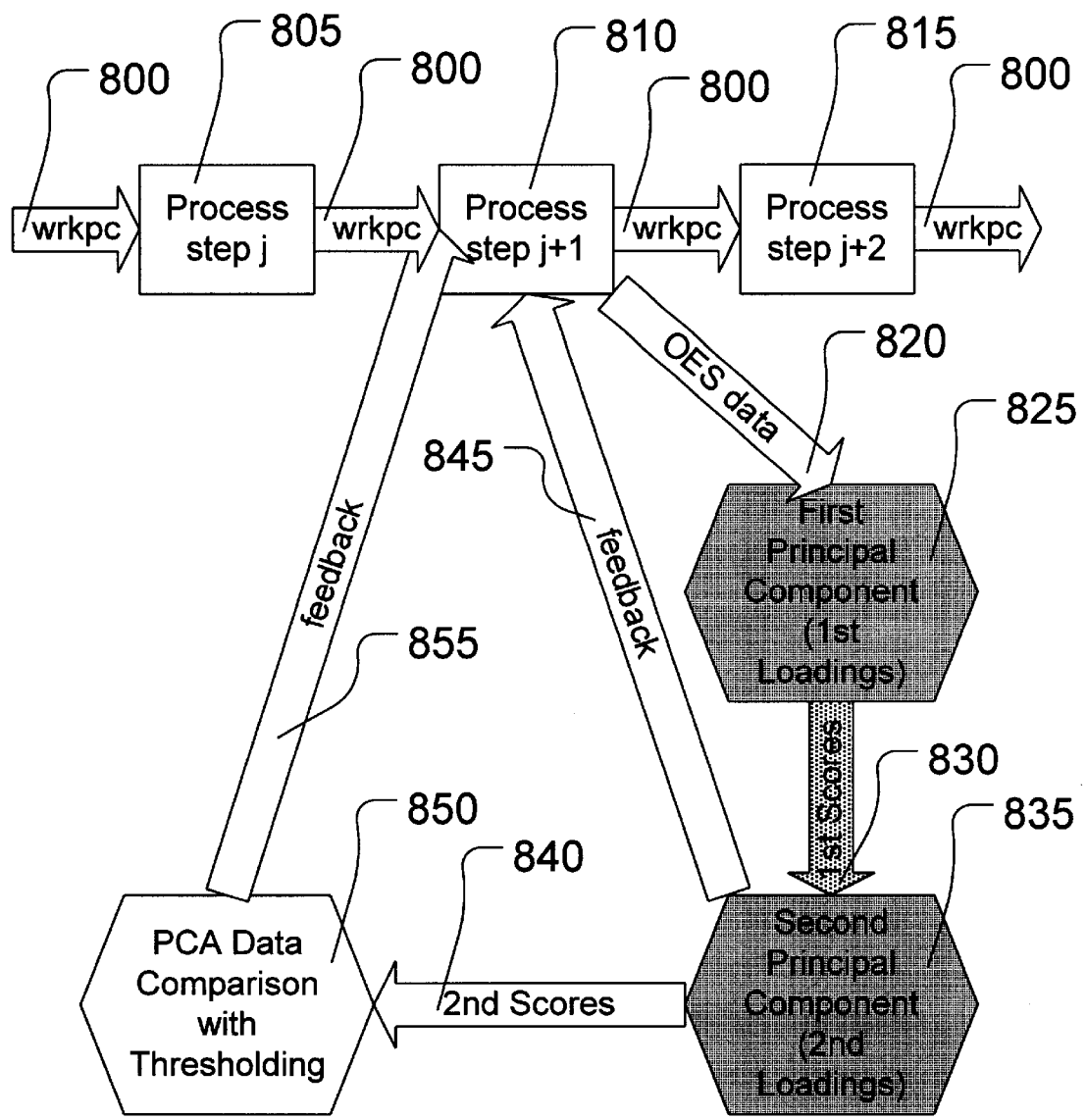

As shown in FIG. 11, the 1st Scores signal 830 is sent from the first Principal Component (1st Loadings) determination step 825 to a second Principal Component (2nd Loadings) determination step 835. In the second Principal Component (2nd Loadings) determination step 835, the second Principal Component (2nd Loadings) and 2nd Scores, corresponding to the second Principal Component (2nd Loadings), may be determined from the OES data 820 and the 1st Scores signal 830, for example, by any of the techniques discussed above, producing the 2nd Scores signal 840.

Figure 12:
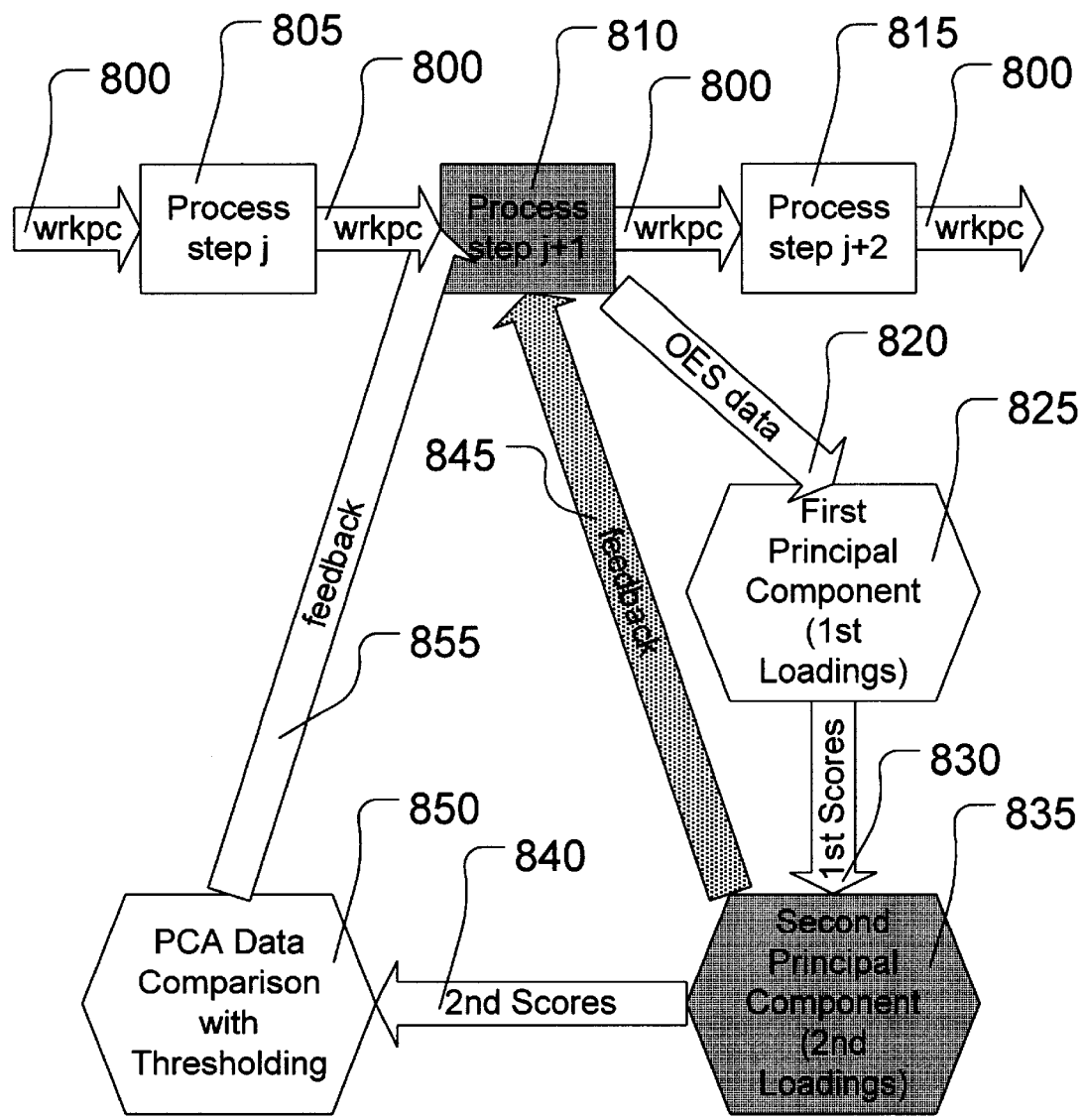

As shown in FIG. 12, a feedback control signal 845 may be sent from the second Principal Component (2nd Loadings) determination step 835 to the etching step j+1 810 to adjust the processing performed in the etching step j+1 810. For example, based on the determination of the first and second Principal Components (1st and 2nd Loadings), and the 1st and 2nd Scores corresponding to the first and second Principal Components (1st and 2nd Loadings), the feedback control signal 845 may be used to signal the etch endpoint.

Figure 13:
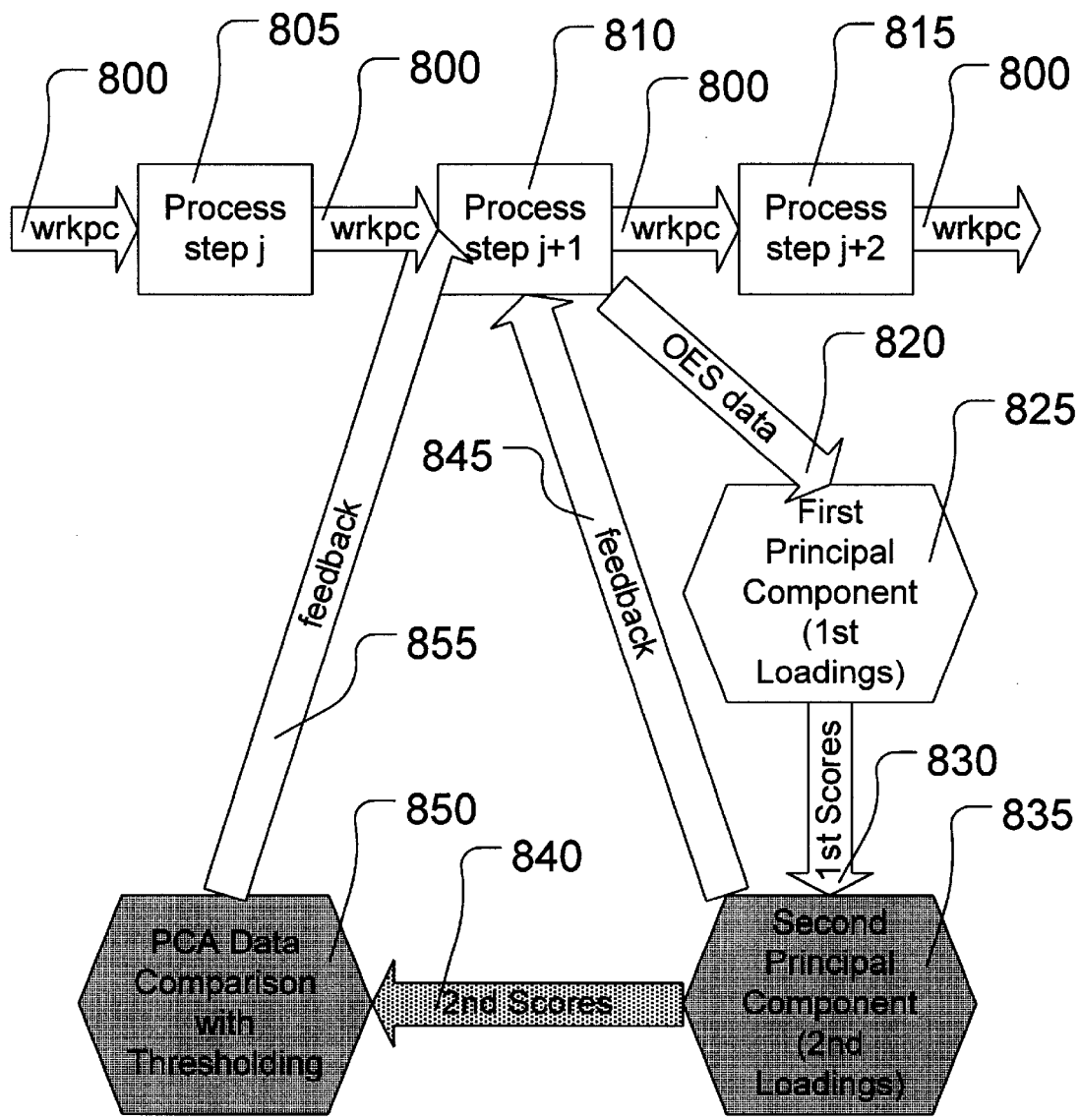

As shown in FIG. 13, in addition to, and/or instead of, the feedback control signal 835, the 2nd Scores signal 840 may be sent from the second Principal Component (2nd Loadings) determination step 835 and may then be delivered to a PCA data comparison with thresholding step 850. In the PCA data comparison with thresholding step 850, archived data sets of OES wavelengths (or frequencies), from wafers that had previously been plasma etched, may be compared with the OES data 820, above a preselected threshold, measured in situ in the etching step 810, and the comparison with thresholding may be used to determine an etch endpoint. For example, instead of using Loadings for all wavelengths sampled, the Loadings may be compared with a certain threshold value (such as approximately 0.03) and only those wavelengths with loadings greater than or equal to the threshold value may be used to determine the etch endpoint. In this way, relatively unimportant wavelengths may be ignored and the robustness of this embodiment may be further enhanced.

Figure 14:
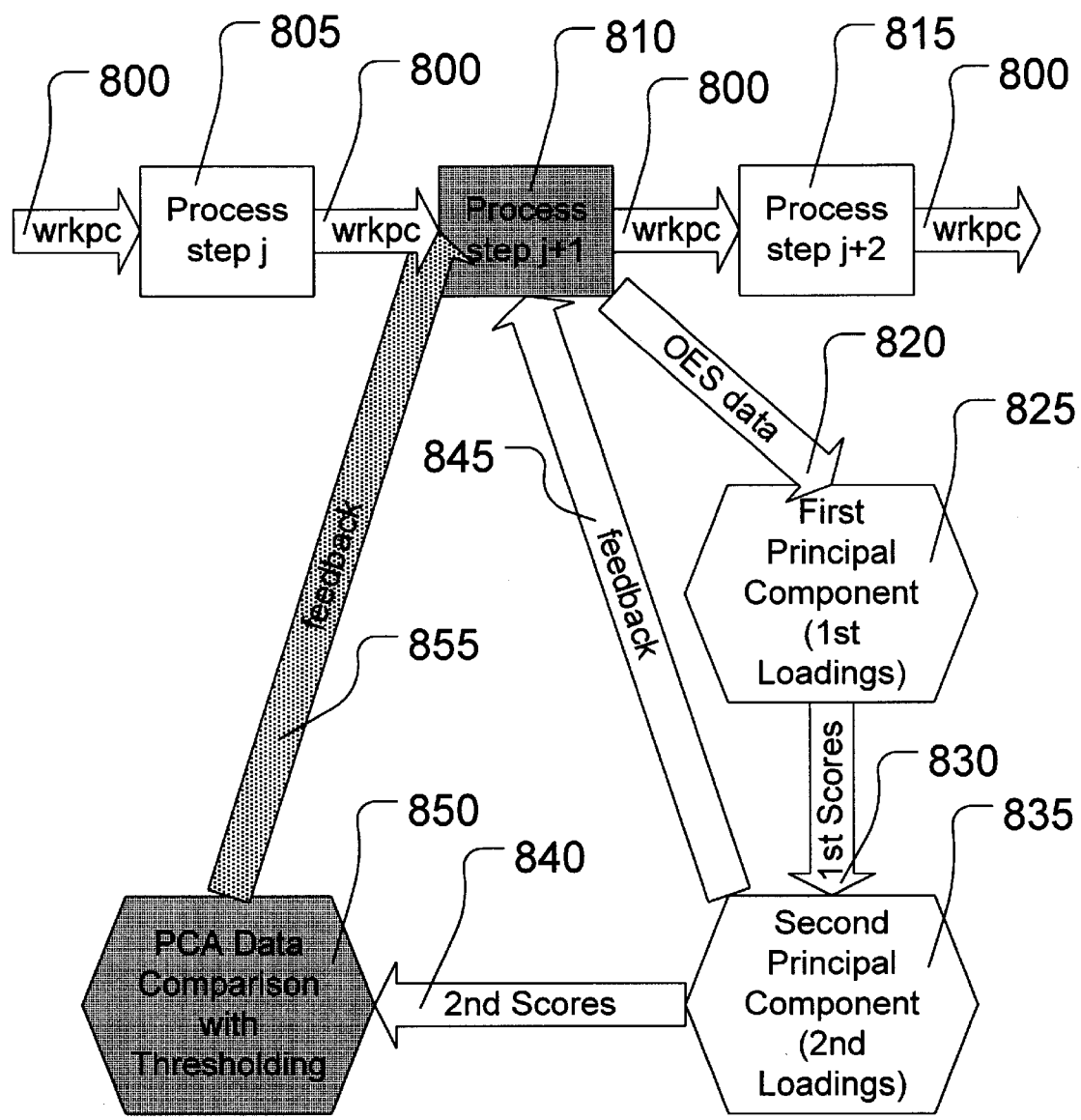

As shown in FIG. 14, a feedback control signal 855 may be sent from the PCA data comparison with thresholding step 850 to the etching step j+1 810 to adjust the processing performed in the etching step j+1 810. For example, based on the determination and comparison of the respective first and second Principal Components (1st and 2nd Loadings), and the 1st and 2nd Scores corresponding to the respective first and second Principal Components (1st and 2nd Loadings), the feedback control signal 855 may be used to signal the etch endpoint.

In yet another illustrative embodiment of a method according to the present invention, as shown in FIGS. 15–21, the determination of the second Principal Component may be performed real-time in an early part of a plasma etching process, and this determination of the second Principal Component may be used to determine an etch endpoint.

Figure 15:
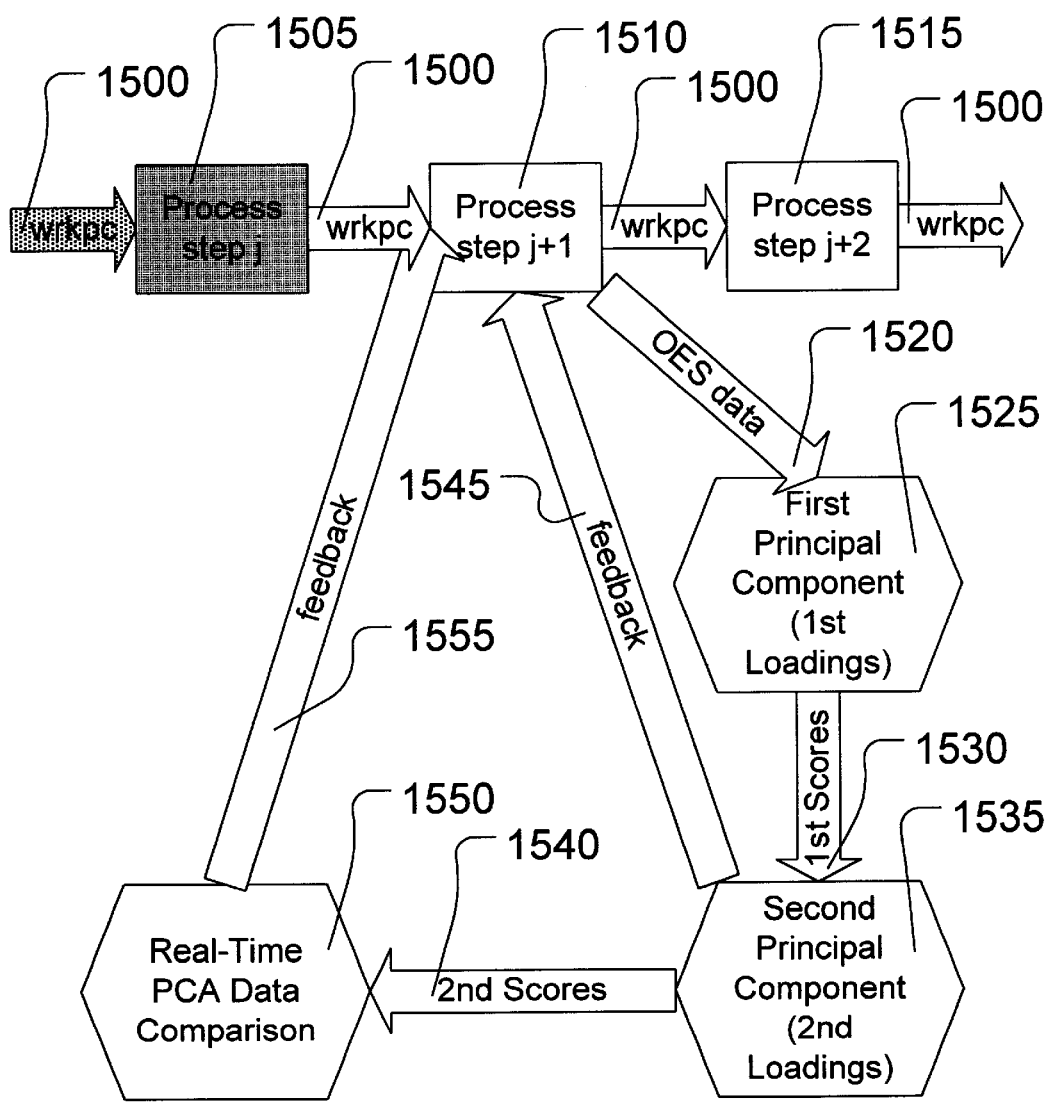
FIGS. 15–21 schematically illustrate a flow diagram for yet other various embodiments of a method according to the present invention.

As shown in FIG. 15, a workpiece 1500, such as a semiconducting substrate or wafer, having one or more process layers and/or semiconductor devices such as an MOS transistor disposed thereon, for example, is delivered to an etching preprocessing step j 1505, where j may have any value from j=1 to j=N−1. The total number N of processing steps, such as masking, etching, depositing material and the like, used to form the finished workpiece 1500, may range from N=1 to about any finite value.

Figure 16:
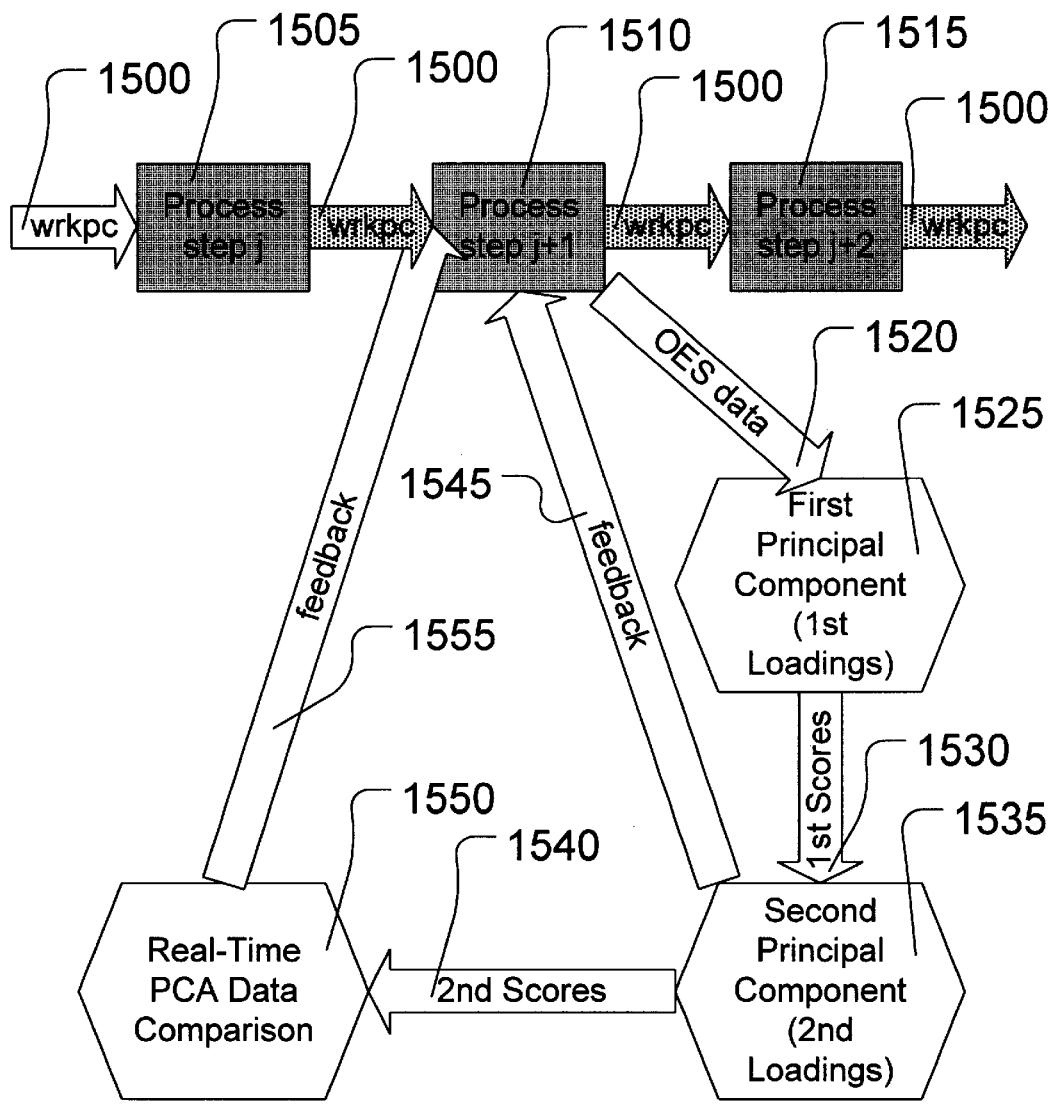

As shown in FIG. 16, the workpiece 1500 is sent from the etching preprocessing step j 1505 to an etching step j+1 1510. In the etching step j+1 1510, the workpiece 1500 is etched to remove selected portions from one or more process layers formed in any of the previous processing steps (such as etching preprocessing step j 1505, where j may have any value from j=1 to j=N−1). As shown in FIG. 16, if there is further processing to do on the workpiece 1500 (if j<N−1), then the workpiece 1500 may be sent from the etching step j+1 1510 and delivered to a postetching processing step j+2 1515 for further postetch processing, and then sent on from the postetching processing step j+2 1515. Alternatively, the etching step j+1 1510 may be the final step in the processing of the workpiece 1500. In the etching step j+1 1510, OES spectra are measured in situ by an OES spectrometer (not shown), producing OES data 1520 indicative of the state of the workpiece 1500 during the etching.

Figure 17:
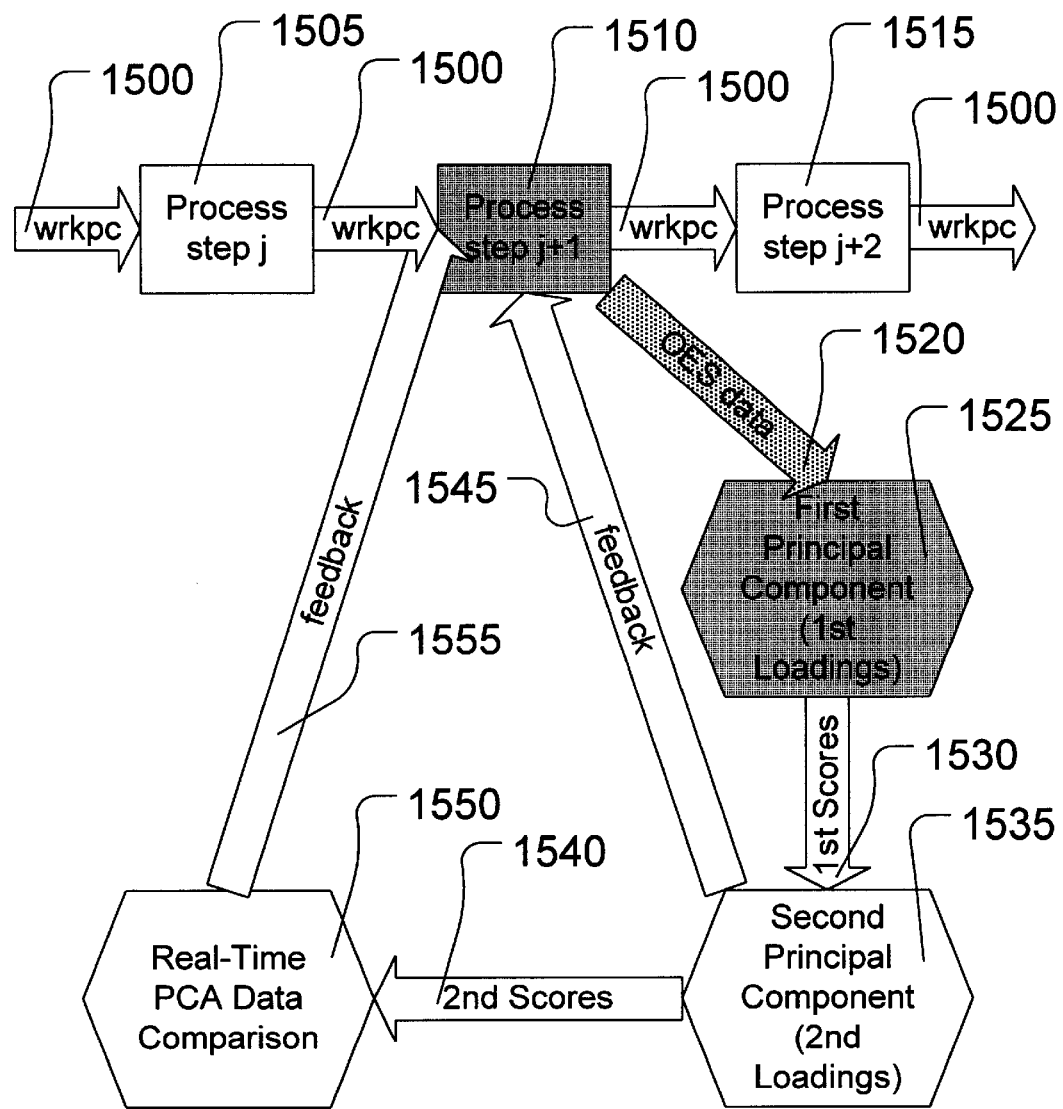

As shown in FIG. 17, the OES data 1520 is sent from the etching step j+1 1510 and delivered to a first Principal Component (1st Loadings) determination step 1525. In the first Principal Component (1st Loadings) determination step 1525, the first Principal Component (1st Loadings) and 1st Scores, corresponding to the first Principal Component (1st Loadings), may be determined from the OES data 1520, for example, by any of the techniques discussed above, producing the 1st Scores signal 1530.

Figure 18:
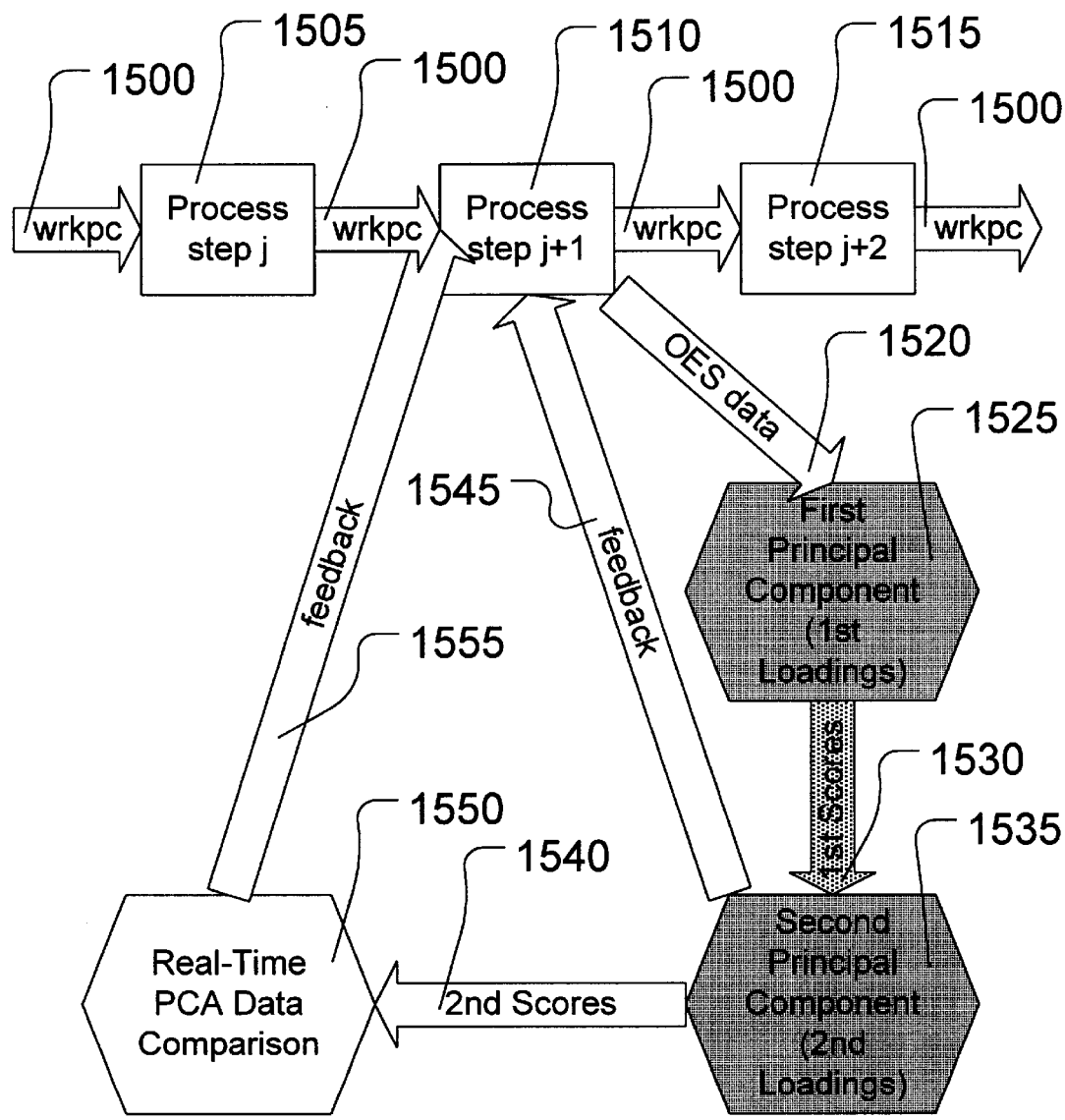

As shown in FIG. 18, the 1st Scores signal 1530 is sent from the first Principal Component (1st Loadings) determination step 1525 to a second Principal Component (2nd Loadings) determination step 1535. In the second Principal Component (2nd Loadings) determination step 1535, the second Principal Component (2nd Loadings) and 2nd Scores, corresponding to the second Principal Component (2nd Loadings), may be determined from the OES data 1520 and the 1st Scores signal 1530, for example, by any of the techniques discussed above, producing the 2nd Scores signal 1540.

Figure 19:
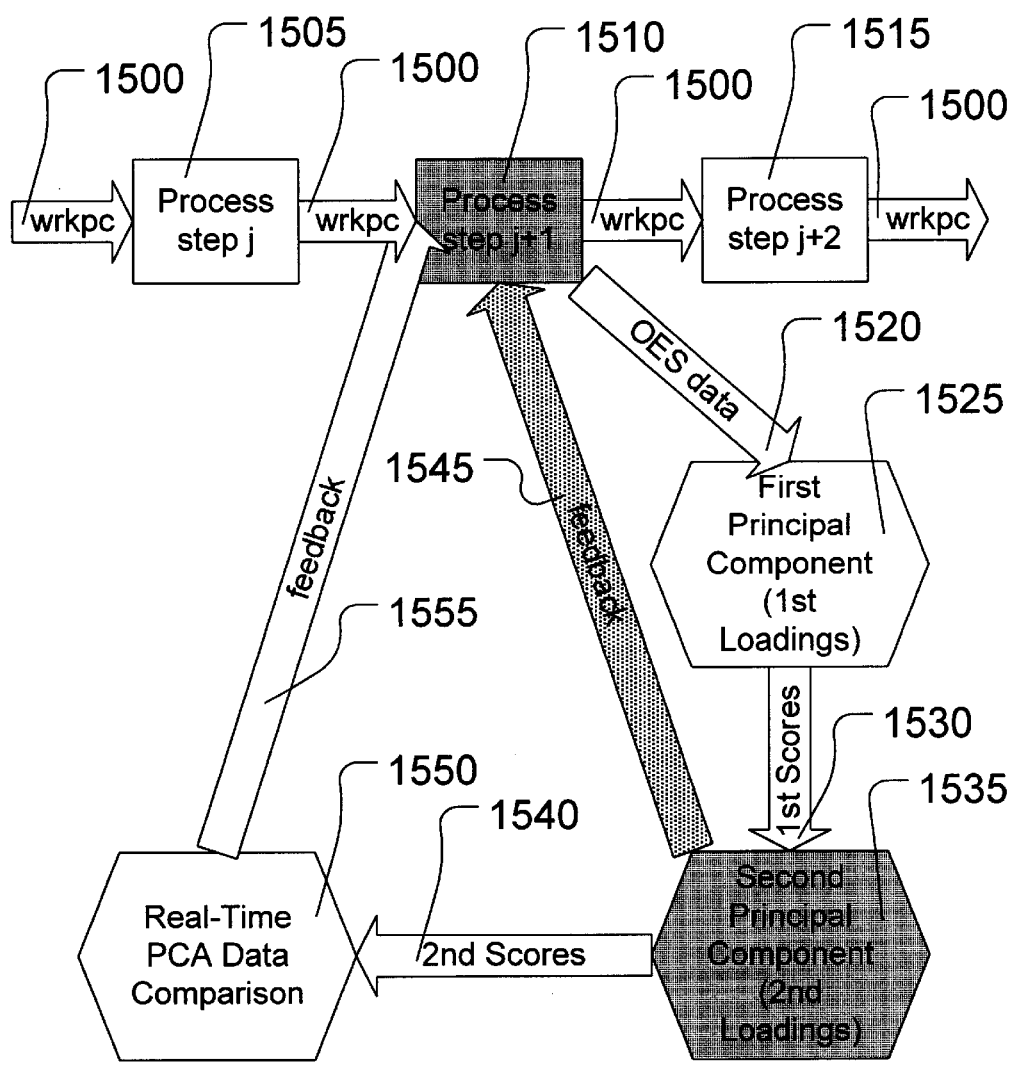

As shown in FIG. 19, a feedback control signal 1545 may be sent from the second Principal Component (2nd Loadings) determination step 1535 to the etching step j+1 1510 to adjust the processing performed in the etching step j+1 1510. For example, based on the determination of the first and second Principal Components (1st and 2nd Loadings), and the 1st and 2nd Scores corresponding to the first and second Principal Components (1st and 2nd Loadings), the feedback control signal 1545 may be used to signal the etch endpoint.

Figure 20:
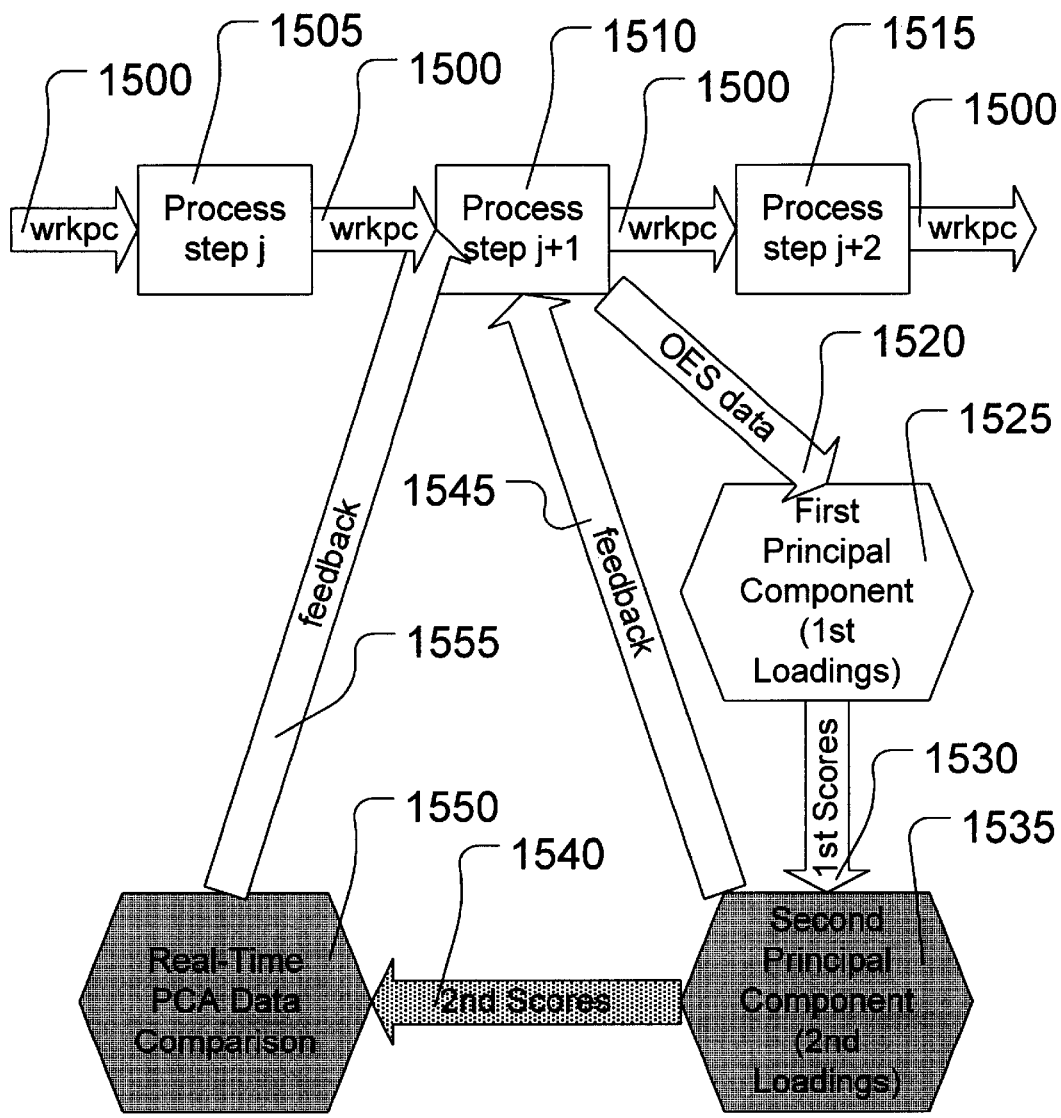

As shown in FIG. 20, in addition to, and/or instead of, the feedback control signal 1535, the 2nd Scores signal 1540 may be sent from the second Principal Component (2nd Loadings) determination step 1535 and may then be delivered to a real-time PCA data comparison step 1550. In the real-time PCA data comparison step 1550, the determination of the second Principal Component may be performed real-time in an early part of a plasma etching process, and this determination of the second Principal Component may be used to determine an etch endpoint. In particular, first and second Principal Components (with respective 1st and 2nd Loadings), and the 1st and 2nd Scores corresponding to the first and second Principal Components (with respective 1st and 2nd Loadings), previously determined from the data sets of OES wavelengths (or frequencies) taken in an earlier part of the same plasma etching process in etching step j+1 1510, may be compared with the first and second Principal Components (with respective 1st and 2nd Loadings), and the 1st and 2nd Scores corresponding to the first and second Principal Components (with respective 1st and 2nd Loadings), taken in a later part of the same plasma etching process in etching step j+1 1510, determined in the first Principal Component (1st Loadings) determination step 1525 and the second Principal Component (2nd Loadings) determination step 1535. This real-time comparison of the respective PCA information may be used to determine an etch endpoint.

For example, when used in real-time, respective model Loadings can be further adjusted based on real-time calculations. These adjustments can be wafer-to-wafer (during serial etching of a batch of wafers) and/or within the etching of each single wafer. For wafer-to-wafer adjustments, the Loadings from previous wafers may be used as the model Loadings. Within the etching of individual wafers, the model Loadings may be calculated from an early portion of the plasma etching process where the etching endpoint almost certainly will not be occurring.

Figure 21:
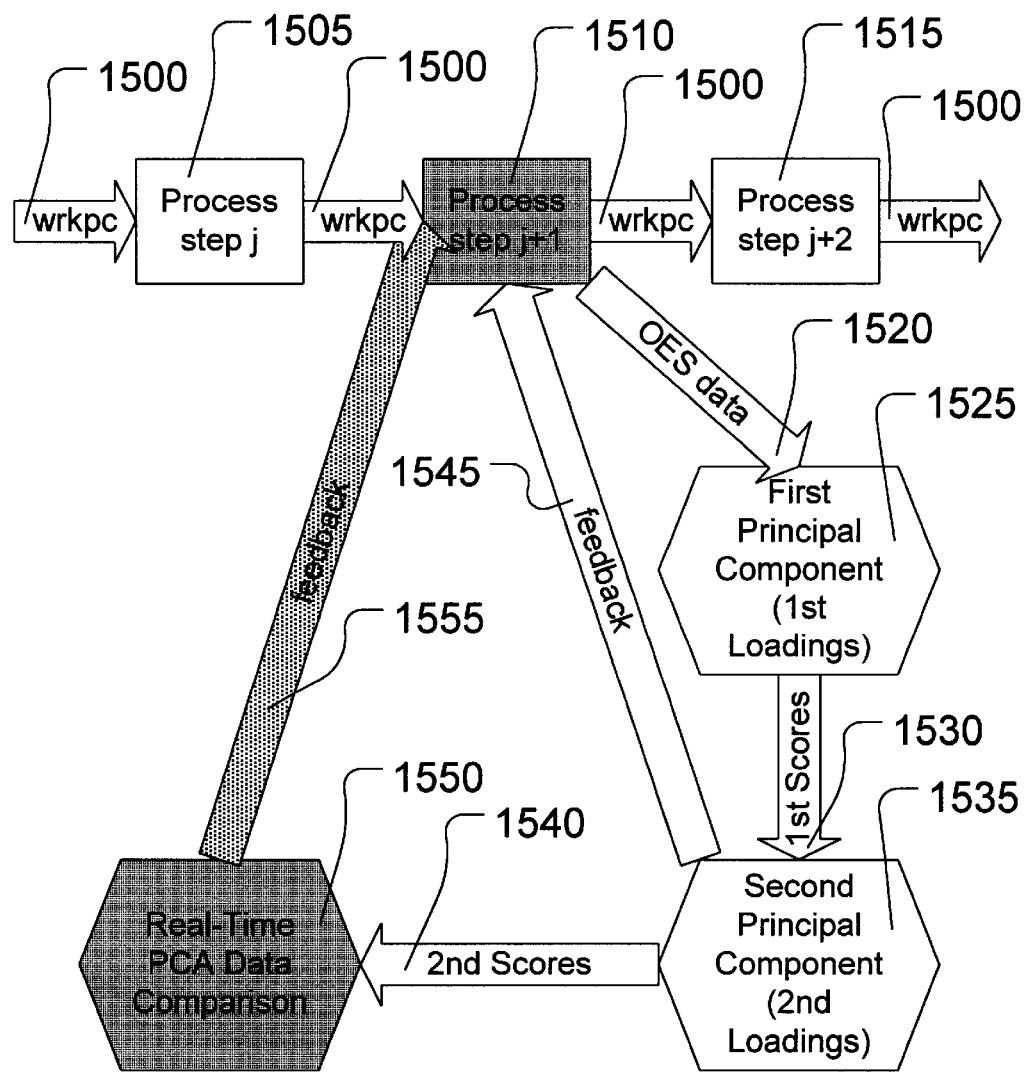

As shown in FIG. 21, a feedback control signal 1555 may be sent from the real-time PCA data comparison step 1550 to the etching step j+1 1510 to adjust the processing performed in the etching step j+1 1510. For example, based on the determination and comparison of the respective first and second Principal Components (1st and 2nd Loadings), and the 1st and 2nd Scores corresponding to the respective first and second Principal Components (1st and 2nd Loadings), the feedback control signal 1555 may be used to signal the etch endpoint.

Figure 30:
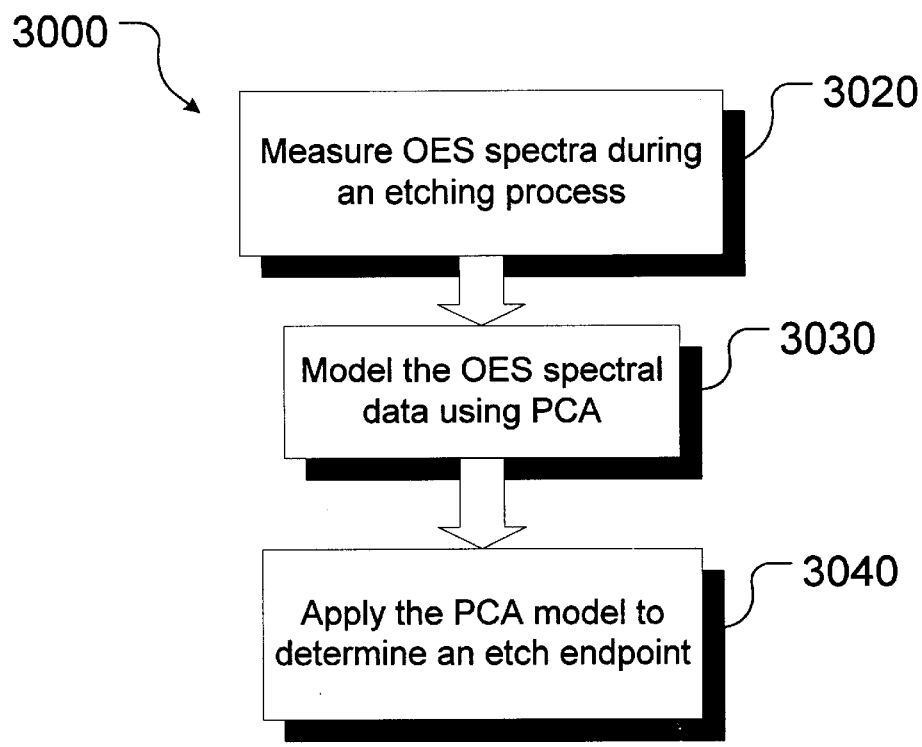
FIG. 30 schematically illustrates a method for fabricating a semiconductor device practiced in accordance with the present invention.
Figure 31:
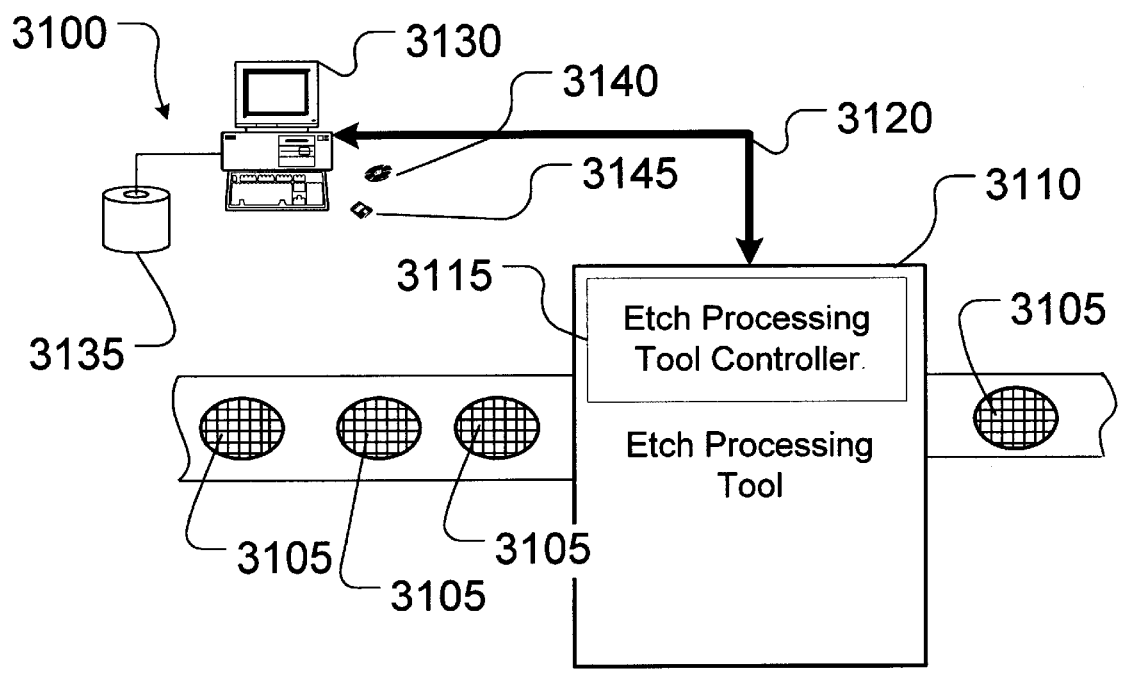
FIG. 31 schematically illustrates workpieces being processed using a high-density plasma (HDP) etch processing tool, using a plurality of control input signals, in accordance with the present invention.

FIG. 30 illustrates one particular embodiment of a method 3000 practiced in accordance with the present invention. FIG. 31 illustrates one particular apparatus 3100 with which the method 3000 may be practiced. For the sake of clarity, and to further an understanding of the invention, the method 3000 shall be disclosed in the context of the apparatus 3100. However, the invention is not so limited and admits wide variation, as is discussed further below.

Referring now to both FIGS. 30 and 31, a batch or lot of workpieces or wafers 3105 is being processed through an etch processing tool 3110. The etch processing tool 3110 may be any etch processing tool known to the art, such as Applied Materials AMAT 5300 Centura etching chamber, provided it includes the requisite control capabilities. The etch processing tool 3110 includes an etch processing tool controller 3115 for this purpose. The nature and function of the etch processing tool controller 3115 will be implementation specific. For instance, the etch processing tool controller 3115 may control etch control input parameters such as etch recipe control input parameters and etch endpoint control parameters, and the like. Four workpieces 3105 are shown in FIG. 31, but the lot of workpieces or wafers, ie., the "wafer lot," may be any practicable number of wafers from one to any finite number.

The method 3000 begins, as set forth in box 3020, by measuring parameters such as OES spectral data characteristic of the etch processing performed on the workpiece 3105 in the etch processing tool 3110. The nature, identity, and measurement of characteristic parameters will be largely implementation specific and even tool specific. For instance, capabilities for monitoring process parameters vary, to some degree, from tool to tool. Greater sensing capabilities may permit wider latitude in the characteristic parameters that are identified and measured and the manner in which this is done. Conversely, lesser sensing capabilities may restrict this latitude.

Turning to FIG. 31, in this particular embodiment, the etch process characteristic parameters are measured and/or monitored by tool sensors (not shown). The outputs of these tool sensors are transmitted to a computer system 3130 over a line 3120. The computer system 3130 analyzes these sensor outputs to identify the characteristic parameters.

Returning, to FIG. 30, once the characteristic parameter is identified and measured, the method 3000 proceeds by modeling the measured and identified characteristic parameter using PCA, as set forth in box 3030. The computer system 3130 in FIG. 31 is, in this particular embodiment, programmed to model the characteristic parameter using PCA. The manner in which this PCA modeling occurs will be implementation specific.

In the embodiment of FIG. 31, a database 3135 stores a plurality of PCA models and/or archived PCA data sets that might potentially be applied, depending upon which characteristic parameter is identified. This particular embodiment, therefore, requires some a priori knowledge of the characteristic parameters that might be measured. The computer system 3130 then extracts an appropriate model from the database 3135 of potential models to apply to the identified characteristic parameters. If the database 3135 does not include an appropriate model, then the characteristic parameter may be ignored, or the computer system 3130 may attempt to develop one, if so programmed. The database 3135 may be stored on any kind of computer-readable, program storage medium, such as an optical disk 3140, a floppy disk 3145, or a hard disk drive (not shown) of the computer system 3130. The database 3135 may also be stored on a separate computer system (not shown) that interfaces with the computer system 3130.

Modeling of the identified characteristic parameter may be implemented differently in alternative embodiments. For instance, the computer system 3130 may be programmed using some form of artificial intelligence to analyze the sensor outputs and controller inputs to develop a PCA model on-the-fly in a real-time PCA implementation. This approach might be a useful adjunct to the embodiment illustrated in FIG. 31, and discussed above, where characteristic parameters are measured and identified for which the database 3135 has no appropriate model.

The method 3000 of FIG. 30 then proceeds by applying the PCA model to determine an etch endpoint, as set forth in box 3040. Depending on the implementation, applying the PCA model may yield either a new value for the etch endpoint control parameter or a correction and/or update to the existing etch endpoint control parameter. The new etch endpoint control parameter is then formulated from the value yielded by the PCA model and is transmitted to the etch processing tool controller 3115 over the line 3120. The etch processing tool controller 3115 then controls subsequent etch process operations in accordance with the new etch control inputs.

Some alternative embodiments may employ a form of feedback to improve the PCA modeling of characteristic parameters. The implementation of this feedback is dependent on several disparate facts, including the tool's sensing capabilities and economics. One technique for doing this would be to monitor at least one effect of the PCA model's implementation and update the PCA model based on the effect(s) monitored. The update may also depend on the PCA model. For instance, a linear model may require a different update than would a non-linear model, all other factors being the same.

As is evident from the discussion above, some features of the present invention are implemented in software. For instance, the acts set forth in the boxes 3020–3040 in FIG. 30 are, in the illustrated embodiment, software-implemented, in whole or in part. Thus, some features of the present invention are implemented as instructions encoded on a computer-readable, program storage medium. The program storage medium may be of any type suitable to the particular implementation. However, the program storage medium will typically be magnetic, such as the floppy disk 3145 or the computer 3130 hard disk drive (not shown), or optical, such as the optical disk 3140. When these instructions are executed by a computer, they perform the disclosed functions. The computer may be a desktop computer, such as the computer 3130. However, the computer might alternatively be a processor embedded in the etch processing tool 3110. The computer might also be a laptop, a workstation, or a mainframe in various other embodiments. The scope of the invention is not limited by the type or nature of the program storage medium or computer with which embodiments of the invention might be implemented.

Thus, some portions of the detailed descriptions herein are, or may be, presented in terms of algorithms, functions, techniques, and/or processes. These terms enable those skilled in the art most effectively to convey the substance of their work to others skilled in the art. These terms are here, and are generally, conceived to be a self-consistent sequence of steps leading to a desired result. The steps are those requiring physical manipulations of physical quantities. Usually, though not necessarily, these quantities take the form of electromagnetic signals capable of being stored, transferred, combined, compared, and otherwise manipulated.

It has proven convenient at times, principally for reasons of common usage, to refer to these signals as bits, values, elements, symbols, characters, terms, numbers, and the like. All of these and similar terms are to be associated with the appropriate physical quantities and are merely convenient labels applied to these quantities and actions. Unless specifically stated otherwise, or as may be apparent from the discussion, terms such as "processing," "computing," "calculating," "determining," "displaying," and the like, used herein refer to the action(s) and processes of a computer system, or similar electronic and/or mechanical computing device, that manipulates and transforms data, represented as physical (electromagnetic) quantities within the computer system's registers and/or memories, into other data similarly represented as physical quantities within the computer system's memories and/or registers and/or other such information storage, transmission and/or display devices.

Any of these illustrative embodiments may be applied in real-time etch processing. Alternatively, either of the illustrative embodiments shown in FIGS. 1–7 and 8–14 may be used as an identification technique when using batch etch processing, with archived data being applied statistically, to determine an etch endpoint for the batch.

In various illustrative embodiments, a process engineer may be provided with advanced process data monitoring capabilities, such as the ability to provide historical parametric data in a user-friendly format, as well as event logging, real-time graphical display of both current processing parameters and the processing parameters of the entire run, and remote, i.e., local site and worldwide, monitoring. These capabilities may engender more optimal control of critical processing parameters, such as throughput accuracy, stability and repeatability, processing temperatures, mechanical tool parameters, and the like. This more optimal control of critical processing parameters reduces this variability. This reduction in variability manifests itself as fewer within-run disparities, fewer run-to-run disparities and fewer tool-to-tool disparities. This reduction in the number of these disparities that can propagate means fewer deviations in product quality and performance. In such an illustrative embodiment of a method of manufacturing according to the present invention, a monitoring and diagnostics system may be provided that monitors this variability and optimizes control of critical parameters.

An etch endpoint determination signal as in any of the embodiments disclosed above may have a high signal-to-noise ratio and may be reproducible over the variations of the incoming wafers and the state of the processing chamber, for example, whether or not the internal hardware in the processing chamber is worn or new, or whether or not the processing chamber is in a "clean" or a "dirty" condition. Further, in particular applications, for example, the etching of contact and/or via holes, an etch endpoint determination signal as in any of the embodiments disclosed above may have a high enough signal-to-noise ratio to overcome the inherently very low signal-to-noise ratio that may arise simply by virtue of the small percentage (1% or so) of surface area being etched. In various illustrative embodiments, the etch endpoint signal becomes very stable, and may throughput may be improved by reducing the main etch time from approximately 145 seconds, for example, to approximately 90–100 seconds, depending on the thickness of the oxide. In the absence of an etch endpoint determination signal as in any of the embodiments disclosed above, a longer etch time is conventionally needed to insure that all the material to be etched away has been adequately etched away, even in vias and contact holes with high aspect ratios. The presence of a robust etch endpoint determination signal as in any of the embodiments disclosed above thus allows for a shorter etch time, and, hence, increased throughput, compared to conventional etching processes.

Thus, embodiments of the present invention fill a need in present day and future technology for optimizing selection of wavelengths to monitor for endpoint determination or detection during etching. Similarly, embodiments of the present invention fill a need in present day and future technology for being able to determine an etch endpoint expeditiously, robustly, reliably and reproducibly under a variety of different conditions, even in real-time processing.

Further, it should be understood that the present invention is applicable to any plasma etching system, including reactive ion etching (RIE), high-density, inductively coupled plasma (ICP) systems, electron cyclotron resonance (ECR) systems, radio frequency induction systems, and the like.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method for determining an etch endpoint, the method comprising:

collecting intensity data representative of optical emission spectral wavelengths during a plasma etch process;

analyzing at least a portion of the collected intensity data into at most first and second Principal Components with respective Loadings and corresponding Scores; and determining the etch endpoint using the respective Loadings and corresponding Scores of the second Principal Component as an indicator for the etch endpoint using thresholding applied to the respective Loadings of the second Principal Component.

2. The method of claim 1, wherein determining the etch endpoint includes using a trace of Scores corresponding to at least one of the first and the second Principal Components along time to signal the etch endpoint.

3. The method of claim 2, wherein using the trace of the Scores corresponding to the at least one of the first and the second Principal Components along time to signal the etch endpoint includes using the trace of the Scores corresponding to the second Principal Component along time to signal the etch endpoint.

4. The method of claim 1 wherein determining the etch endpoint further comprises:

selecting multiple wavelengths as indicator variables based on the respective Loadings of at least one of the first and the second Principal Components, the multiple wavelengths varying during the plasma process so that the etch endpoint can be determined by monitoring the multiple wavelengths.

5. The method of claim 2 wherein determining the etch endpoint further comprises:

selecting multiple wavelengths as indicator variables based on the respective Loadings of the second Principal Component, the multiple wavelengths varying during the plasma process so that the etch endpoint can be determined by monitoring the multiple wavelengths.

6. The method of claim 3 wherein determining the etch endpoint further comprises:

selecting multiple wavelengths as indicator variables based on the respective Loadings of the second Principal Component, the multiple wavelengths varying during the plasma process so that the etch endpoint can be determined by monitoring the multiple wavelengths.

7. The method of claim 1 further comprising mean-scaling the at least the portion of the collected intensity data prior to analyzing the at least the portion of the collected intensity data.

8. The method of claim 1, wherein analyzing the at least the portion of the collected intensity data into the at most first and second Principal Components includes using an eigenanalysis method.

9. The method of claim 1, wherein analyzing the at least the portion of the collected intensity data into the at most first and second Principal Components includes using a singular value decomposition method.

10. The method of claim 1, wherein analyzing the at least the portion of the collected intensity data into the at most first and second Principal Components includes using a power method.

11. A method for etching a wafer, the method comprising:

etching a wafer using a plasma process so that a light-emitting discharge is produced;

terminating the etching of the wafer when an etch endpoint is determined, wherein the determination of the etch endpoint further comprises:

collecting intensity data representative of optical emission spectral wavelengths during a plasma etch process;

analyzing at least a portion of the collected intensity data into at most first and second Principal Components with respective Loadings and corresponding Scores; and determining the etch endpoint using the respective Loadings and corresponding Scores of the second Principal Component as an indicator for the etch endpoint using thresholding applied to the respective Loadings of the second Principal Component.

12. The method of claim 11, wherein determining the etch endpoint includes using a trace of Scores corresponding to at least one of the first and the second Principal Components along time to signal the etch endpoint.

13. The method of claim 12, wherein using the trace of the Scores corresponding to the at least one of the first and the second Principal Components along time to signal the etch endpoint includes using the trace of the Scores corresponding to the second Principal Component along time to signal the etch endpoint.

14. The method of claim 11 wherein determining the etch endpoint further comprises:

selecting multiple wavelengths as indicator variables based on the respective Loadings of at least one of the first and the second Principal Components, the multiple wavelengths varying during the plasma process so that the etch endpoint can be determined by monitoring the multiple wavelengths.

15. The method of claim 12 wherein determining the etch endpoint further comprises:

selecting multiple wavelengths as indicator variables based on the respective Loadings of the second Principal Component, the multiple wavelengths varying during the plasma process so that the etch endpoint can be determined by monitoring the multiple wavelengths.

16. The method of claim 13 wherein determining the etch endpoint further comprises:

selecting multiple wavelengths as indicator variables based on the respective Loadings of the second Principal Component, the multiple wavelengths varying during the plasma process so that the etch endpoint can be determined by monitoring the multiple wavelengths.

17. The method of claim 11 further comprising mean-scaling the at least the portion of the collected intensity data prior to analyzing the at least the portion of the collected intensity data.

18. The method of claim 11, wherein analyzing the at least the portion of the collected intensity data into the at most first and second Principal Components includes using an eigenanalysis method.

19. The method of claim 11, wherein analyzing the at least the portion of the collected intensity data into the at most first and second Principal Components includes using a singular value decomposition method.

20. The method of claim 11, wherein analyzing the at least the portion of the collected intensity data into the at most first and second Principal Components includes using a power method.

21. A method for determining an etch endpoint, the method comprising:

collecting intensity data representative of optical emission spectral wavelengths during a plasma etch process;

analyzing the collected intensity data into at most first and second Principal Components; and determining the etch endpoint using Loadings and Scores corresponding to the second Principal Component as an indicator for the etch endpoint using thresholding applied to the Loadings corresponding to the second Principal Component.

22. The method of claim 21, wherein determining the etch endpoint using the Scores corresponding to the second Principal Component as an indicator includes using a trace of Scores of at least one of the first and the second Principal Components along time to signal the etch endpoint.

23. The method of claim 22, wherein using the trace of the Scores of the at least one of the first and the second Principal Components along time to signal the etch endpoint includes using the trace of the Scores of the second Principal Component along time to signal the etch endpoint.

24. The method of claim 21 wherein determining the etch endpoint using the Scores corresponding to the second Principal Component as an indicator further comprises:

selecting multiple wavelengths as indicator variables based on Loadings of at least one of the first and the second Principal Components, the multiple wavelengths varying during the plasma process so that the etch endpoint can be determined by monitoring the multiple wavelengths.

25. The method of claim 22 wherein determining the etch endpoint using the Scores corresponding to the second Principal Component as an indicator further comprises:

selecting multiple wavelengths as indicator variables based on the Loadings corresponding to the second Principal Component, the multiple wavelengths varying during the plasma process so that the etch endpoint can be determined by monitoring the multiple wavelengths.

26. The method of claim 23 wherein determining the etch endpoint using the Scores corresponding to the second Principal Component as the indicator further comprises:

selecting multiple wavelengths as indicator variables based on the Loadings corresponding to the second Principal Component, the multiple wavelengths varying during the plasma process so that the etch endpoint can be determined by monitoring the multiple wavelengths.

27. The method of claim 21 further comprising mean-scaling the collected intensity data prior to analyzing the collected intensity data.

28. The method of claim 21, wherein analyzing the collected intensity data into the at most first and second Principal Components includes using an eigenanalysis method.

29. The method of claim 21, wherein analyzing the collected intensity data into the at most first and second Principal Components includes using a singular value decomposition method.

30. The method of claim 21, wherein analyzing the collected intensity data into the at most first and second Principal Components includes using a power method.

31. A method for etching a wafer, the method comprising:

etching a wafer using a plasma process so that a light-emitting discharge is produced;

terminating the etching of the wafer when an etch endpoint is determined, wherein the determination of the etch endpoint further comprises:

collecting intensity data representative of optical emission spectral wavelengths during a plasma etch process;

analyzing the collected intensity data into at most first and second Principal Components; and determining the etch endpoint using Loadings and Scores corresponding to the second Principal Component as an indicator for the etch endpoint using thresholding applied to the Loadings corresponding to the second Principal Component.

32. The method of claim 31, wherein determining the etch endpoint using the Scores corresponding to the second Principal Component as an indicator includes using a trace of Scores of at least one of the first and the second Principal Components along time to signal the etch endpoint.

33. The method of claim 32, wherein using the trace of the Scores of the at least one of the first and the second Principal Components along time to signal the etch endpoint includes using the trace of the Scores of the second Principal Component along time to signal the etch endpoint.

34. The method of claim 31 wherein determining the etch endpoint using the Scores corresponding to the second Principal Component as an indicator further comprises:

selecting multiple wavelengths as indicator variables based on Loadings of at least one of the first and the second Principal Components, the multiple wavelengths varying during the plasma process so that the etch endpoint can be determined by monitoring the multiple wavelengths.

35. The method of claim 32 wherein determining the etch endpoint using the Scores corresponding to the second Principal Component as an indicator further comprises:

selecting multiple wavelengths as indicator variables based on the Loadings corresponding to the second Principal Component, the multiple wavelengths varying during the plasma process so that the etch endpoint can be determined by monitoring the multiple wavelengths.

36. The method of claim 33 wherein determining the etch endpoint using the Scores corresponding to the second Principal Component as the indicator further comprises:

selecting multiple wavelengths as indicator variables based on the Loadings corresponding to the second Principal Component, the multiple wavelengths varying during the plasma process so that the etch endpoint can be determined by monitoring the multiple wavelengths.

37. The method of claim 31 further comprising mean-scaling the collected intensity data prior to analyzing the collected intensity data.

38. The method of claim 31, wherein analyzing the collected intensity data into the at most first and second Principal Components includes using an eigenanalysis method.

39. The method of claim 31, wherein analyzing the collected intensity data into the at most first and second Principal Components includes using a singular value decomposition method.

40. The method of claim 31, wherein analyzing the collected intensity data into the at most first and second Principal Components includes using a power method.

41. A computer-readable, program storage device encoded with instructions that, when executed by a computer, perform a method, the method comprising:

collecting intensity data representative of optical emission spectral wavelengths during a plasma etch process;

analyzing at least a portion of the collected intensity data into at most first and second Principal Components with respective Loadings and corresponding Scores; and determining the etch endpoint using the respective Loadings and corresponding Scores of the second Principal Component as an indicator for the etch endpoint using thresholding applied to the respective Loadings of the second Principal Component.

42. A computer programmed to perform a method, the method comprising:

collecting intensity data representative of optical emission spectral wavelengths during a plasma etch process;

analyzing at least a portion of the collected intensity data into at most first and second Principal Components with respective Loadings and corresponding Scores; and determining the etch endpoint using the respective Loadings and corresponding Scores of the second Principal Component as an indicator for the etch endpoint using thresholding applied to the respective Loadings of the second Principal Component.

* * * * *